US012745559B2

(12) United States Patent
Hur et al.

(10) Patent No.: US 12,745,559 B2
(45) Date of Patent: Sep. 22, 2026

(54) LIGHT-EMITTING DEVICE AND ELECTRONIC APPARATUS INCLUDING THE SAME

(71) Applicant: Samsung Display Co., Ltd., Yongin-si (KR)

(72) Inventors: Jaeweon Hur, Yongin-si (KR); Seulong Kim, Yongin-si (KR); Hyein Jeong, Yongin-si (KR); Soungwook Kim, Yongin-si (KR); Sungsoo Bae, Yongin-si (KR); Hyewon Choi, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 1254 days.

(21) Appl. No.: 17/674,845

(22) Filed: Feb. 18, 2022

(65) Prior Publication Data

US 2022/0278296 A1 Sep. 1, 2022

(30) Foreign Application Priority Data

Feb. 19, 2021 (KR) ........................ 10-2021-0022641

(51) Int. Cl.
*H10K 85/60* (2023.01)
*C07D 471/04* (2006.01)
(Continued)

(52) U.S. Cl.
CPC ......... *H10K 85/615* (2023.02); *C07D 471/04* (2013.01); *C07D 487/04* (2013.01);
(Continued)

(58) Field of Classification Search
CPC .. C07D 401/04; C07D 409/14; C07D 471/04; C07D 471/14; C07D 487/04;
(Continued)

(56) References Cited

U.S. PATENT DOCUMENTS

| | | | | |
|---|---|---|---|---|
| 9,954,182 B2 | 4/2018 | Zoellner | | |
| 2002/0055015 A1 * | 5/2002 | Sato | H10K 50/82 313/506 |

(Continued)

FOREIGN PATENT DOCUMENTS

| | | |
|---|---|---|
| CN | 110903159 | 3/2020 |
| KR | 10-2016-0102528 A | 8/2016 |
| KR | 20180075128 | 7/2018 |

OTHER PUBLICATIONS

Huang, Qiang, et al. "Performance Improvement of Top-Emitting Organic Light-Emitting Diodes by an Organic Capping Layer: An Experimental Study." Journal of Applied Physics, vol. 100, No. 6, 2006, p. 064507.

*Primary Examiner* — Elizabeth M. Dahlburg
(74) *Attorney, Agent, or Firm* — Womble Bond Dickinson (US) LLP

(57) ABSTRACT

Provided are a light-emitting device and an electronic apparatus including the same. The light-emitting device includes: a first electrode; a second electrode facing the first electrode; an interlayer located between the first electrode and the second electrode; and an electron transport capping layer located outside the second electrode, wherein the interlayer includes an emission layer and an electron transport region, one of the electron transport region and the electron transport capping layer includes a first compound represented by
(Continued)

Formula 1, and the other one includes the first compound, a second compound represented by Formula 2, or a combination thereof, and the electron transport region further includes a metal dopant:

Formula 1

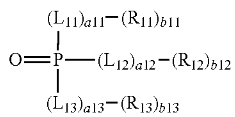

Formula 2

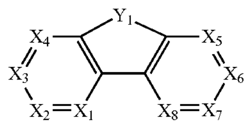

wherein, Formulae 1 and 2 are the same as described in the specification.

17 Claims, 3 Drawing Sheets

(51) Int. Cl.

| | |
|---|---|
| ***C07D 487/04*** | (2006.01) |
| ***C07D 491/048*** | (2006.01) |
| ***C07D 519/00*** | (2006.01) |
| ***C07F 9/547*** | (2006.01) |
| ***C07F 9/576*** | (2006.01) |
| ***C07F 9/58*** | (2006.01) |
| ***C07F 9/655*** | (2006.01) |
| ***C07F 9/6553*** | (2006.01) |
| ***C07F 9/6564*** | (2006.01) |
| ***H10K 50/16*** | (2023.01) |
| ***H10K 50/165*** | (2023.01) |
| *H10K 59/12* | (2023.01) |
| *H10K 59/80* | (2023.01) |

(52) U.S. Cl.

CPC ....... *C07D 491/048* (2013.01); *C07D 519/00* (2013.01); *C07F 9/547* (2013.01); *C07F 9/5765* (2013.01); *C07F 9/58* (2013.01); *C07F 9/65517* (2013.01); *C07F 9/655354* (2013.01); *C07F 9/6564* (2013.01); *H10K 50/165* (2023.02); *H10K 50/166* (2023.02); *H10K 85/649* (2023.02); *H10K 85/657* (2023.02); *H10K 85/6572* (2023.02); *H10K 85/6574* (2023.02); *H10K 59/12* (2023.02); *H10K 59/8052* (2023.02); *H10K 59/875* (2023.02)

(58) Field of Classification Search

CPC .. C07D 491/048; C07D 519/00; H10K 50/11; H10K 50/15; H10K 50/16; H10K 50/165; H10K 50/166; H10K 59/12; H10K 59/8052; H10K 59/875; H10K 85/615; H10K 85/622; H10K 85/623; H10K 85/624; H10K 85/626; H10K 85/649; H10K 85/654; H10K 85/657; H10K 85/6572; H10K 85/6574; H10K 85/6576

See application file for complete search history.

(56) References Cited

U.S. PATENT DOCUMENTS

| | | | | |
|---|---|---|---|---|
| 2005/0116291 | A1* | 6/2005 | Koo ..................... | H10K 59/124 438/149 |
| 2016/0336516 | A1 | 11/2016 | Zöllner | |
| 2018/0190922 | A1 | 7/2018 | Goelfert et al. | |
| 2018/0301638 | A1* | 10/2018 | Ahn ..................... | H10K 85/656 |
| 2019/0202848 | A1 | 7/2019 | Frey | |
| 2021/0202842 | A1* | 7/2021 | Fadhel ................ | C07F 9/65522 |

* cited by examiner

LIGHT-EMITTING DEVICE AND ELECTRONIC APPARATUS INCLUDING THE SAME

CROSS-REFERENCE TO RELATED APPLICATION

This application is based on and claims priority under 35 U.S.C. § 119 to Korean Patent Application No. 10-2021-0022641, filed on Feb. 19, 2021, in the Korean Intellectual Property Office, the disclosure of which is incorporated by reference herein in its entirety.

BACKGROUND

Field

One or more embodiments relate to a light-emitting device and an electronic apparatus including the same.

Discussion of the Background

Organic light-emitting devices (OLEDs) are self-emissive devices that, as compared with devices of the related art, have wide viewing angles, high contrast ratios, short response times, and excellent characteristics in terms of luminance, driving voltage, and response speed, and produce full-color images.

Organic light-emitting devices may include a first electrode located on a substrate, and a hole transport region, an emission layer, an electron transport region, and a second electrode sequentially stacked on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit from an excited state to a ground state, thereby generating light.

SUMMARY

One or more embodiments relate to a light-emitting device with low driving voltage and improved efficiency and lifespan characteristics, and an electronic apparatus including the same.

Additional aspects will be set forth in part in the description, which follows and, in part, will be apparent from the description, or may be learned by practice of the presented embodiments of the disclosure.

According to one or more embodiments, a light-emitting device according to an embodiment includes a first electrode, a second electrode facing the first electrode, an interlayer located between the first electrode and the second electrode, and an electron transport capping layer located outside the second electrode,

- the interlayer includes an emission layer and an electron transport region,
- one of the electron transport region and the electron transport capping layer includes a first compound represented by Formula 1, and the other one includes the first compound, a second compound represented by Formula 2, or a combination thereof, and
- the electron transport region may further include a metal dopant.

According to one or more embodiments, an electronic apparatus includes the light-emitting device.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
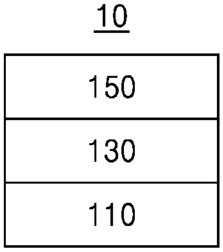
FIG. 1 is a diagram schematically showing the structure of a light-emitting device according to an embodiment.

Reference will now be made in detail to embodiments, examples of which are illustrated in the accompanying drawings, wherein like reference numerals refer to like elements throughout the specification. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Throughout the disclosure, the expression "at least one of a, b or c" indicates only a, only b, only c, both a and b, both a and c, both b and c, all of a, b, and c, or variations thereof.

Because the disclosure may have diverse modified embodiments, embodiments are illustrated in the drawings and are described in the detailed description. An effect and a characteristic of the disclosure, and a method of accomplishing these will be apparent when referring to embodiments described with reference to the drawings. The disclosure may, however, be embodied in many different forms and should not be construed as limited to the embodiments set forth herein.

Hereinafter, embodiments of the present disclosure will be described in detail with reference to the accompanying drawings. The same or corresponding components will be denoted by the same reference numerals, and thus redundant description thereof will be omitted.

It will be understood that although the terms "first," "second," etc. may be used herein to describe various components, these components should not be limited by these terms. These components are only used to distinguish one component from another.

An expression used in the singular encompasses the expression of the plural, unless it has a clearly different meaning in the context.

It will be further understood that the terms "comprises" and/or "comprising" used herein specify the presence of stated features or elements, but do not preclude the presence or addition of one or more other features or elements.

Sizes of elements in the drawings may be exaggerated for convenience of explanation. In other words, because sizes and thicknesses of components in the drawings are arbitrarily illustrated for convenience of explanation, the following embodiments are not limited thereto.

When a certain embodiment is implemented differently, a specific process order may be performed differently from the described order. For example, two processes described in succession may be performed substantially simultaneously, or may be performed in an order opposite to the described order.

It will be understood that when a layer, region, or component is referred to as being "connected to" another layer, region, or component, the layer, region, or component may be directly connected to the another layer, region, or component, or indirectly connected to the another layer, region, or component as intervening layer, region, or component is present. For example, it will be understood that when a layer, region, or component is referred to as being "electrically connected to" another layer, region, or component, the layer, region, or component may be directly electrically connected to the another layer, region, or component, or indirectly electrically connected to the another layer, region, or component as interventing layer, region, or component is present.

The term "interlayer" as used herein refers to a single layer and/or all layers between a first electrode and a second electrode of a light-emitting device.

According to one or more embodiments, a light-emitting device according to an embodiment includes: a first electrode; a second electrode facing the first electrode; an interlayer located between the first electrode and the second electrode; and an electron transport capping layer located outside the second electrode.

The interlayer may include an emission layer and an electron transport region.

In an embodiment, the electron transport region may be located between the emission layer and the second electrode.

One of the electron transport region and the electron transport capping layer includes a first compound represented by Formula 1, and the other one includes the first compound, a second compound represented by Formula 2, or a combination thereof:

Formula 1

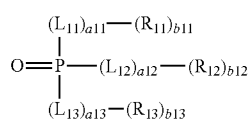

Formula 2

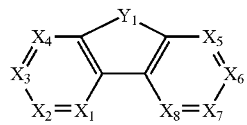

wherein, in Formula 1 and Formula 2, $Y_1$ may be *—O—*', *—S—*', *—N[$(L_9)_{a9}$-$(R_9)_{b9}$]—*', *—C[$(L_9)_{a9}$-$(R_9)_{b9}$][$(L_{10})_{a10}$-$(R_{10})_{b10}$]—*', *—C[$(L_9)_{a9}$-$(R_9)_{b9}$]=C[$(L_{10})_{a10}$-$(R_{10})_{b10}$]—*', *—C[$(L_9)_{a9}$-$(R_9)_{b9}$]=N—*', or *—N=C[$(L_{10})_{a10}$-$(R_{10})_{b10}$]—*', $X_1$ may be N or C[$(L_1)_{a1}$-$(R_1)_{b1}$], $X_2$ may be N or C[$(L_2)_{a2}$-$(R_2)_{b2}$], $X_3$ may be N or C[$(L_3)_{a3}$-$(R_3)_{b3}$], $X_4$ may be N or C[$(L_4)_{a4}$-$(R_4)_{b4}$], $X_5$ may be N or C[$(L_5)_{a5}$-$(R_5)_{b5}$], $X_6$ may be N or C[$(L_6)_{a6}$-$(R_6)_{b6}$], $X_7$ may be N or C[$(L_7)_{a7}$-$(R_7)_{b7}$], and $X_8$ may be N or C[$(L_8)_{a8}$-$(R_8)_{b8}$], $L_1$ to $L_{13}$ may each independently be a single bond, a $C_1$-$C_{20}$ alkylene group that is unsubstituted or substituted with at least one $R_{10a}$, a $C_2$-$C_{20}$ alkenylene group that is unsubstituted or substituted with at least one $R_{10a}$, a $C_2$-$C_{20}$ alkynylene group that is unsubstituted or substituted with at least one $R_{10a}$, a $C_3$-$C_{10}$ cycloalkylene group that is unsubstituted or substituted with at least one $R_{10a}$, a $C_1$-$C_{10}$ heterocycloalkylene group that is unsubstituted or substituted with at least one $R_{10a}$, a $C_3$-$C_{10}$ cycloalkenylene group that is unsubstituted or substituted with at least one $R_{10a}$, a $C_1$-$C_{10}$ heterocycloalkenylene group that is unsubstituted or substituted with at least one $R_{10a}$, a $C_1$-$C_{60}$ arylene group that is unsubstituted or substituted with at least one $R_{10a}$, a $C_1$-$C_{60}$ heteroarylene group that is unsubstituted or substituted with at least one $R_{10a}$, a divalent non-aromatic condensed polycyclic group that is unsubstituted or substituted with at least one $R_{10a}$, or a divalent non-aromatic condensed heteropolycyclic group that is unsubstituted or substituted with at least one $R_{10a}$, a1 to a13 may each independently be 0, 1, 2, 3, 4, or 5, $R_1$ to $R_{13}$ may each independently be hydrogen, deuterium, —F, —Cl, —Br, —I, a hydroxyl group, a cyano group, a nitro group, an amidino group, a hydrazino group, a hydrazono group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a $C_1$-$C_{60}$ heteroaryloxy group unsubstituted or substituted with at least one $R_{10a}$, a $C_1$-$C_{60}$ heteroarylthio group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), neighboring two or more of $R_1$ to $R_{10}$ may optionally be linked to each other to form a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, neighboring two or more of $R_{11}$ to $R_{13}$ may optionally be linked to each other to form a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, b1 to b13 may each independently be 1, 2, 3, 4, 5, 6, 7, or 8,

* and *' each indicate a binding site to a neighboring atom, and $R_{10a}$ may be:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), —P(=O)($Q_{11}$)($Q_{12}$), or any combination thereof, a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof, or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, a $C_7$-$C_{60}$ aryl alkyl group; or a $C_2$-$C_{60}$ heteroaryl alkyl group.

Due to the inclusion of the electron transport layer and the electron transport capping layer, the driving voltage may be lowered and the efficiency and lifespan characteristics may be improved.

In an embodiment, the first compound and the second compound may have a structure capable of bonding with metal atoms. Accordingly, since the electron transport layer includes the first compound and/or the second compound and a metal dopant, an ohmic contact may be implemented, and thus, electrons may be easily injected or transported from the second electrode. In addition, since the electron transport capping layer includes the first compound and/or the second compound, aggregation or swelling of metal constituting the second electrode may be prevented to improve the durability thereof.

In an embodiment, in Formulae 1 and 2, at least one of $X_1$ to $X_8$ is N; or at least one of $L_1$ to $L_{13}$ and $R_1$ to $R_{13}$ may include a π electron deficient nitrogen-containing ring.

In an embodiment, $L_1$ to $L_{13}$ in Formulae 1 and 2 may each independently be selected from: a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a spiro-fluorene-benzofluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a spiro-fluorene-benzofluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolylene group, a benzocarbazolyl group, a dibenzocarbazolyl group, a thiadiazolyl group, an imidazopyridinyl group, an imidazopyrimidinyl group, $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, and $-P(=O)(Q_{31})(Q_{32})$, wherein $Q_{31}$ to $Q_{33}$ may each independently be selected from a $C_1$-$C_{10}$ alkyl group, a $C_1$-$C_{10}$ alkoxy group, a phenyl group, a phenyl group substituted with a $C_1$-$C_{10}$ alkyl group, a biphenyl group, a terphenyl group, a naphthyl group, a pyridinyl group, a pyrimidyl group, a triazinyl group, a quinolinyl group, and an isoquinolinyl group.

In an embodiment, $L_1$ to $L_{13}$ may each independently be a group represented by one of Formulae 3-1 to 3-26:

3-1

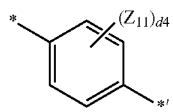

3-2

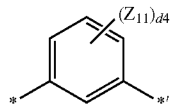

3-3

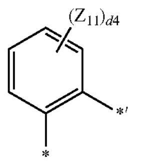

3-4

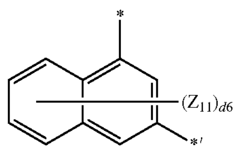

-continued 3-5

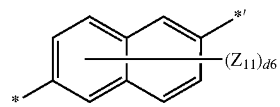

3-6

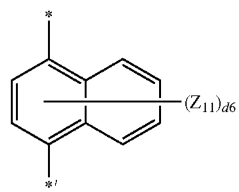

3-7

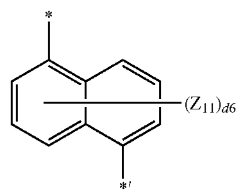

3-8

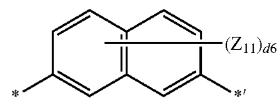

3-9

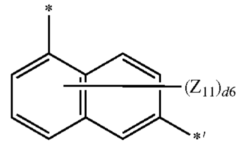

3-10

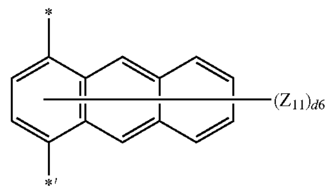

3-11

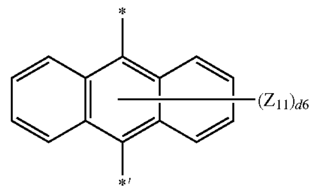

3-12

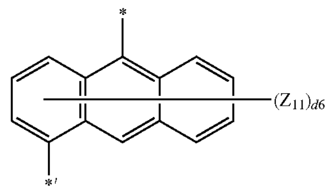

3-13

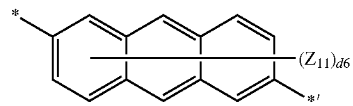

-continued
3-14
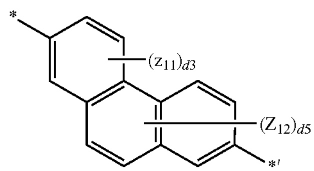
3-15
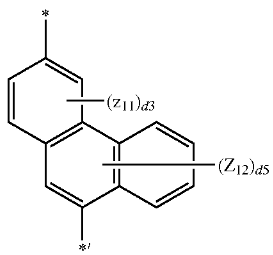
3-16
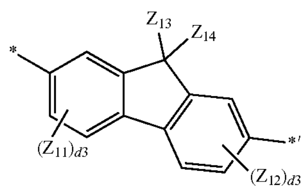
3-17
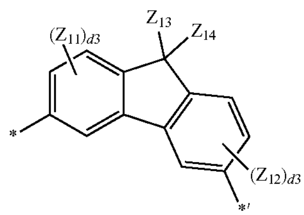
3-18
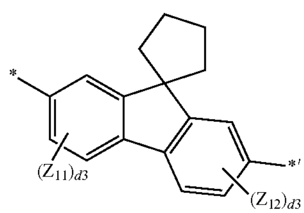
3-19
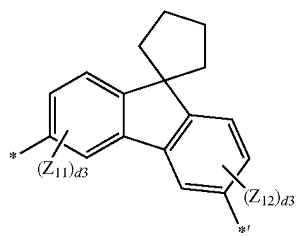
3-20
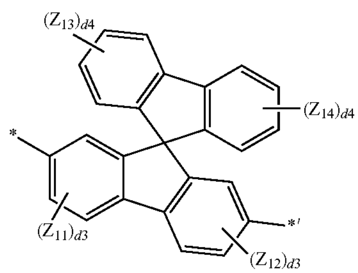
-continued
3-21
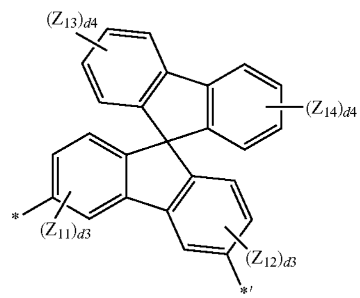
3-22
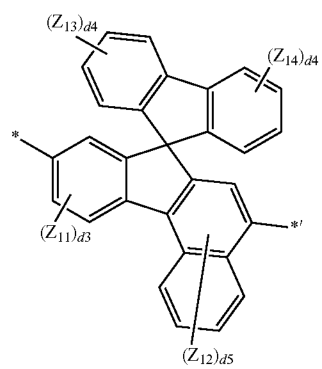
3-23
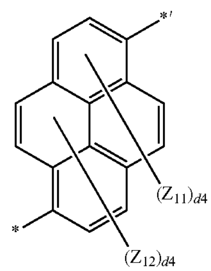
3-24
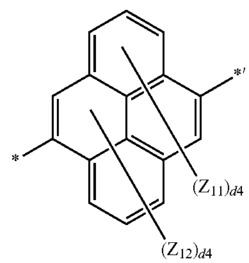
3-25
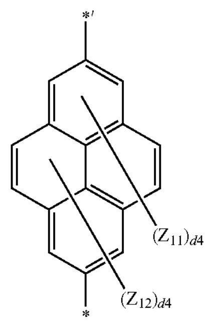

-continued 3-26

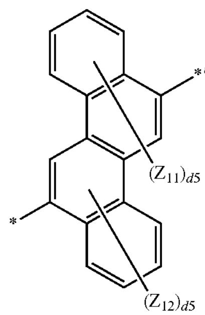

wherein, in formulae 3-1 to 3-26, $Z_{11}$ to $Z_{14}$ may each independently be selected from hydrogen, deuterium, —F, —Cl, —Br, —I, a hydroxyl group, a cyano group, a nitro group, an amino group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a dibenzofuranyl group, a dibenzothiophenyl group, a triazinyl group, a benzimidazolyl group, a phenanthrolinyl group, and —Si($Q_{31}$)($Q_{32}$)($Q_{33}$), $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, d3 may be an integer from 0 to 3, d4 may be an integer from 0 to 4, d5 may be an integer from 0 to 5, d6 may be an integer from 0 to 6, d8 may be an integer from 0 to 8, and

* and *' each indicate a binding site to a neighboring atom.

In an embodiment, a1 to a13 in Formulae 1 and 2 may each independently be 0, 1, or 2.

For example, a1 to a13 may each independently be 0 or 1.

In an embodiment, $R_1$ to $R_{13}$ in Formulae 1 and 2 may each independently be:

hydrogen, deuterium, —F —Cl, —Br, —I, a hydroxyl group, or a cyano group;

a $C_1$-$C_{20}$ alkyl group, a $C_2$-$C_{20}$ alkenyl group, a $C_2$-$C_{20}$ alkynyl group, or a $C_1$-$C_{20}$ alkoxy group;

a $C_1$-$C_{20}$ alkyl group, a $C_2$-$C_{20}$ alkenyl group, a $C_2$-$C_{20}$ alkynyl group, or a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, —Si($Q_{31}$)($Q_{32}$)($Q_{33}$), —N($Q_{31}$)($Q_{32}$), —B($Q_{31}$)($Q_{32}$), —C(═O)($Q_{31}$), —S(═O)$_2$($Q_{31}$), and —P(═O)($Q_{31}$)($Q_{32}$);

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a pentalenyl group, an indenyl group, a naphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a pyrrolyl group, a furanyl group, a thiophenyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a benzimidazolyl group, a benzofuranyl group, a benzothiophenyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group; or a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a pentalenyl group, an indenyl group, a naphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a pyrrolyl group, a furanyl group, a thiophenyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a benzimidazolyl group, a benzofuranyl group, a benzothiophenyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a pentalenyl group, an indenyl group, a naphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a pyrrolyl group, a furanyl group, a thiophenyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a benzimidazolyl group, a benzofuranyl group, a benzothiophenyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, wherein $Q_{31}$ to $Q_{33}$ may each independently be selected from hydrogen, deuterium, —F, —Cl, —Br, —I, a cyano group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{20}$ aryl group, a $C_1$-$C_{20}$ heteroaryl group, a monovalent non-aromatic condensed polycyclic group, a monovalent non-aromatic condensed heteropolycyclic group, a biphenyl group, and a terphenyl group.

In an embodiment, $R_1$ to $R_{13}$ may each independently be: hydrogen, deuterium, —F —Cl, —Br, —I, a hydroxyl group, or a cyano group; a $C_1$-$C_{20}$ alkyl group or a $C_1$-$C_{20}$ alkoxy group, each substituted with at least one selected from deuterium, —F, —Cl, —Br, —I, a cyano group, a phenyl group, and a biphenyl group; or a group represented by any one selected from Formulae 5-1 to 5-26 and Formulae 6-1 to 6-55:

5-1

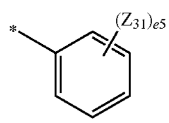

5-2

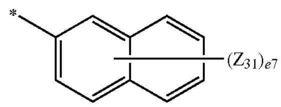

5-3

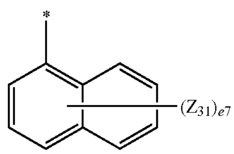

-continued 5-4

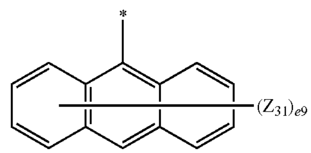

5-5

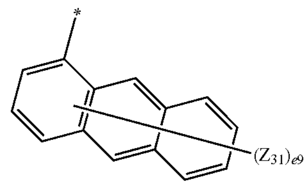

5-6

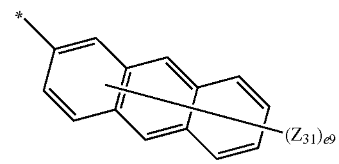

5-7

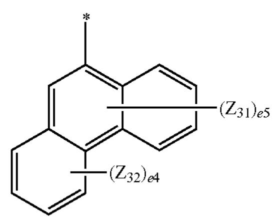

5-8

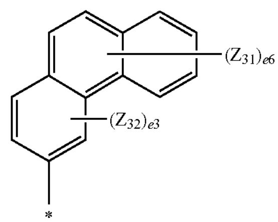

5-9

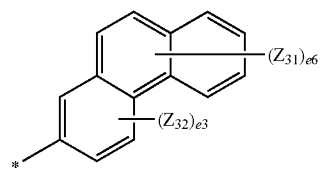

5-10

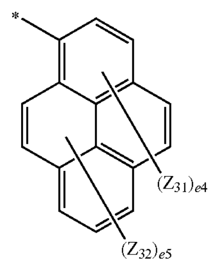

-continued
5-11
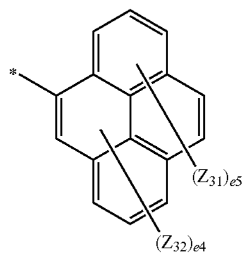
5-12
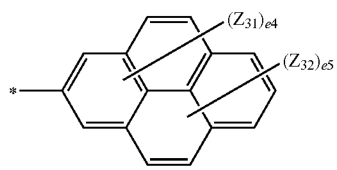
5-13
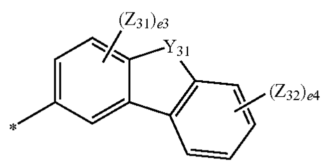
5-14
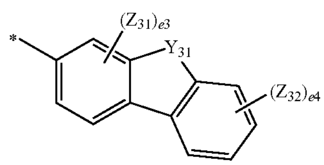
5-15
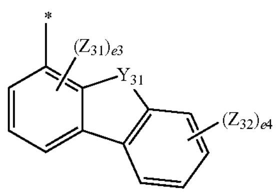
5-16
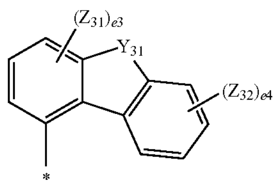
5-17
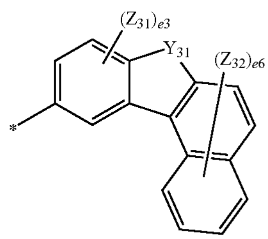
-continued
5-18
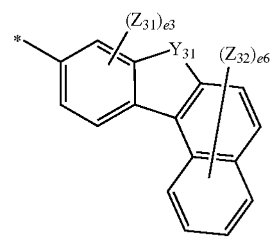
5-19
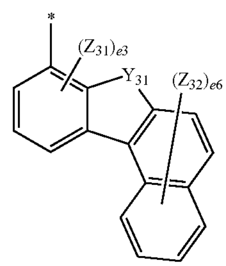
5-20
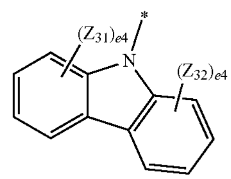
5-21
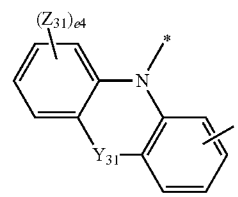
5-22
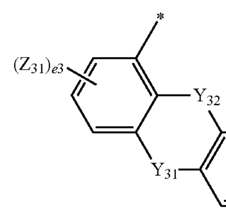
5-23
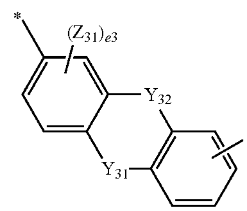
5-24
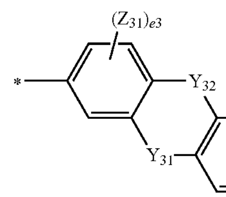

-continued
5-25
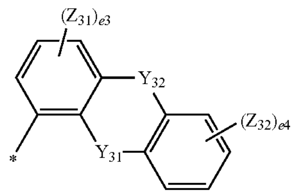
5-26
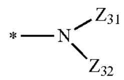
6-1
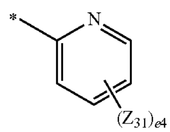
6-2
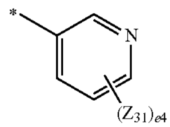
6-3
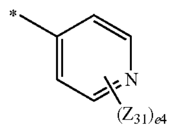
6-4
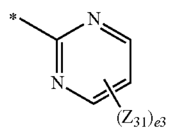
6-5
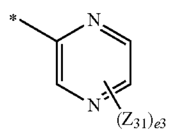
6-6
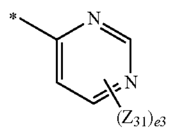
6-7
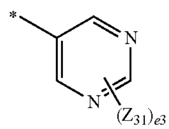
6-8
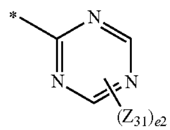
6-9
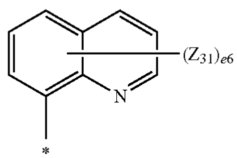
-continued
6-10
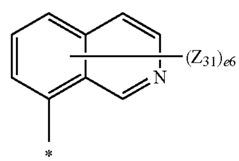
6-11
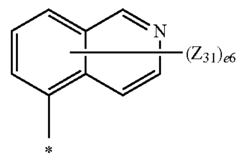
6-12
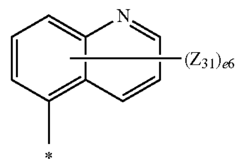
6-13
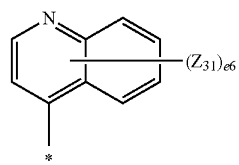
6-14
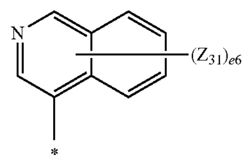
6-15
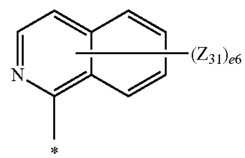
6-16
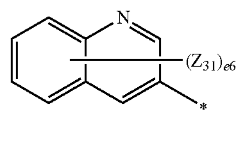
6-17
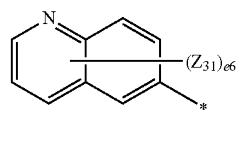
6-18
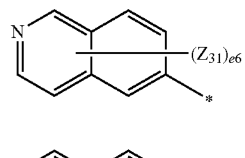
6-19
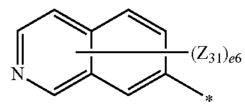

-continued
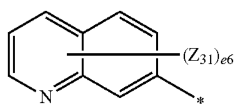
6-20
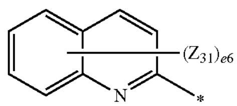
6-21
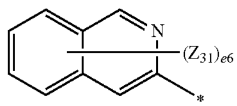
6-22
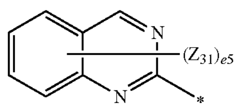
6-23
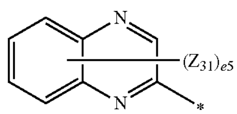
6-24
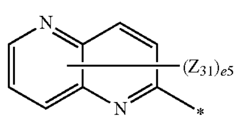
6-25
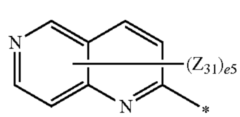
6-26
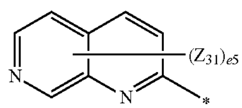
6-27
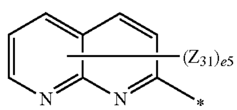
6-28
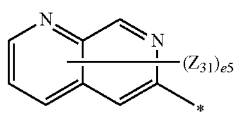
6-29
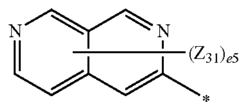
6-30
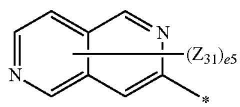
6-31
-continued
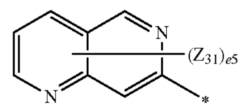
6-32
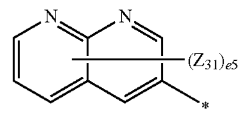
6-33
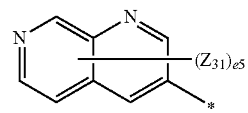
6-34
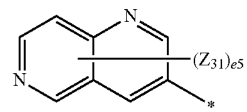
6-35
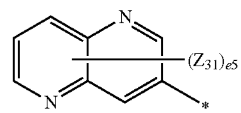
6-36
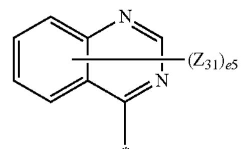
6-37
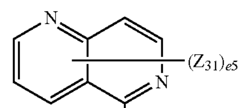
6-38
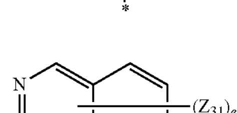
6-39
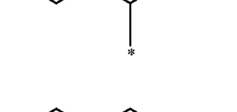
6-40
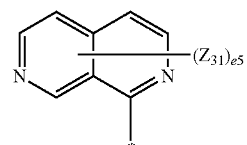
6-41
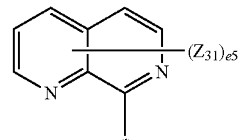

-continued 6-42

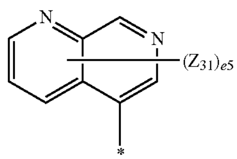

6-43

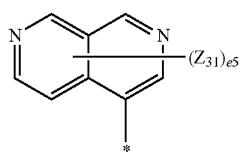

6-44

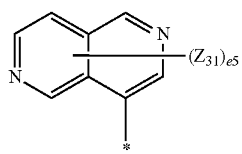

6-45

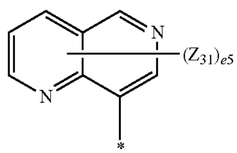

6-46

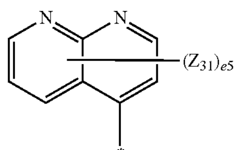

6-47

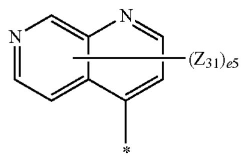

6-48

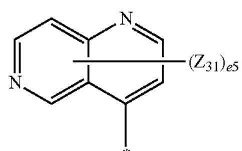

6-49

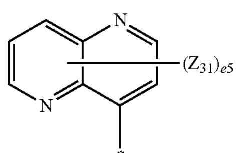

6-50

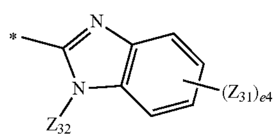

-continued 6-51

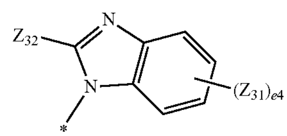

6-52

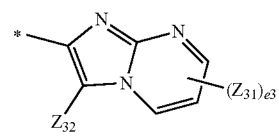

6-53

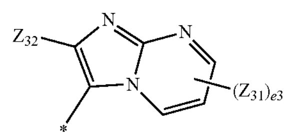

6-54

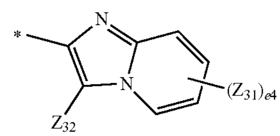

6-55

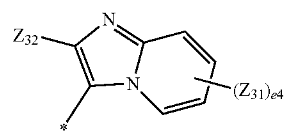

wherein, in Formulae 5-1 to 5-26 and 6-1 to 6-55, $Y_{31}$ and $Y_{32}$ may each independently be O, S, $C(Z_{33})(Z_{34})$, $N(Z_{33})$, or $Si(Z_{33})(Z_{34})$, $Z_{31}$ to $Z_{34}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group, a fluorenyl group, a spiro-bifluorenyl group, a phenanthrenyl group, an anthracenyl group, a triphenylenyl group, a pyridinyl group, a pyrimidinyl group, a carbazolyl group, and a triazinyl group, e2 may be 1 or 2, e3 may be an integer from 1 to 3, e4 may be an integer from 1 to 4, e5 may be an integer from 1 to 5, e6 may be an integer from 1 to 6, e7 may be an integer from 1 to 7, e9 may be an integer from 1 to 9, and

* indicates a binding site to a neighboring atom.

In an embodiment, b1 to b13 in Formulae 1 and 2 may each independently be 1, 2, 3, 4, 5, or 6.

For example, b1 to b13 may each independently be 1, 2, 3, or 4.

For example, b1 to b13 may each independently be 1 or 2.

In an embodiment, the first compound may be selected from Compounds 1-1 to 1-79:
1-1
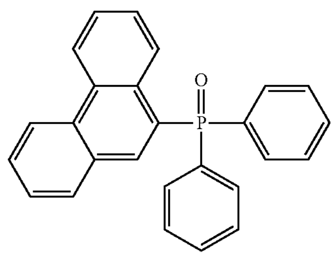
1-2
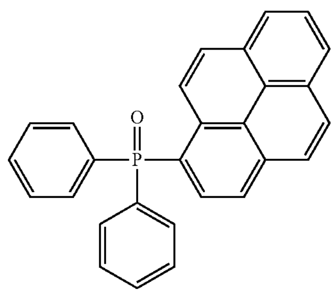
1-3
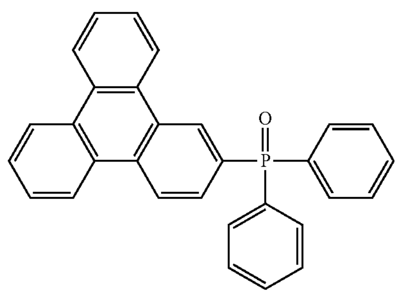
1-4
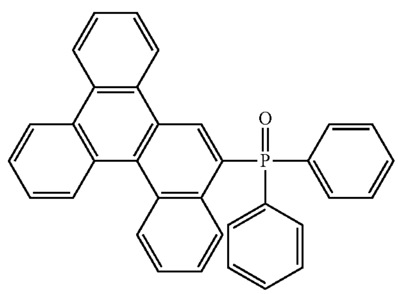
1-5
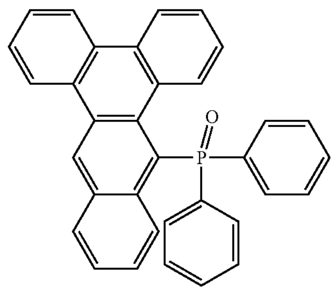
1-6
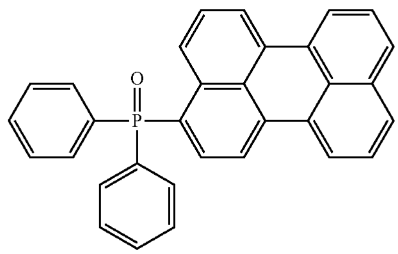
1-7
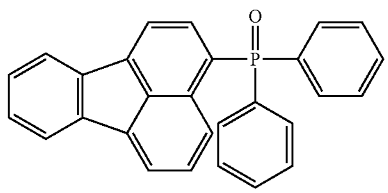
1-8
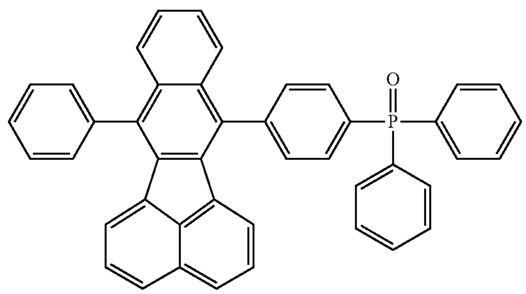
1-9
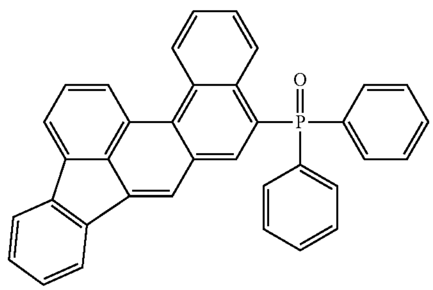
1-10
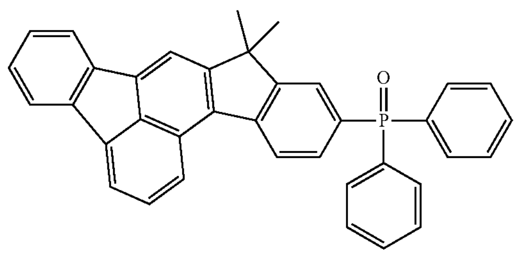

-continued
1-11
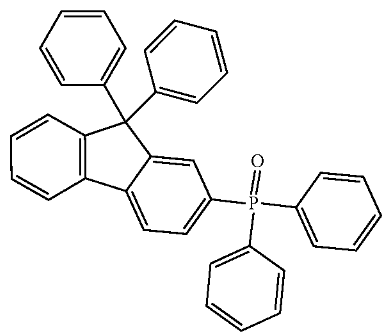
1-12
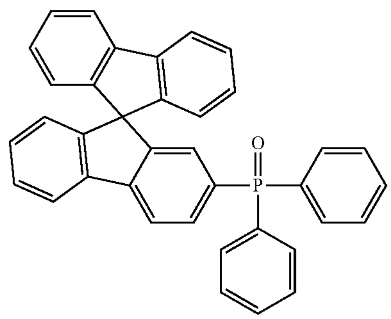
1-13
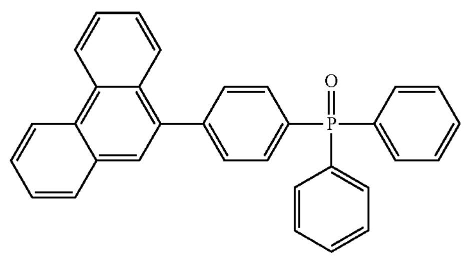
1-14
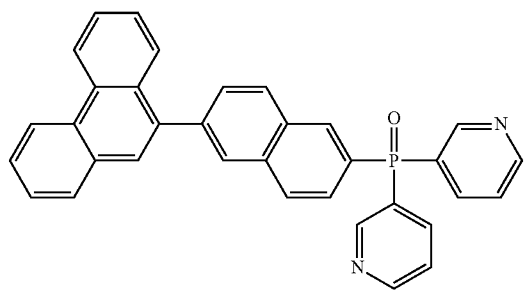
1-15
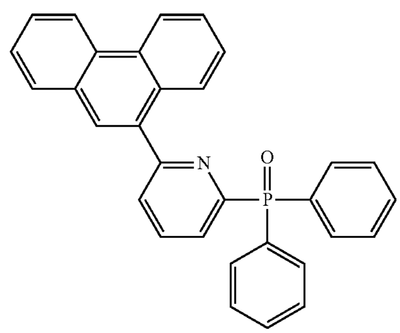
1-16
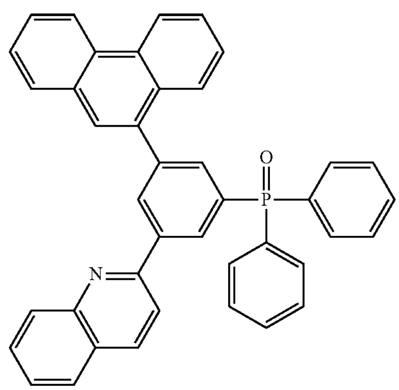
1-17
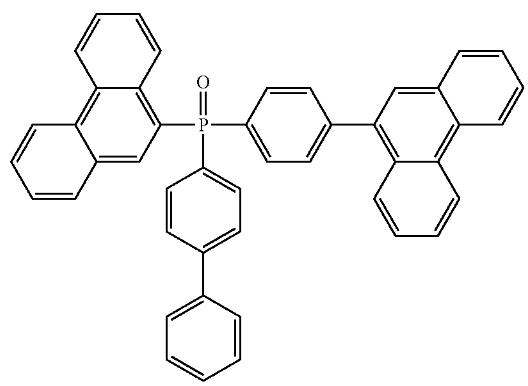
1-18
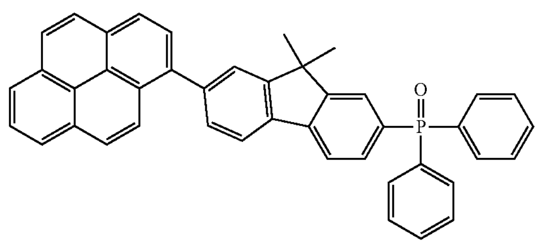

-continued
1-19
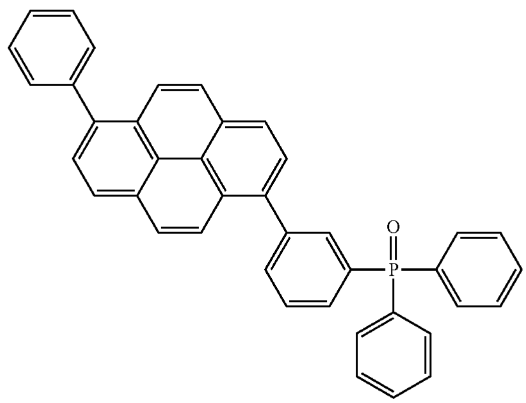
1-20
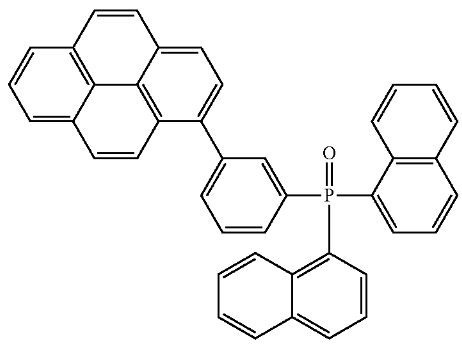
1-21
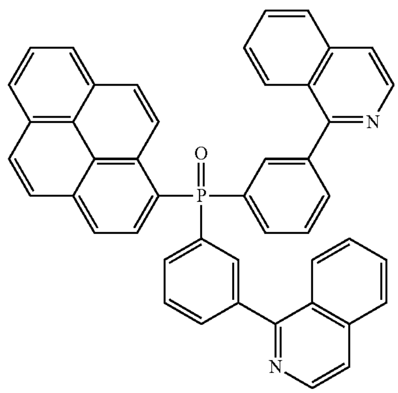
1-22
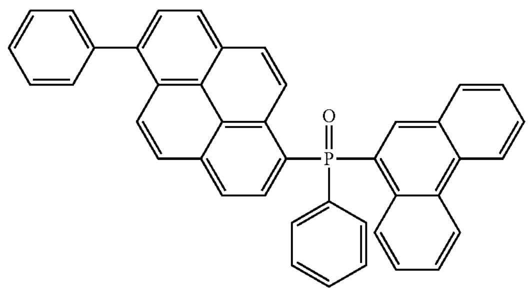
1-23
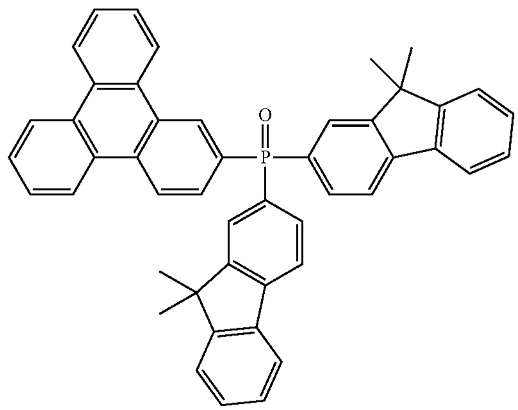
1-24
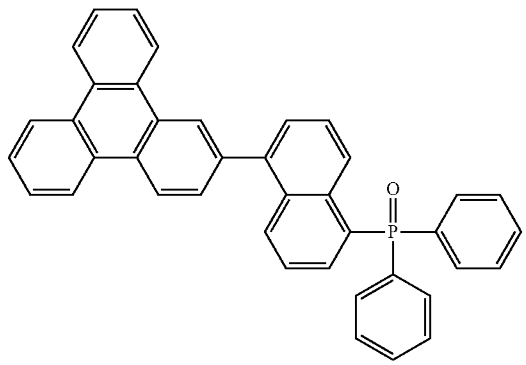
1-25
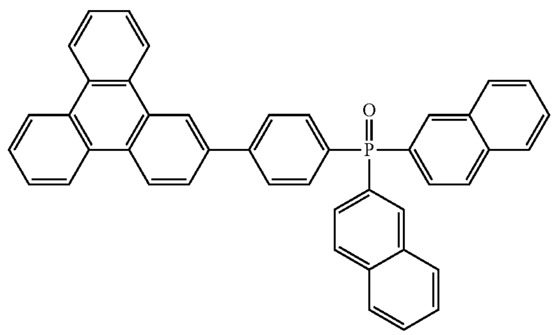
1-26
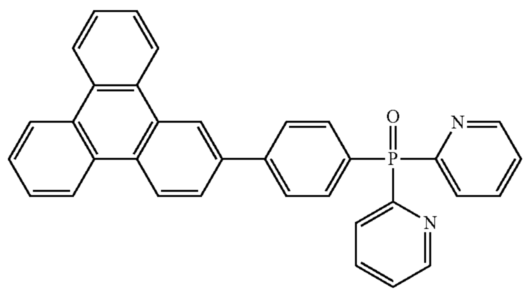

-continued
1-27
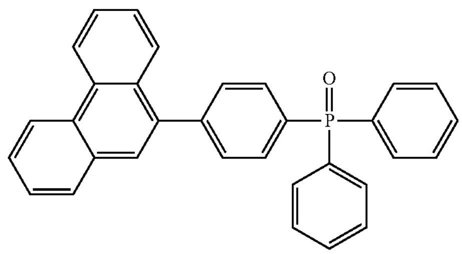
1-28
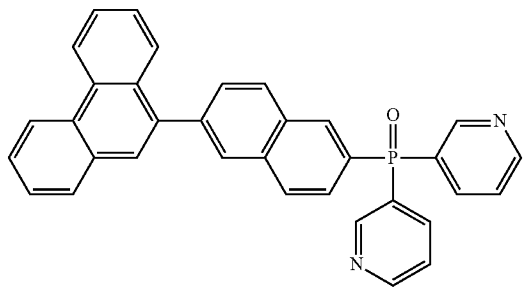
1-29
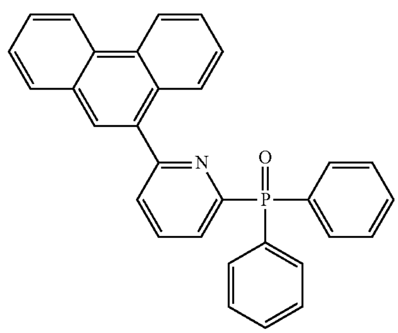
1-30
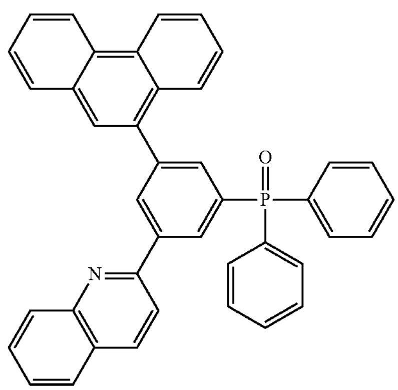
1-31
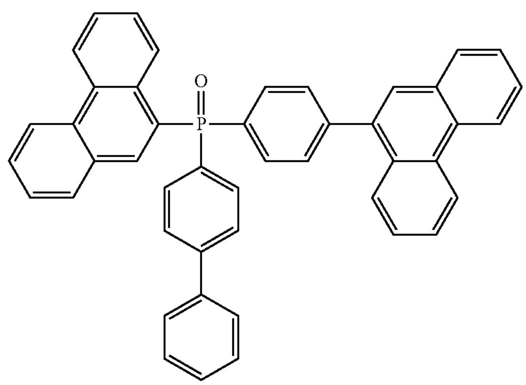
1-32
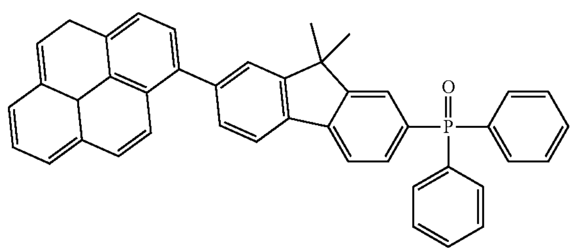
1-33
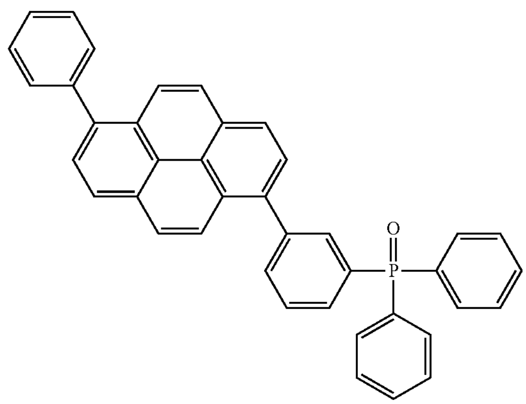
1-34
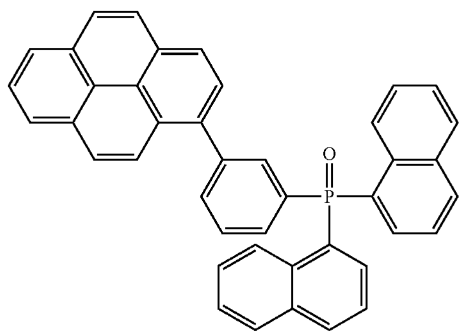

-continued
1-35
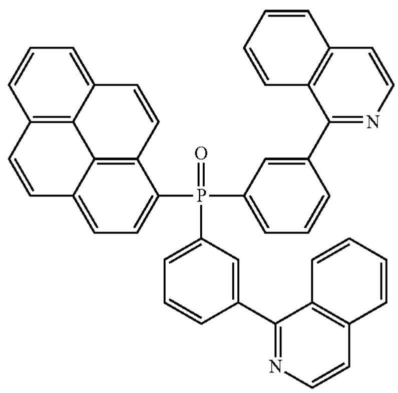
1-36
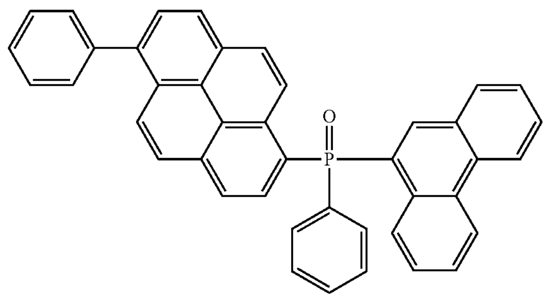
1-37
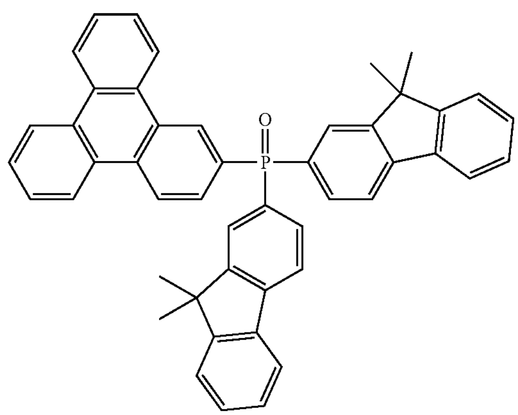
1-38
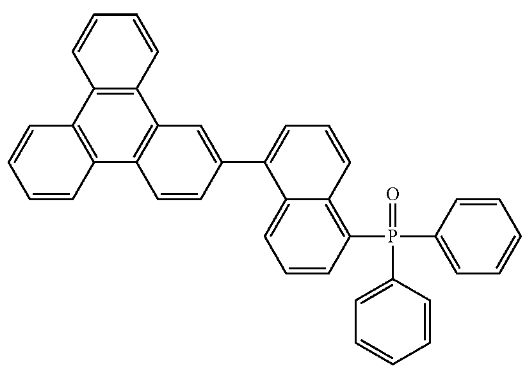
1-39
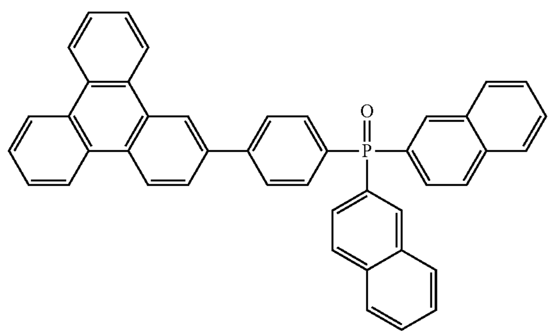
1-40
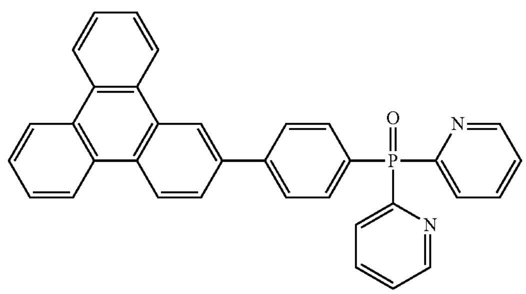
1-41
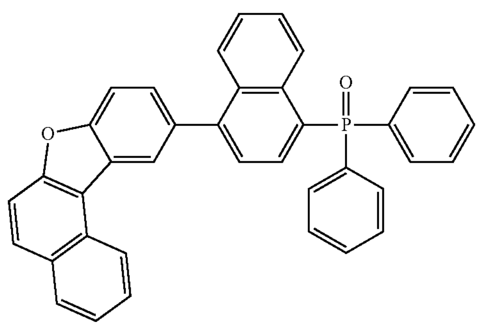
1-42
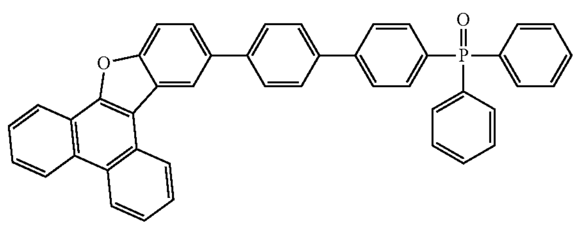

-continued
1-43
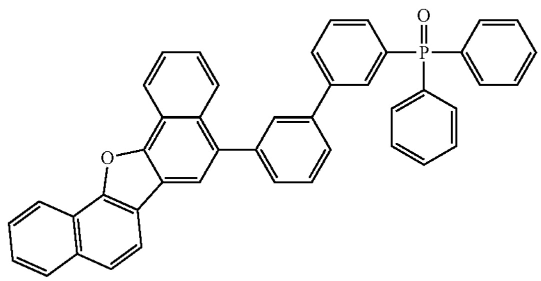
1-44
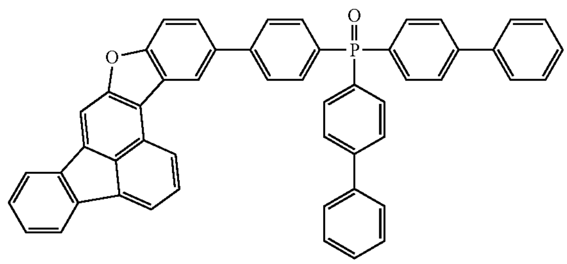
1-45
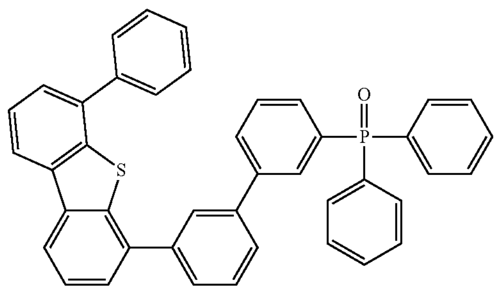
1-46
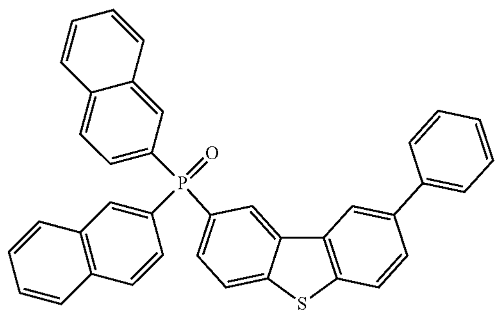
1-47
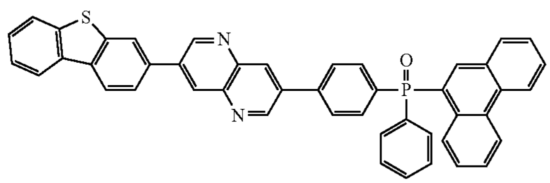
1-48
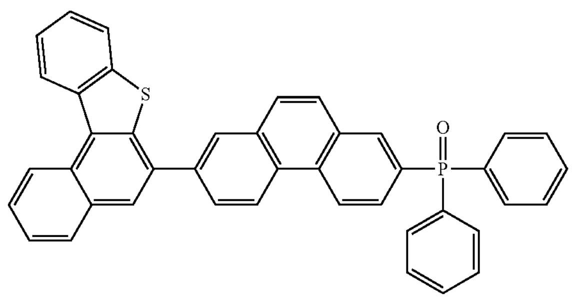
1-49
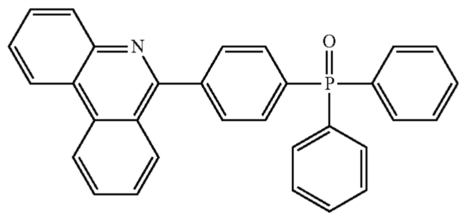
1-50
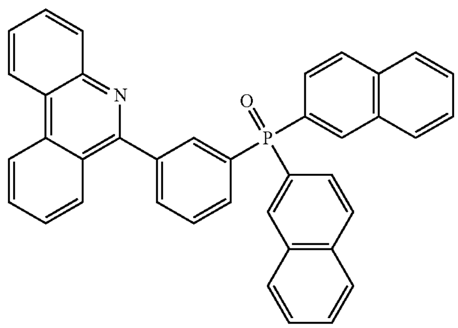
1-51
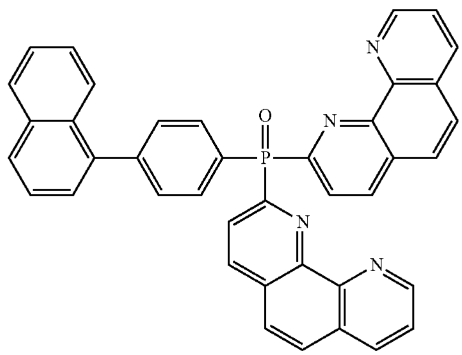
1-52
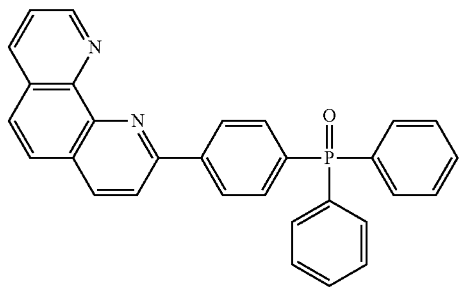

-continued
1-53
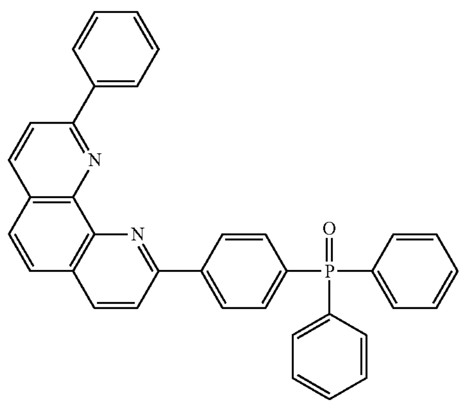
1-54
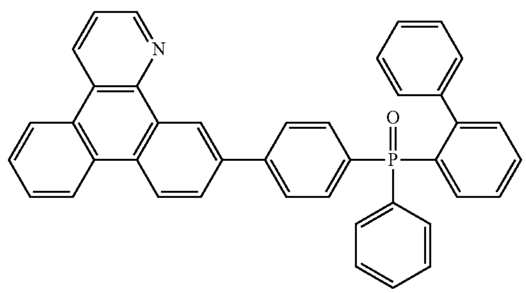
1-55
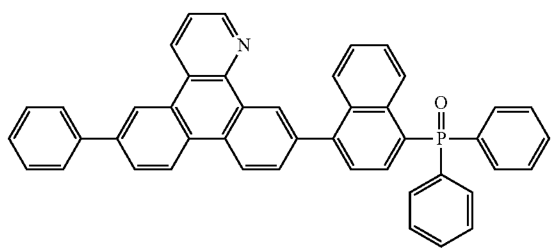
1-56
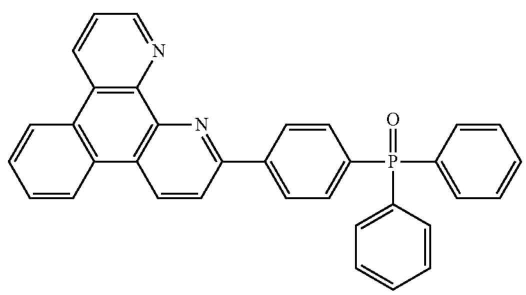
1-57
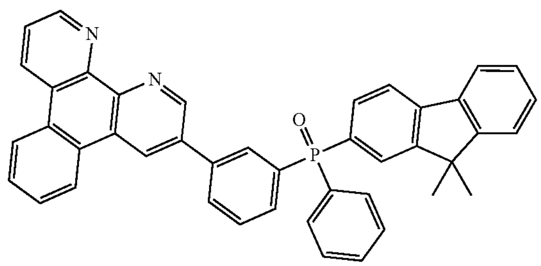
1-58
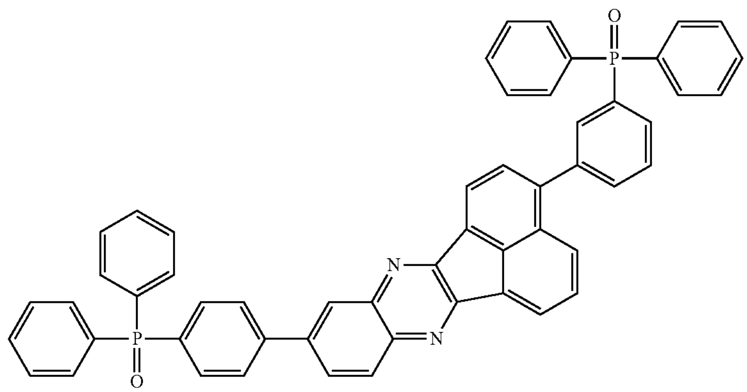

-continued
1-59
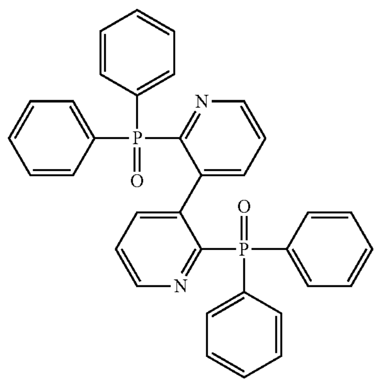
1-60
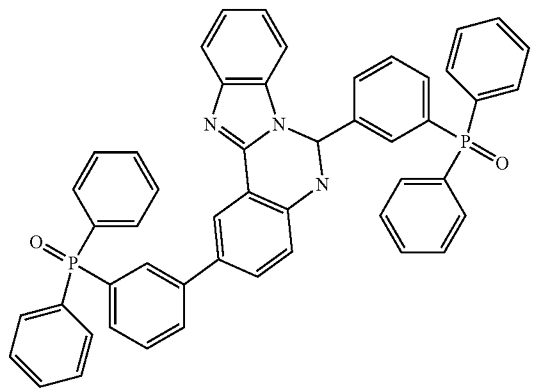
1-61
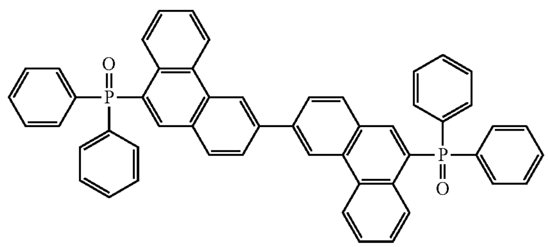
1-62
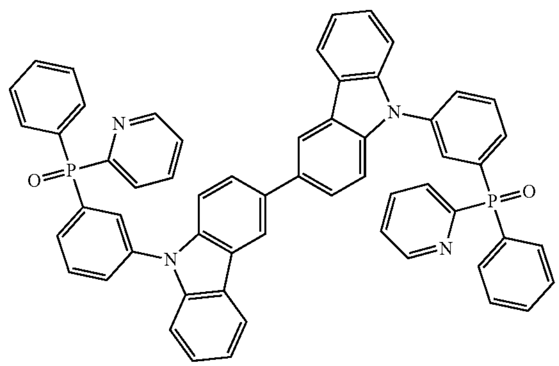
1-63
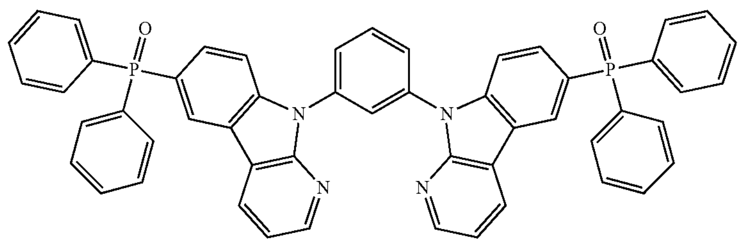
1-64
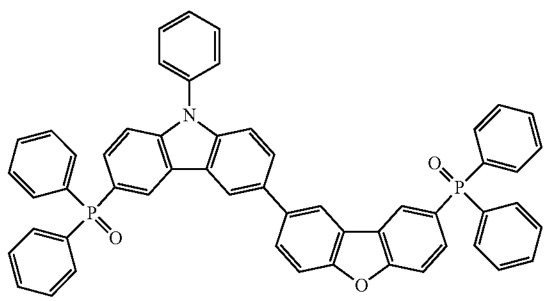
1-65
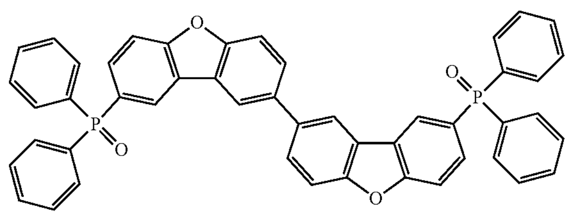

-continued
1-66
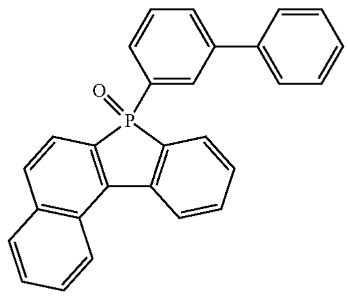
1-67
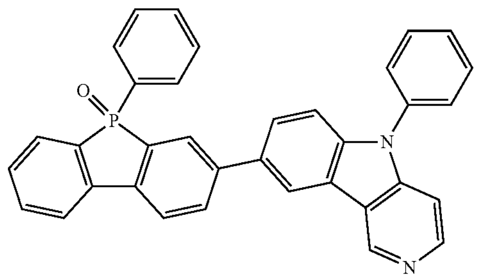
1-68
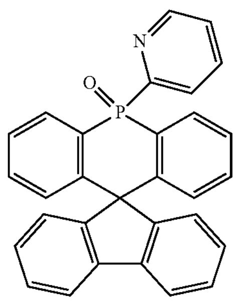
1-69
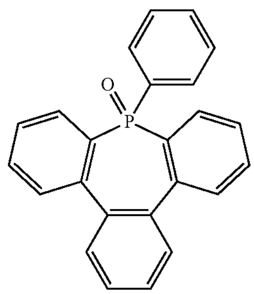
1-70
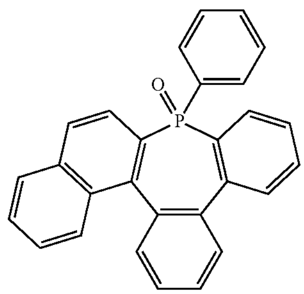
1-71
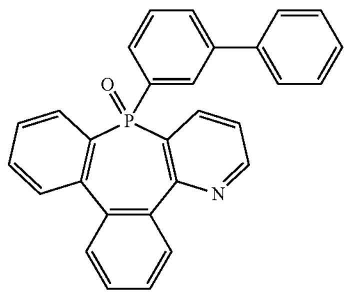
1-72
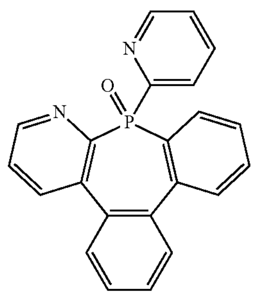
1-73
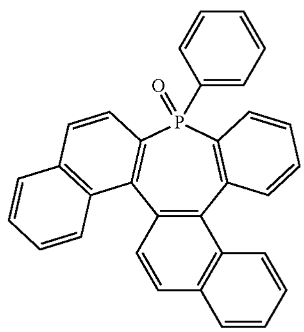
1-74
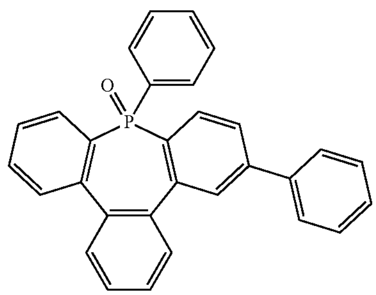
1-75
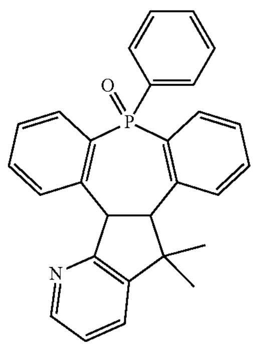

-continued
1-76
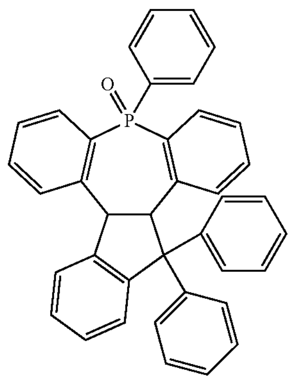
1-77
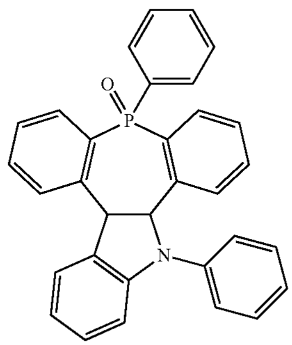
1-78
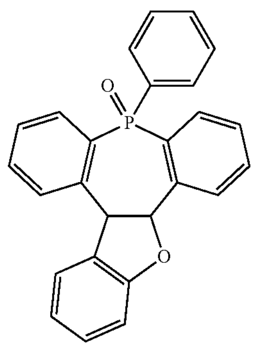
1-79
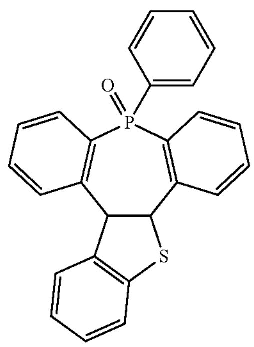
.
In an embodiment, the second compound may be selected from Compounds 2-1 to 2-18:
2-1
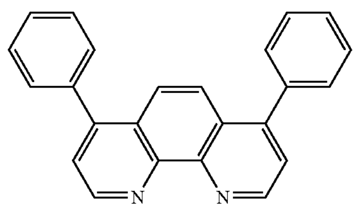
2-2
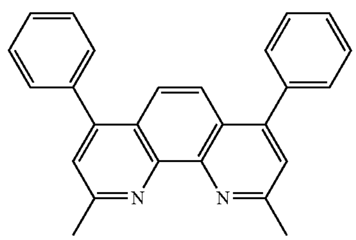
-continued
2-3
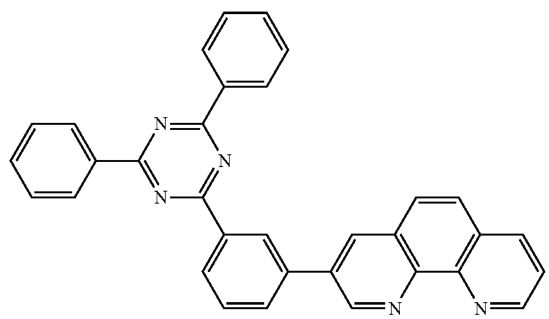
2-4
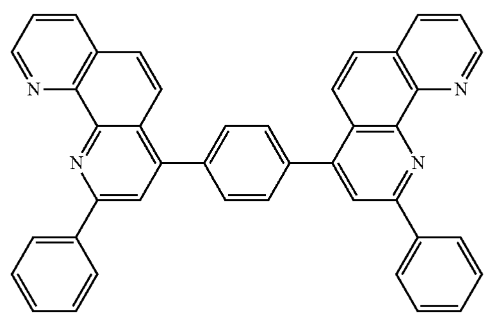

-continued
2-5
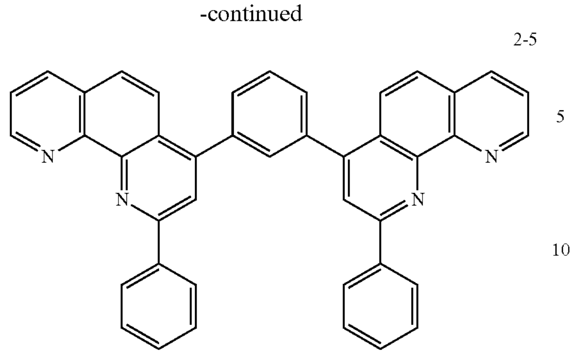
2-6
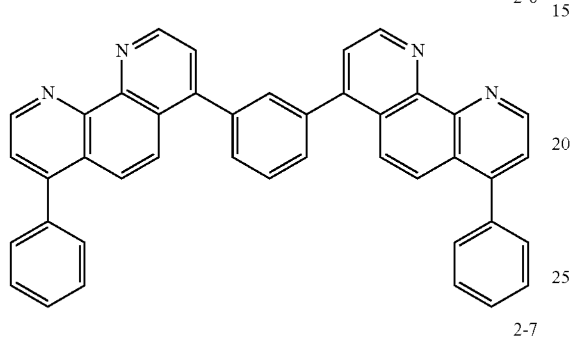
2-7
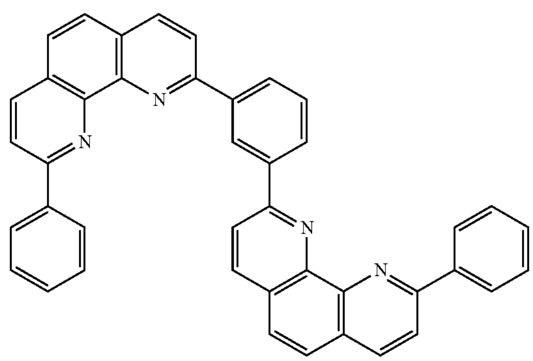
2-8
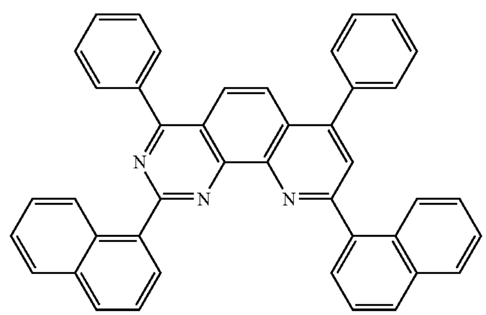
2-9
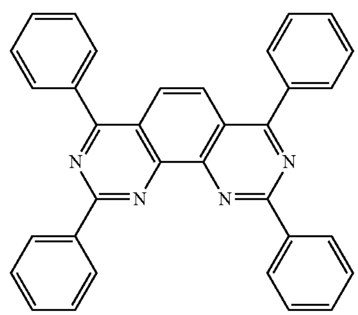
-continued
2-10
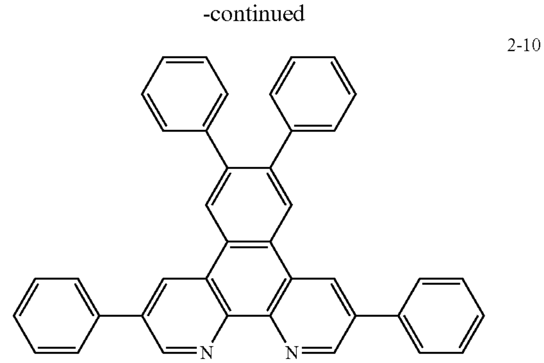
2-11
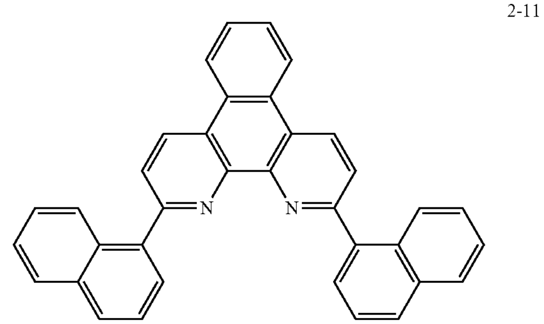
2-12
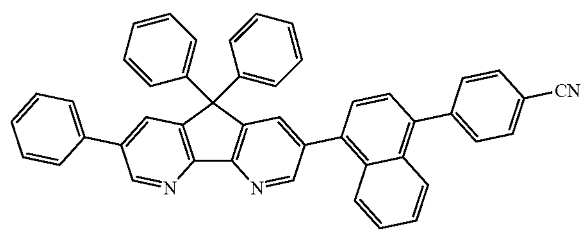
2-13
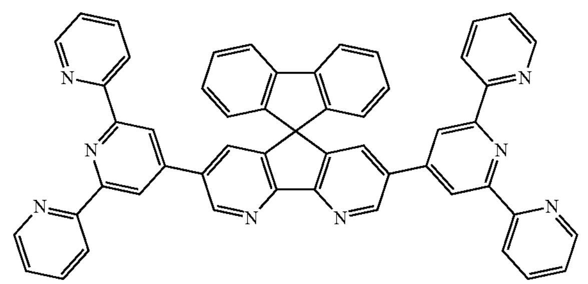
2-14
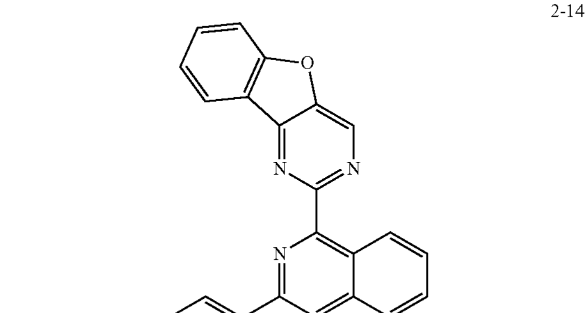
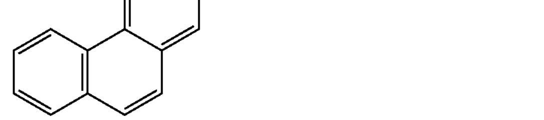

-continued 2-15

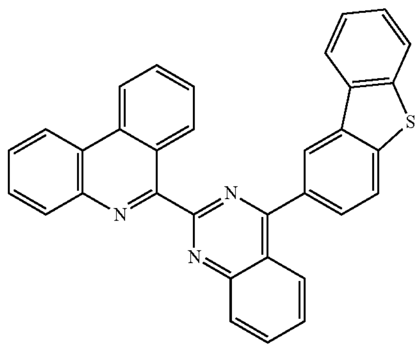

2-16

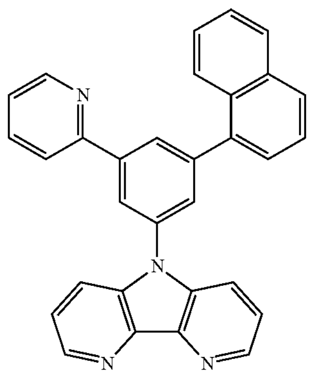

2-17

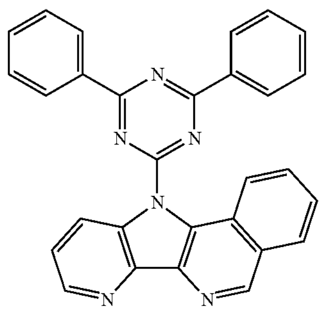

2-18

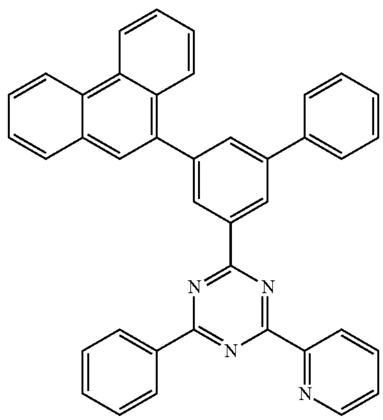

In an embodiment, the electron transport capping layer may include the first compound.

In an embodiment, the electron transport capping layer may include the second compound.

In an embodiment, the electron transport capping layer may include the first compound and the second compound.

In an embodiment, the electron transport capping layer may not include metal. In an embodiment, the electron transport capping layer may be an organic capping layer that consists of the first compound and/or the second compound.

In an embodiment, the electron transport capping layer may include the first compound, and the electron transport region may include the first compound and the metal dopant.

In an embodiment, the electron transport capping layer may include the first compound, and the electron transport region may include the second compound and the metal dopant.

In an embodiment, the electron transport capping layer may include the first compound, and the electron transport region may include the first compound, the second compound, and the metal dopant.

In an embodiment, the electron transport capping layer may include the second compound, and the electron transport region may include the first compound and the metal dopant.

In an embodiment, the electron transport capping layer may include the second compound, and the electron transport region may include the second compound and the metal dopant.

In an embodiment, the electron transport capping layer may include the second compound, and the electron transport region may include the first compound, the second compound, and the metal dopant.

In an embodiment, the electron transport region may include an electron transport layer, and the electron transport layer may include the first compound, the second compound, or a combination thereof; and the metal dopant.

In an embodiment, the electron transport layer may include the first compound and the metal dopant.

In an embodiment, the electron transport layer may include the second compound and the metal dopant.

In an embodiment, the electron transport layer may include the first compound, the second compound, and the metal dopant.

In an embodiment, the metal dopant may include alkali metal, alkaline earth metal, rare earth metal, or any combination thereof.

For example, the metal dopant may include Li, Na, K, Rb, Cs, Mg, Ca, Sr, Ba, Sc, Y, Ce, Tb, Yb, Gd, or a combination thereof.

In an embodiment, the metal dopant may be Li, Yb, or a combination thereof.

In an embodiment, the amount of the metal dopant in the electron transport layer may be 5 wt % or less. For example, the amount of the metal dopant in the electron transport layer may be 0 wt % or more and 5 wt % or less.

Since the electron transport layer includes the first compound and/or the second compound and the metal dopant, an ohmic contact may be implemented, and accordingly, electrons may be easily injected or transported from the second electrode.

In an embodiment, the electron transport region may further include a hole-blocking layer, an electron control layer, an electron injection layer or a combination thereof.

In an embodiment, the electron transport region may consist of the electron transport layer.

In an embodiment, the electron transport layer may be in direct contact with the second electrode.

In an embodiment, the electron transport layer may be in direct contact with the emission layer.

In an embodiment, the emission layer may include a host and a dopant.

In an embodiment, in the emission layer, the amount of the host may be greater than the amount of the dopant based on the weight.

In an embodiment, the dopant may include a phosphorescent dopant, a fluorescent dopant, a delayed fluorescence material, or a combination thereof.

In an embodiment, the light-emitting device may further include a hole transport region located between the first electrode and the emission layer.

In an embodiment, the hole transport region may further include a hole injection layer, a hole transport layer, an electron-blocking layer or a combination thereof.

In an embodiment, an amount of silver (Ag) in the second electrode may be 95 wt % or more. In an embodiment, the amount of silver in the second electrode may be 95 wt % or more and 100 wt % or less.

When the amount of silver in the second electrode satisfies the above-described range, the light absorption rate of the second electrode is reduced, so that the light extraction efficiency of the light-emitting device to the outside may be improved.

In an embodiment, the second electrode may further include magnesium (Mg). For example, the amount of the magnesium in the second electrode may be 5 wt % or less. For example, the amount of magnesium in the second electrode may be 0 wt % or more and 5 wt % or less.

Another aspect provides an electronic apparatus including the light-emitting device. The electronic apparatus may further include a thin-film transistor. In one or more embodiments, the electronic apparatus may further include a thin-film transistor including a source electrode and a drain electrode, and the first electrode of the light-emitting device may be electrically connected to the source electrode or the drain electrode. In an embodiment, the electronic apparatus may further include a color filter, a color conversion layer, a touch screen layer, a polarizing layer, or any combination thereof. More details on the electronic apparatus are the same as described in the present specification.

[Description of FIG. 1]

Figure 2:
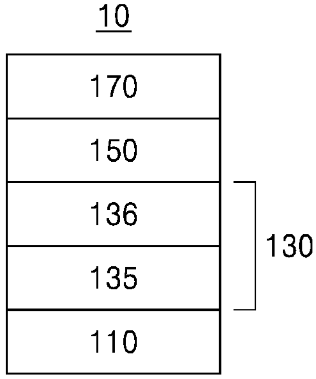
FIG. 2 is a diagram schematically showing the structure of a light-emitting device according to an embodiment.

FIGS. 1 and 2 are each a schematic cross-sectional view of a light-emitting device 10 according to an embodiment. The light-emitting device 10 includes a first electrode 110, an interlayer 130, a second electrode 150 and an electron transport capping layer 170. In an embodiment, the interlayer 130 of the light-emitting device 10 may include an emission layer 135 and an electron transport region 136.

Hereinafter, the structure of the light-emitting device 10 according to an embodiment and a method of manufacturing the light-emitting device 10 will be described in connection with FIGS. 1 and 2.

[First Electrode 110]

In FIG. 1, a substrate may be additionally located under the first electrode 110 or above the second electrode 150. As the substrate, a glass substrate or a plastic substrate may be used. In one or more embodiments, the substrate may be a flexible substrate, and may include plastics with excellent heat resistance and durability, such as polyimide, polyethylene terephthalate (PET), polycarbonate, polyethylene napthalate, polyarylate (PAR), polyetherimide, or any combination thereof.

The first electrode 110 may be formed by, for example, depositing or sputtering a material for forming the first electrode 110 on the substrate. When the first electrode 110 is an anode, a material for forming the first electrode 110 may be a high work function material that facilitates injection of holes.

The first electrode 110 may be a reflective electrode, a semi-transmissive electrode, or a transmissive electrode. When the first electrode 110 is a transmissive electrode, a material for forming the first electrode 110 may include indium tin oxide (ITO), indium zinc oxide (IZO), tin oxide ($SnO_2$), zinc oxide (ZnO), or any combinations thereof. In one or more embodiments, when the first electrode 110 is a semi-transmissive electrode or a reflective electrode, magnesium (Mg), silver (Ag), aluminum (Al), aluminum-lithium (Al—Li), calcium (Ca), magnesium-indium (Mg—In), magnesium-silver (Mg—Ag), or any combinations thereof may be used as a material for forming a first electrode.

The first electrode 110 may have a single layer consisting of a single-layered structure or a multilayer structure including a plurality of layers. For example, the first electrode 110 may have a three-layered structure of ITO/Ag/ITO.

[Interlayer 130]

The interlayer 130 may be located on the first electrode 110. The interlayer 130 may include the emission layer 135.

The interlayer 130 may further include a hole transport region placed between the first electrode 110 and the emission layer and an electron transport region placed between the emission layer and the second electrode 150.

The interlayer 130 may further include, in addition to various organic materials, metal-containing compounds such as organometallic compounds, inorganic materials such as quantum dots, and the like.

In one or more embodiments, the interlayer 130 may include, i) two or more emitting units sequentially stacked between the first electrode 110 and the second electrode 150 and ii) a charge generation layer located between the two emitting units. When the interlayer 130 includes the emitting unit and the charge generation layer as described above, the light-emitting device 10 may be a tandem light-emitting device.

[Hole Transport Region in Interlayer 130]

The hole transport region may have: i) a single-layered structure consisting of a single layer consisting of a single material, ii) a single-layered structure consisting of a single layer consisting of a plurality of different materials, or iii) a multi-layered structure including a plurality of layers including different materials.

The hole transport region may include a hole injection layer, a hole transport layer, an emission auxiliary layer, an electron-blocking layer, or any combination thereof.

For example, the hole transport region may have a multi-layered structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron-blocking layer structure, wherein, in each structure, layers are stacked sequentially from the first electrode 110.

The hole transport region may include a compound represented by Formula 201, a compound represented by Formula 202, or any combination thereof:

Formula 201

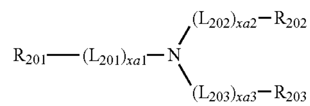

-continued

Formula 202

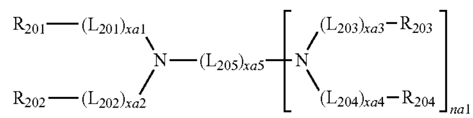

wherein, in Formulae 201 and 202, $L_{201}$ to $L_{204}$ are each independently a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group or the like) unsubstituted or substituted with at least one $R_{10a}$ (for example, Compound HT16), $R_{203}$ and $R_{204}$ may optionally be linked to each other, via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_5$-$C_{60}$ polycyclic group unsubstituted or substituted with at least one $R_{10a}$, $R_{10a}$ may be understood by referring to the previous description of $R_{10a}$ provided above, and na1 may be an integer from 1 to 4.

In one or more embodiments, each of Formulae 201 and 202 may include at least one of groups represented by Formulae CY201 to CY217.

CY201

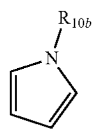

CY202

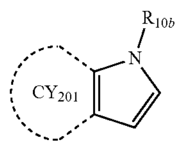

CY203

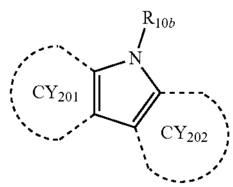

-continued

CY204

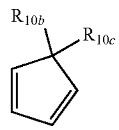

CY205

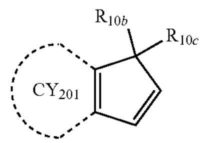

CY206

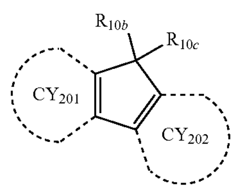

CY207

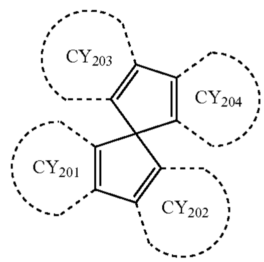

CY208

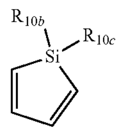

CY209

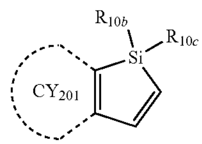

CY210

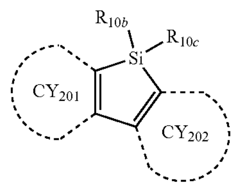

CY211

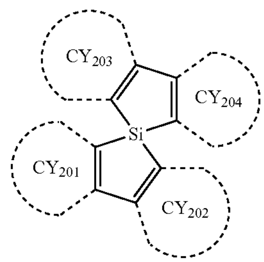

CY212

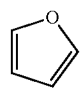

-continued

CY213

CY214

CY215

CY216

CY217

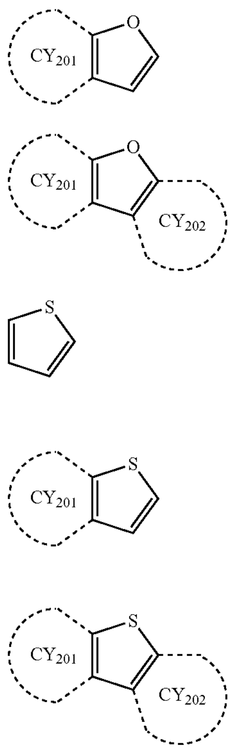

$R_{10b}$ and $R_{10c}$ in Formulae CY201 to CY217 are the same as described in connection with $R_{10a}$, ring $CY_{201}$ to ring $CY_{204}$ may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$, wherein $R_{10a}$ may be understood by referring to the previous description of $R_{10a}$ provided above.

In an embodiment, ring $CY_{201}$ to ring $CY_{204}$ in Formulae CY201 to CY217 may each independently be a benzene group, a naphthalene group, a phenanthrene group, or an anthracene group.

In one or more embodiments, each of Formulae 201 and 202 may include at least one of groups represented by Formulae CY201 to CY203.

In one or more embodiments, Formula 201 may include at least one of groups represented by Formulae CY201 to CY203 and at least one of groups represented by Formulae CY204 to CY217.

In one or more embodiments, in Formula 201, xa1 is 1, $R_{201}$ is a group represented by one of Formulae CY201 to CY203, xa2 may be 0, and $R_{202}$ may be a group represented by one of Formulae CY204 to CY217.

In one or more embodiments, each of Formulae 201 and 202 may not include a group represented by one of Formulae CY201 to CY203.

In one or more embodiments, each of Formulae 201 and 202 may not include a group represented by one of Formulae CY201 to CY203, and may include at least one of groups represented by Formulae CY204 to CY217.

In one or more embodiments, each of Formulae 201 and 202 may not include a group represented by one of Formulae CY201 to CY217.

In an embodiment, the hole transport region may further include one of Compounds HT1 to HT46, m-MTDATA, TDATA, 2-TNATA, NPB(NPD), β-NPB, TPD, Spiro-TPD, Spiro-NPB, methylated-NPB, TAPC, HMTPD, 4,4',4"-tris (N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof:

HT1

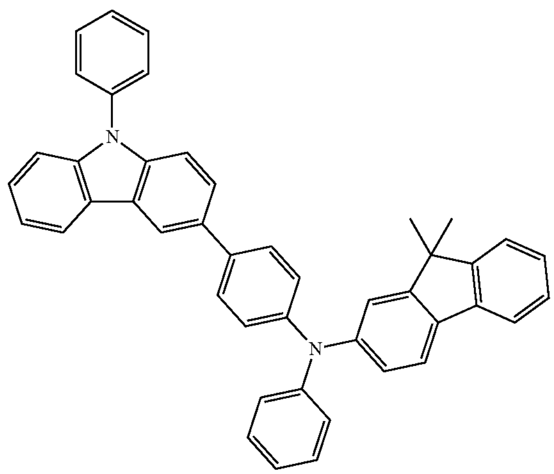

HT2

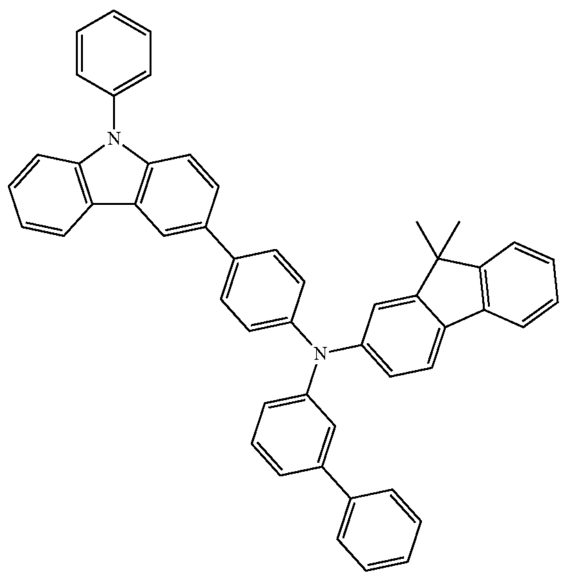

-continued
HT3
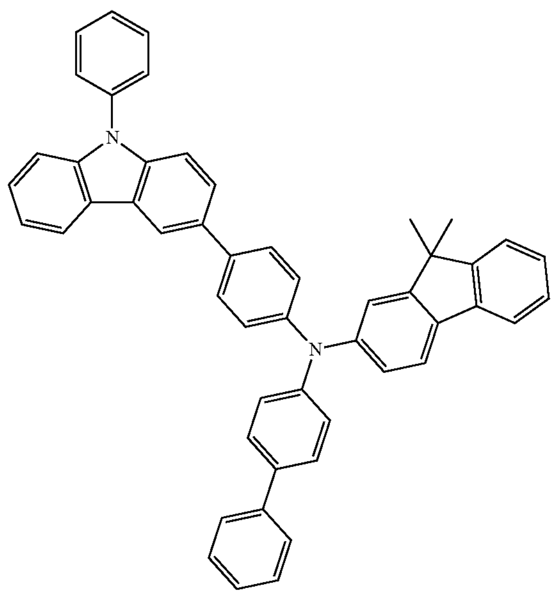
HT4
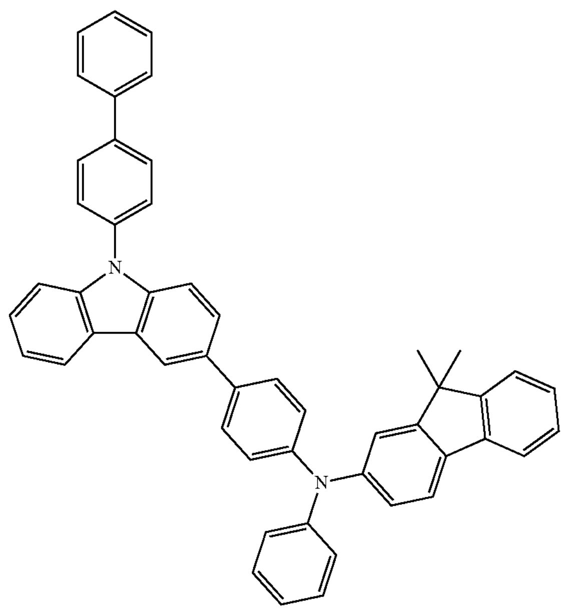
HT5
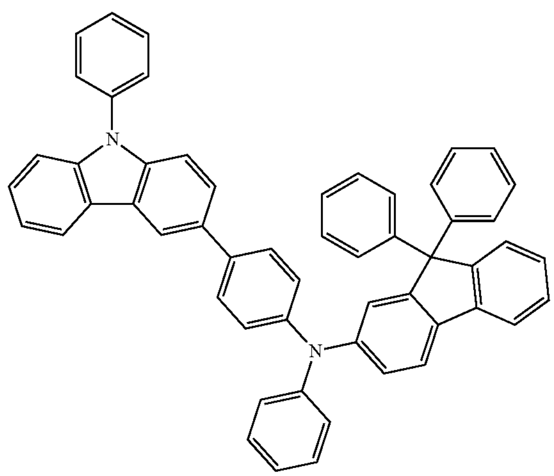
HT6
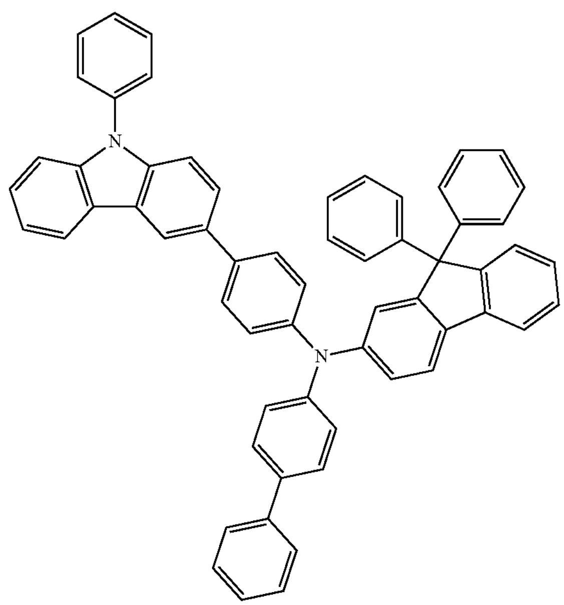

-continued
HT7
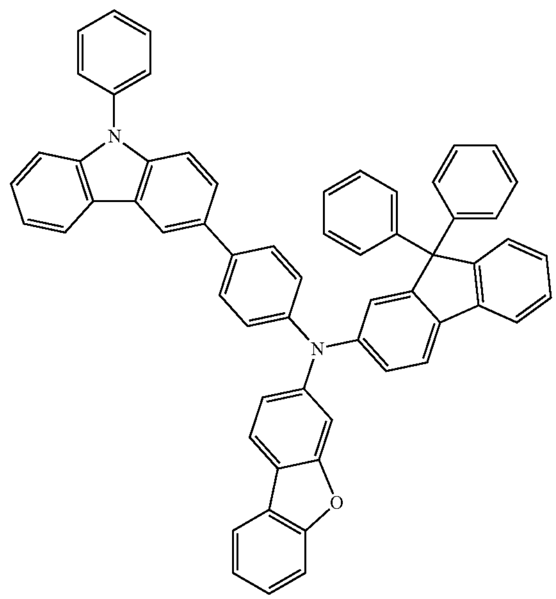
HT8
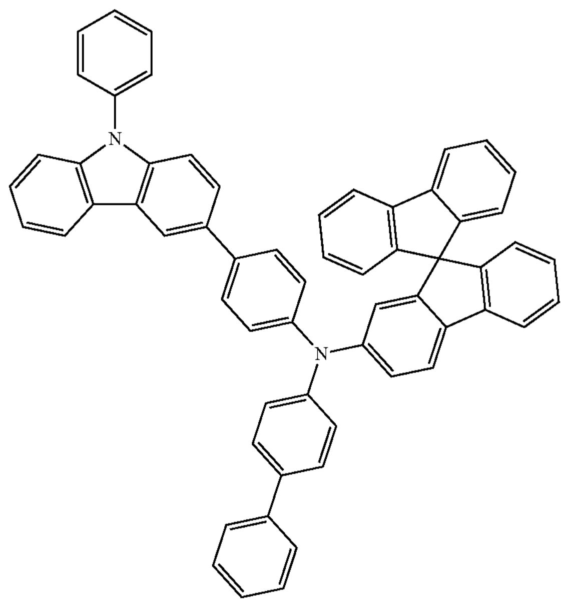
HT9
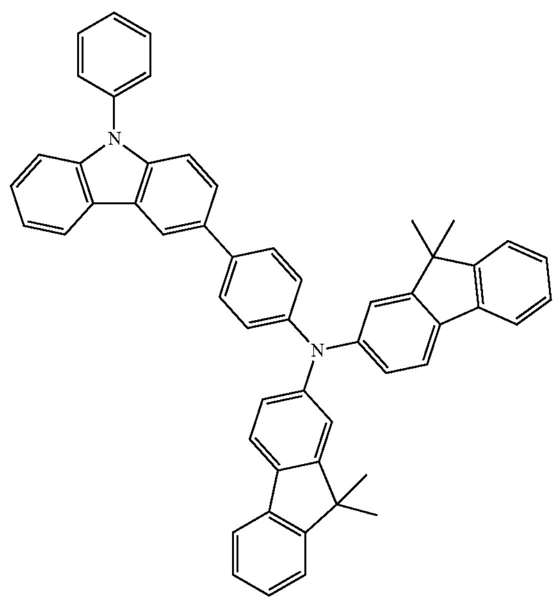
HT10
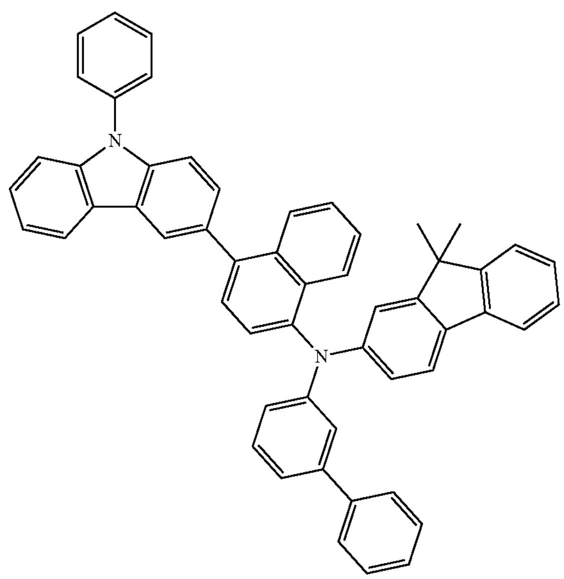

-continued
HT11
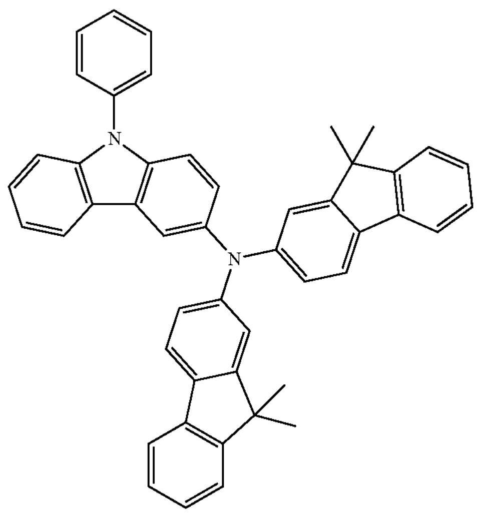
HT12
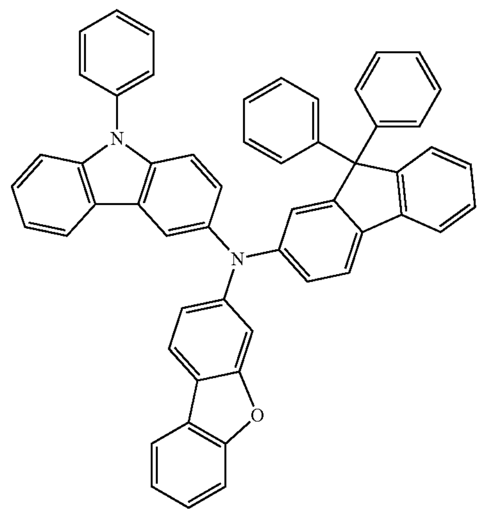
HT13
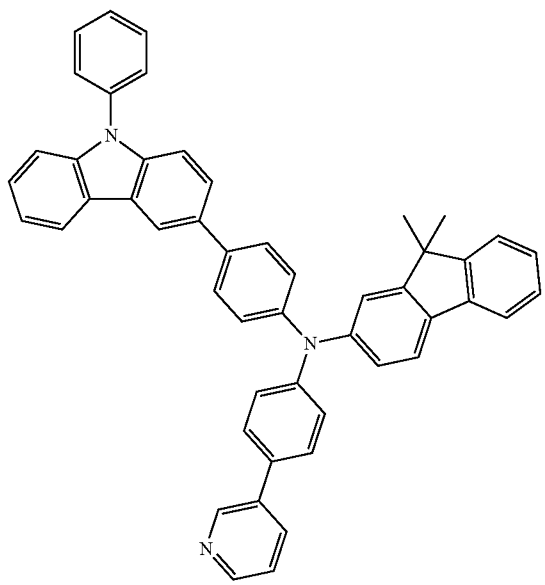
HT14
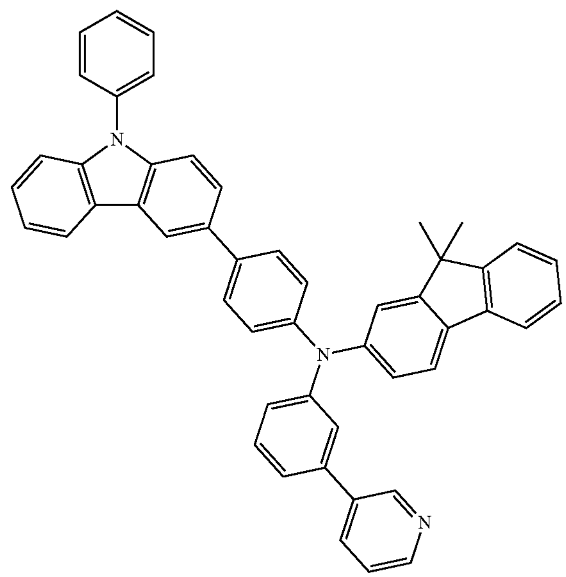
HT15
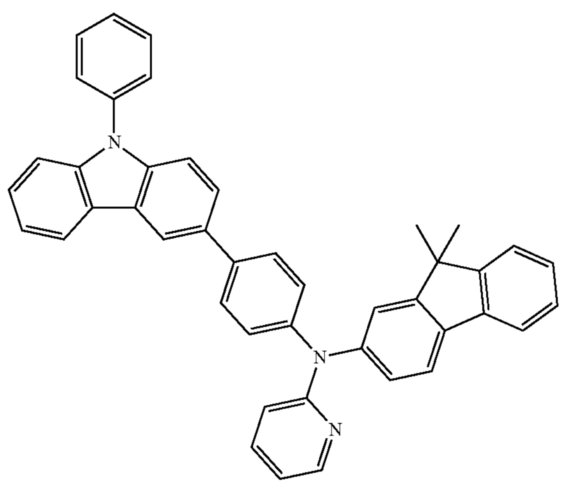
HT16
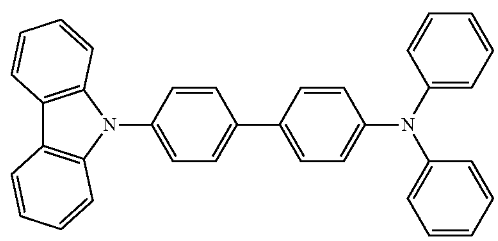

-continued
HT17
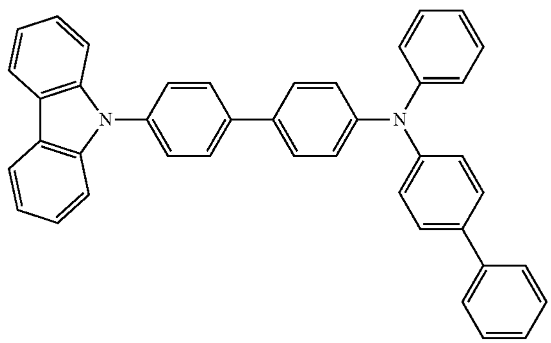
HT18
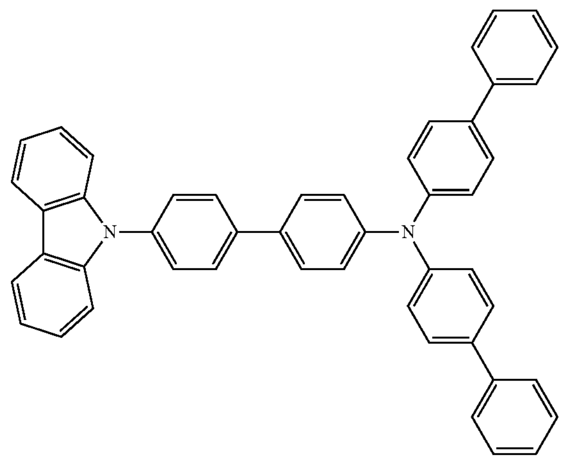
HT19
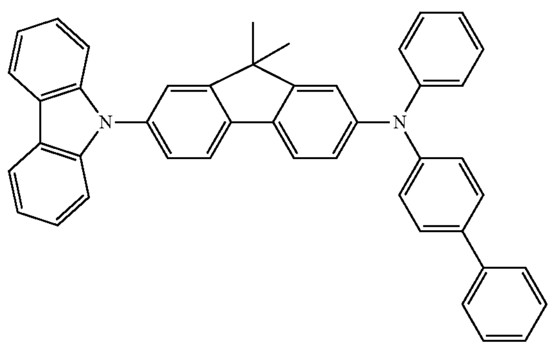
HT20
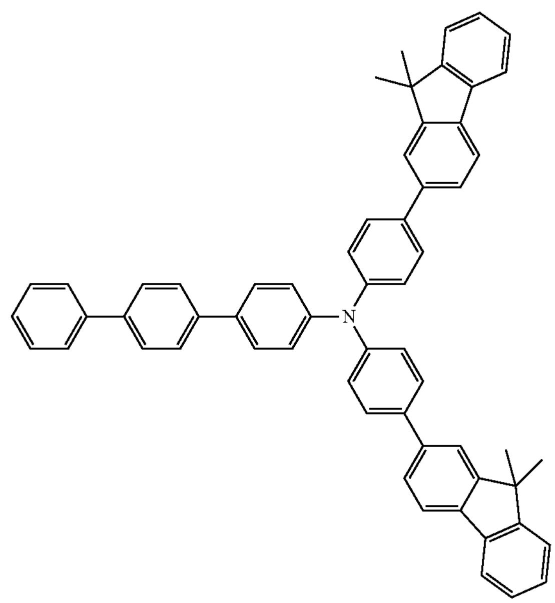

-continued
HT21
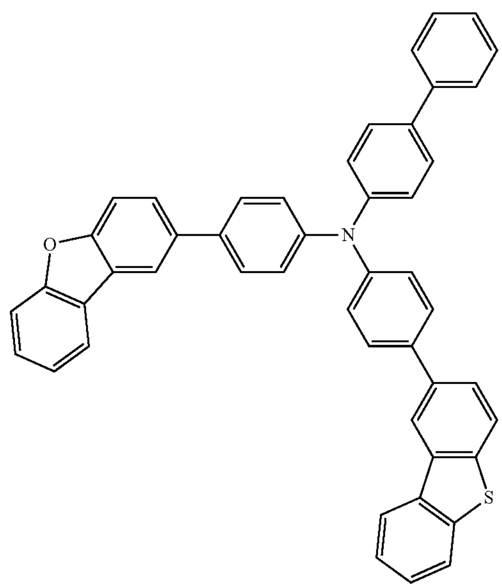
HT22
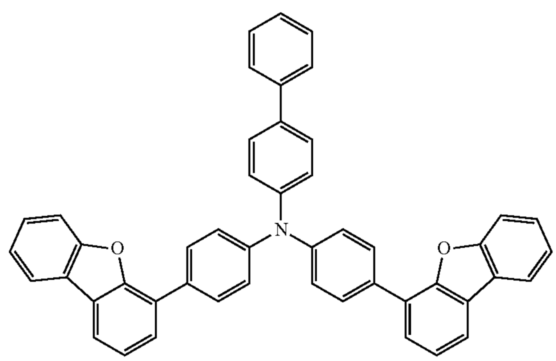
HT23
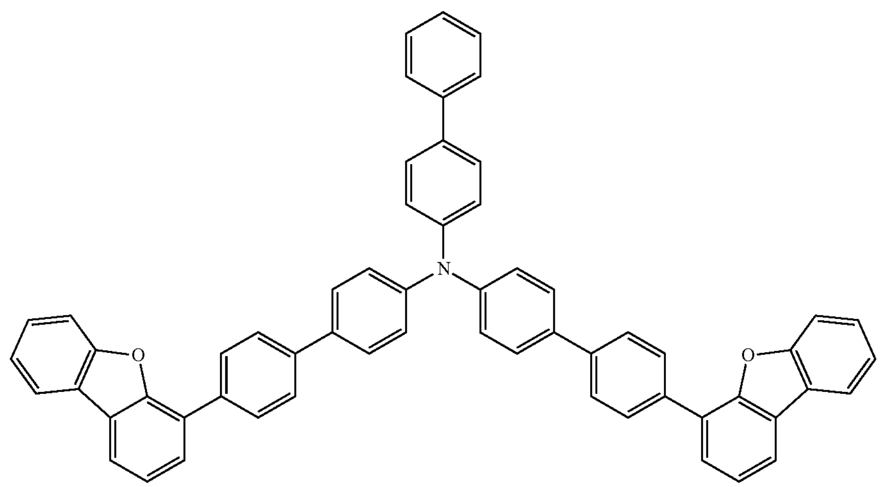

-continued
HT24
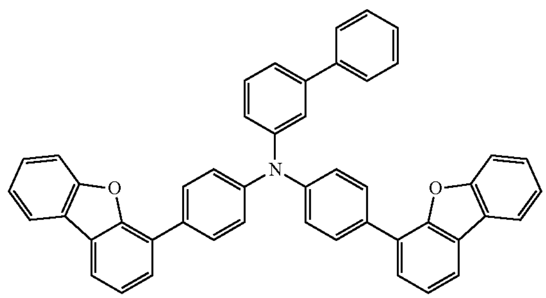
HT25
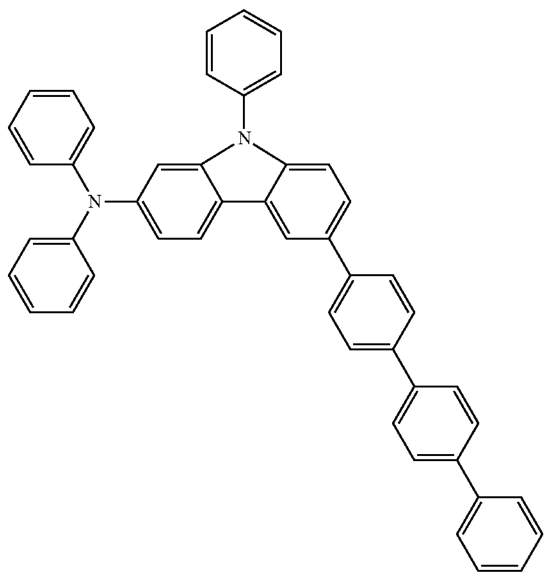
HT26
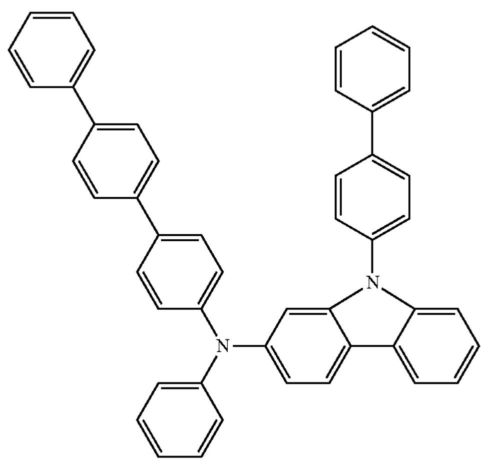
HT27
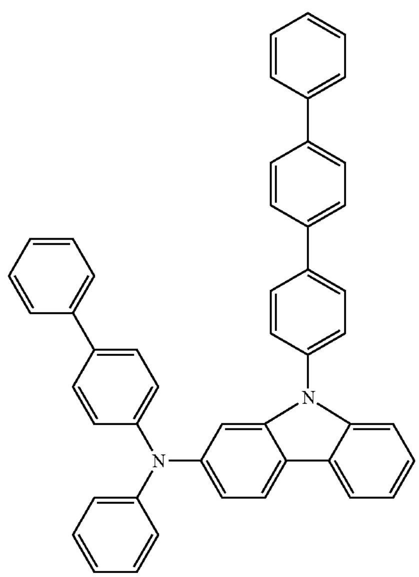
HT28
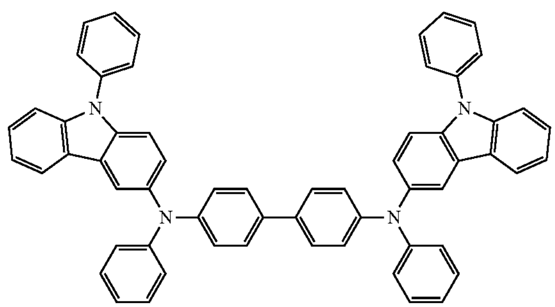
HT29
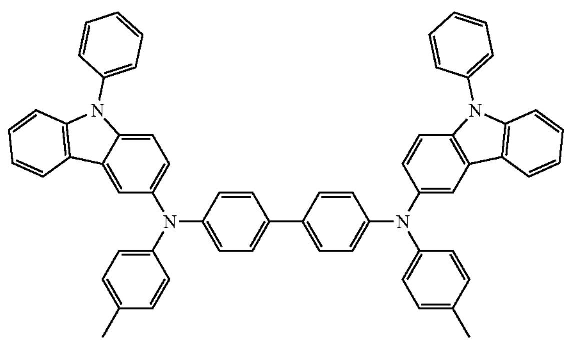

-continued
HT30
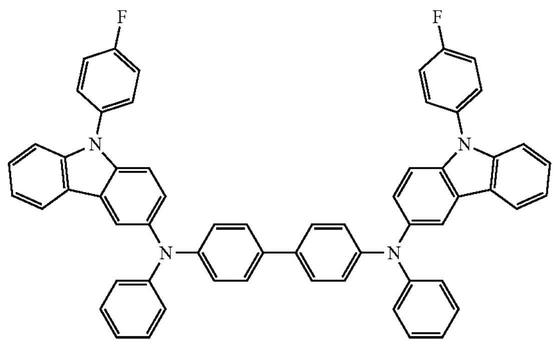
HT31
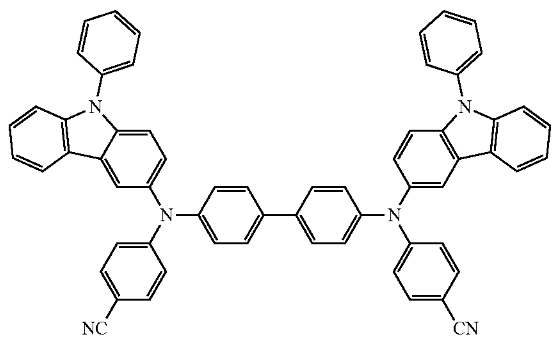
HT32
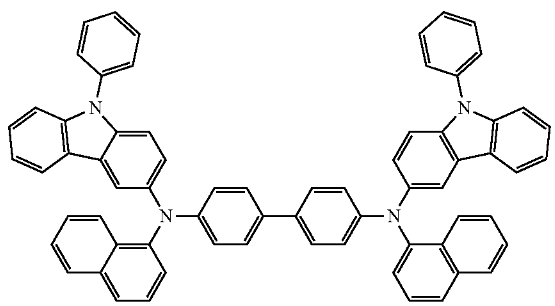
HT33
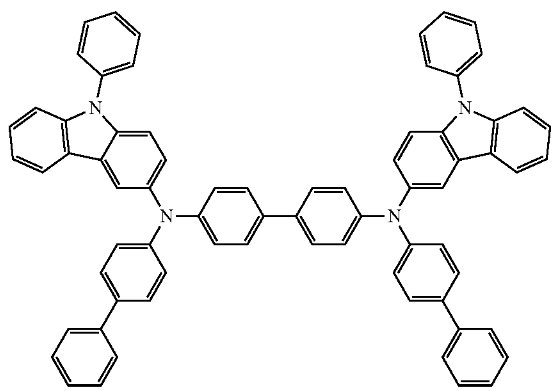
HT34
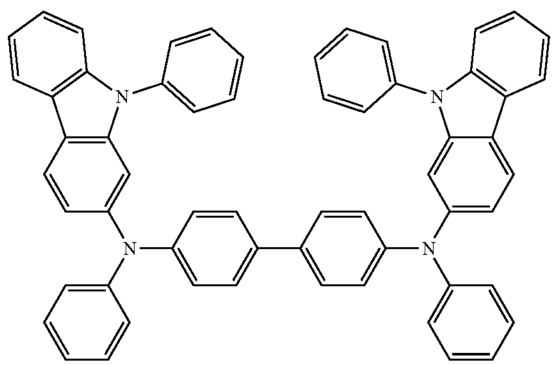
HT35
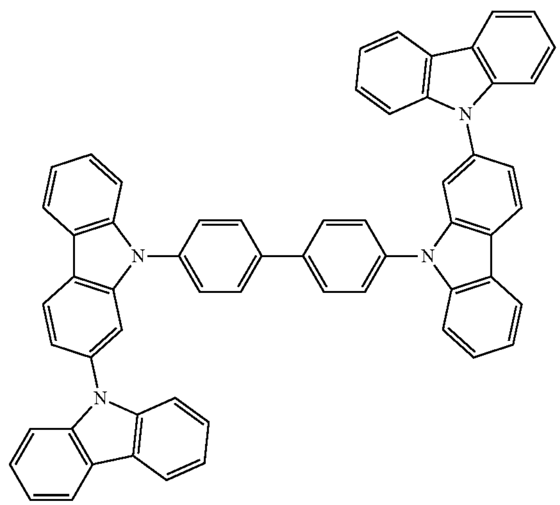

-continued
HT36
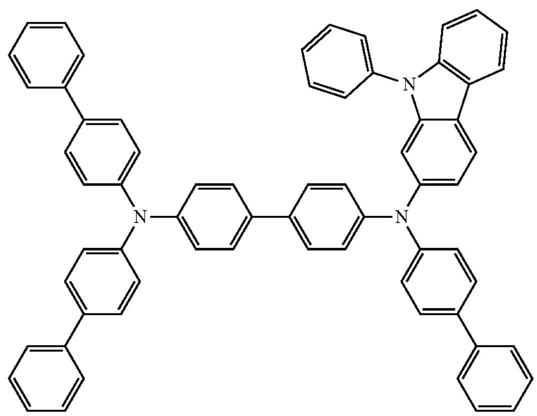
HT37
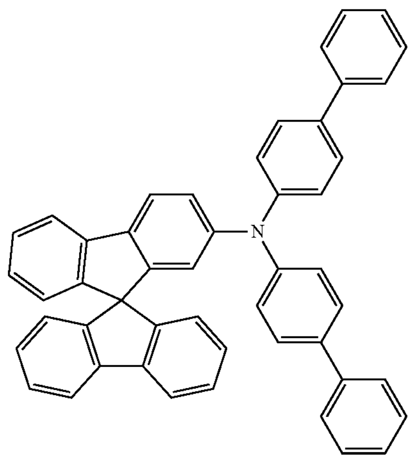
HT38
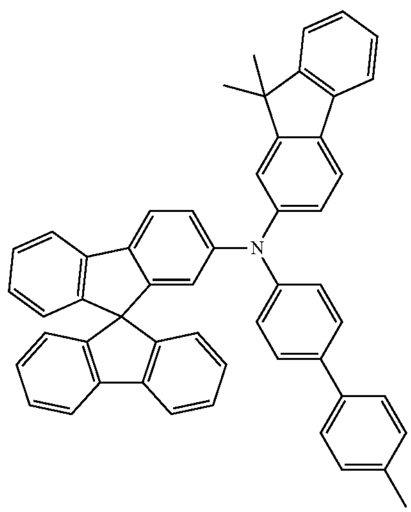
HT39
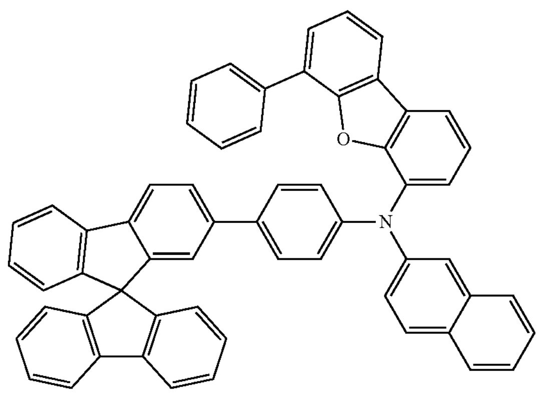
HT40
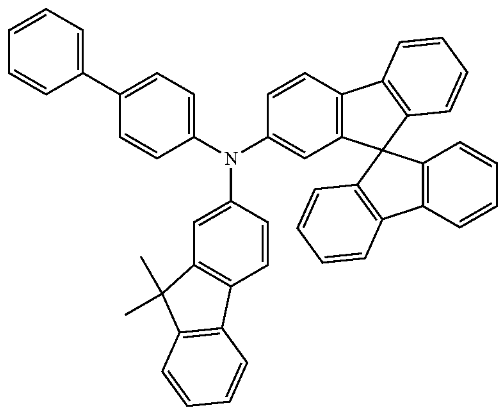
HT41
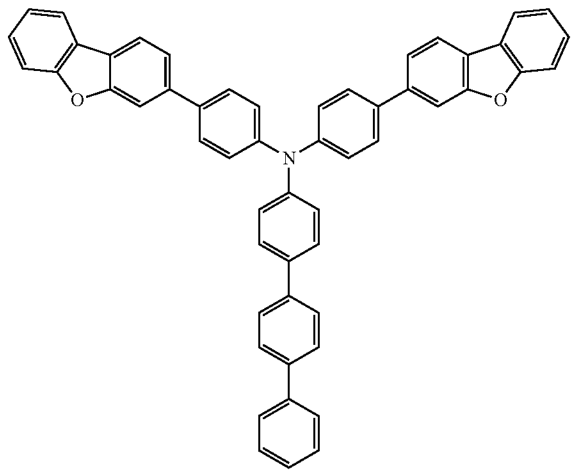

-continued
HT42
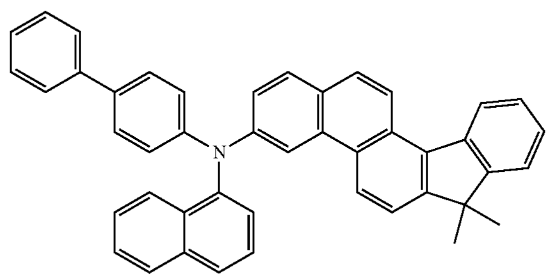
HT43
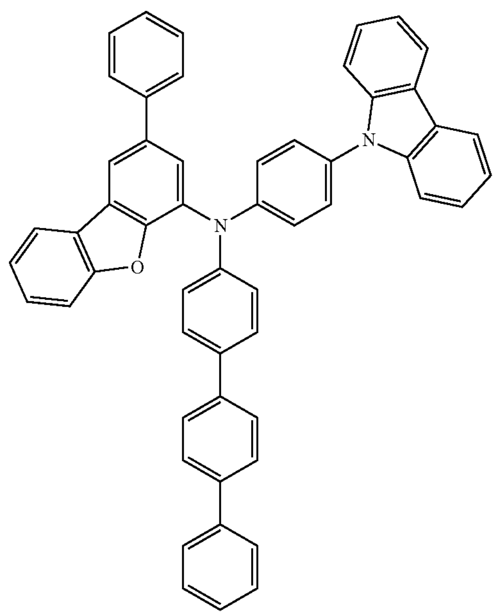
HT44
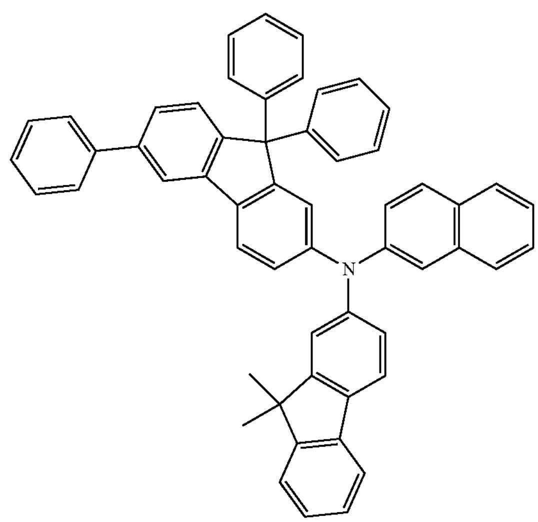
HT45
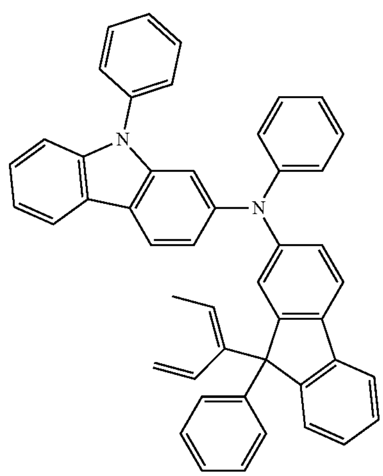

-continued
HT46
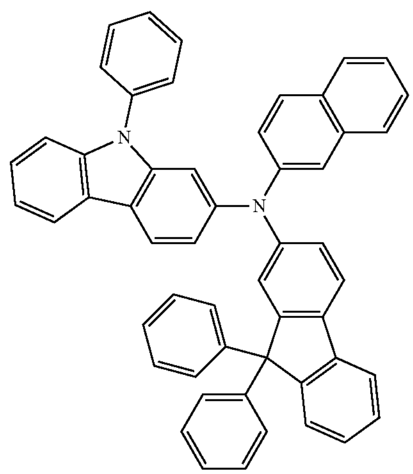
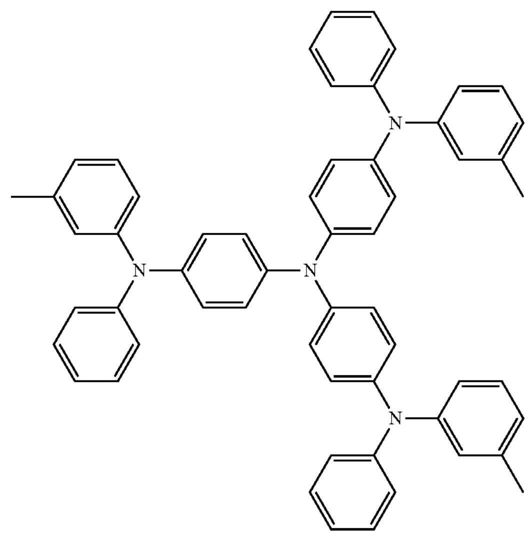
m-MTDATA
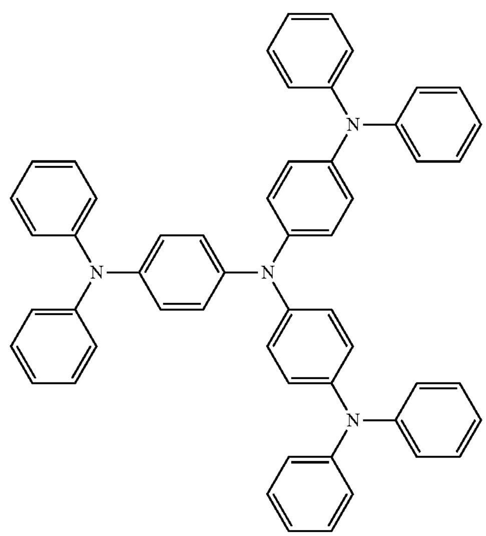
TDATA
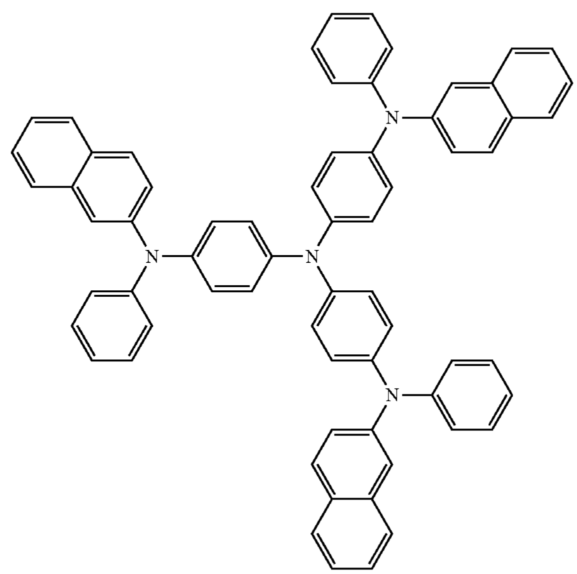
2-TNATA
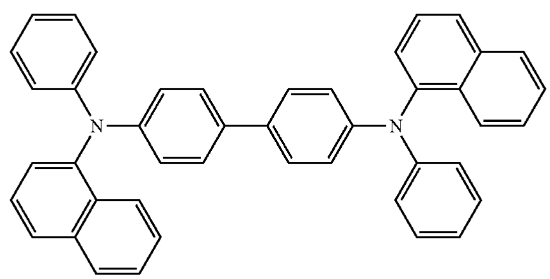
NPB
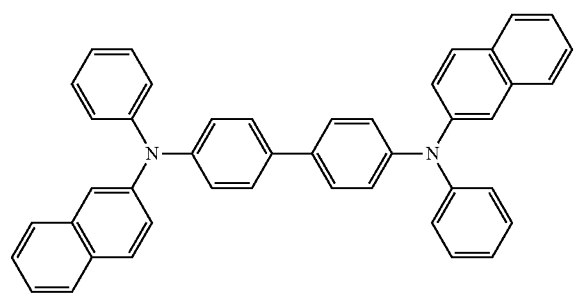
β-NPB -continued

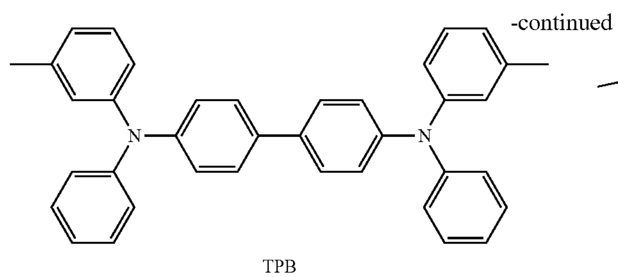

TPB

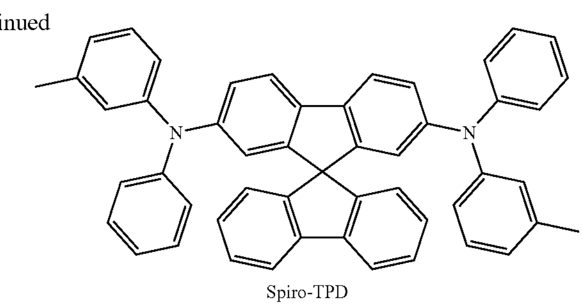

Spiro-TPD

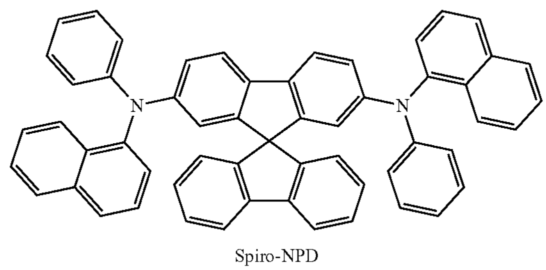

Spiro-NPD

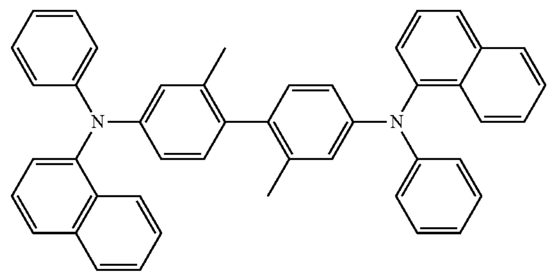

methylated-NPB

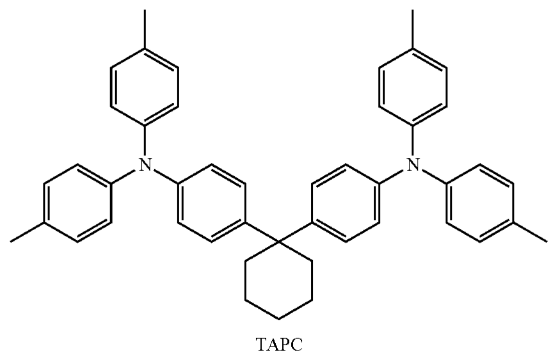

TAPC

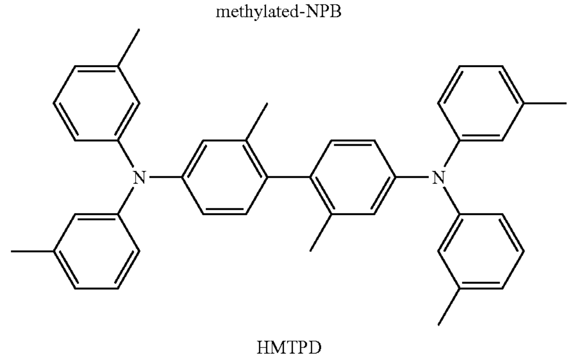

HMTPD

A thickness of the hole transport region may be in a range of about 50 Å to about 10,000 Å, for example, about 100 Å to about 4,000 Å. When the hole transport region includes a hole injection layer, a hole transport layer, or any combination thereof, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron-blocking layer may block the leakage of electrons from an emission layer to a hole transport region. Materials that may be included in the hole transport region may be included in the emission auxiliary layer and the electron-blocking layer.

[p-Dopant]

The hole transport region may further include, in addition to these materials, a charge-generation material for the improvement of conductive properties. The charge-generation material may be uniformly or non-uniformly dispersed in the hole transport region (for example, in the form of a single layer consisting of a charge-generation material).

The charge-generation material may be, for example, a p-dopant.

In one or more embodiments, the lowest unoccupied molecular orbital (LUMO) energy level of the p-dopant may be −3.5 eV (energy level in electron volt) or less.

In one or more embodiments, the p-dopant may include a quinone derivative, a cyano group-containing compound, a compound containing element EL1 and element EL2, or any combination thereof.

Examples of the quinone derivative are TCNQ, F4-TCNQ, etc.

Examples of the cyano group-containing compound are HAT-CN, and a compound represented by Formula 221 below.

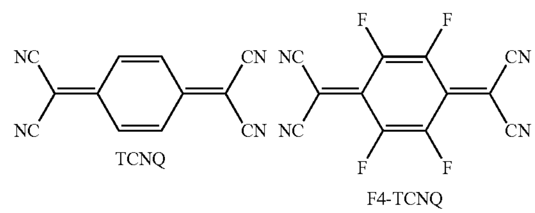

TCNQ

F4-TCNQ

-continued

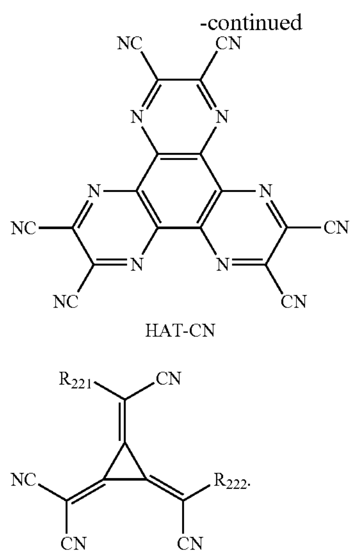

HAT-CN

Formula 221

In Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one of $R_{221}$ to $R_{223}$ may each independently be a $C_3$-$C_{60}$ carbocyclic group or a $C_1$-$C_{60}$ heterocyclic group, each substituted with a cyano group; —F; —Cl; —Br; —I; a $C_1$-$C_{20}$ alkyl group substituted with a cyano group, —F, —Cl, —Br, —I, or any combination thereof, or any combination thereof, wherein $R_{10a}$ may be understood by referring to the previous description of $R_{10a}$ provided above.

In the compound containing element EL1 and element EL2, element EL1 may be metal, metalloid, or any combination thereof, and element EL2 may be non-metal, metalloid, or any combination thereof.

Examples of the metal are an alkali metal (for example, lithium (Li), sodium (Na), potassium (K), rubidium (Rb), cesium (Cs), etc.); alkaline earth metal (for example, beryllium (Be), magnesium (Mg), calcium (Ca), strontium (Sr), barium (Ba), etc.); transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), etc.); post-transition metal (for example, zinc (Zn), indium (In), tin (Sn), etc.); and lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), etc.).

Examples of the metalloid are silicon (Si), antimony (Sb), and tellurium (Te).

Examples of the non-metal are oxygen (O) and halogen (for example, F, Cl, Br, I, etc.).

In one or more embodiments, examples of the compound containing element EL1 and element EL2 are metal oxide, metal halide (for example, metal fluoride, metal chloride, metal bromide, or metal iodide), metalloid halide (for example, metalloid fluoride, metalloid chloride, metalloid bromide, or metalloid iodide), metal telluride, or any combination thereof.

Examples of the metal oxide are tungsten oxide (for example, WO, $W_2O_3$, $WO_2$, $WO_3$, $W_2O_5$, etc.), vanadium oxide (for example, VO, $V_2O_3$, $VO_2$, $V_2O_5$, etc.), molybdenum oxide (for example, MoO, $Mo_2O_3$, $MoO_2$, $MoO_3$, $Mo_2O_5$, etc.), and rhenium oxide (for example, $ReO_3$, etc.).

Examples of the metal halide are alkali metal halide, alkaline earth metal halide, transition metal halide, post-transition metal halide, and lanthanide metal halide.

Examples of the alkali metal halide are LiF, NaF, KF, RbF, CsF, LiCl, NaCl, KCl, RbCl, CsCl, LiBr, NaBr, KBr, RbBr, CsBr, LiI, NaI, KI, RbI, and CsI.

Examples of the alkaline earth metal halide are $BeF_2$, $MgF_2$, $CaF_2$, $SrF_2$, $BaF_2$, $BeCl_2$, $MgCl_2$, $CaCl_2$, $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$.

Examples of the transition metal halide are titanium halide (for example, $TiF_4$, $TiCl_4$, $TiBr_4$, $TiI_4$, etc.), zirconium halide (for example, $ZrF_4$, $ZrCl_4$, $ZrBr_4$, $ZrI_4$, etc.), hafnium halide (for example, $HfF_4$, $HfCl_4$, $HfBr_4$, $HfI_4$, etc.), vanadium halide (for example, $VF_3$, $VCl_3$, $VBr_3$, $VI_3$, etc.), niobium halide (for example, $NbF_3$, $NbCl_3$, $NbBr_3$, $NbI_3$, etc.), tantalum halide (for example, $TaF_3$, $TaCl_3$, $TaBr_3$, $TaI_3$, etc.), chromium halide (for example, $CrF_3$, $CrCl_3$, $CrBr_3$, $CrI_3$, etc.), molybdenum halide (for example, $MoF_3$, $MoCl_3$, $MoBr_3$, $MoI_3$, etc.), tungsten halide (for example, $WF_3$, $WCl_3$, $WBr_3$, $WI_3$, etc.), manganese halide (for example, $MnF_2$, $MnCl_2$, $MnBr_2$, $MnI_2$, etc.), technetium halide (for example, $TcF_2$, $TcCl_2$, $TcBr_2$, $TcI_2$, etc.), rhenium halide (for example, $ReF_2$, $ReCl_2$, $ReBr_2$, $ReI_2$, etc.), iron halide (for example, $FeF_2$, $FeCl_2$, $FeBr_2$, $FeI_2$, etc.), ruthenium halide (for example, $RuF_2$, $RuCl_2$, $RuBr_2$, $RuI_2$, etc.), osmium halide (for example, $OsF_2$, $OsCl_2$, $OsBr_2$, $OsI_2$, etc.), cobalt halide (for example, $CoF_2$, $CoCl_2$, $CoBr_2$, $CoI_2$, etc.), rhodium halide (for example, $RhF_2$, $RhCl_2$, $RhBr_2$, $RhI_2$, etc.), iridium halide (for example, $IrF_2$, $IrCl_2$, $IrBr_2$, $IrI_2$, etc.), nickel halide (for example, $NiF_2$, $NiCl_2$, $NiBr_2$, $NiI_2$, etc.), palladium halide (for example, $PdF_2$, $PdCl_2$, $PdBr_2$, $PdI_2$, etc.), platinum halide (for example, $PtF_2$, $PtCl_2$, $PtBr_2$, $PtI_2$, etc.), copper halide (for example, CuF, CuCl, CuBr, CuI, etc.), silver halide (for example, AgF, AgCl, AgBr, AgI, etc.), and gold halide (for example, AuF, AuCl, AuBr, AuI, etc.).

Examples of the post-transition metal halide are zinc halide (for example, $ZnF_2$, $ZnCl_2$, $ZnBr_2$, $ZnI_2$, etc.), indium halide (for example, $InI_3$, etc.), and tin halide (for example, $SnI_2$, etc.).

Examples of the lanthanide metal halide are YbF, $YbF_2$, $YbF_3$, $SmF_3$, YbCl, $YbCl_2$, $YbCl_3$, $SmCl_3$, YbBr, $YbBr_2$, $YbBr_3$ $SmBr_3$, YbI, $YbI_2$, $YbI_3$, and $SmI_3$.

An example of the metalloid halide is antimony halide (for example, $SbCl_5$, etc.).

Examples of the metal telluride are alkali metal telluride (for example, $Li_2Te$, $Na_2Te$, $K_2Te$, $Rb_2Te$, $Cs_2Te$, etc.), alkaline earth metal telluride (for example, BeTe, MgTe, CaTe, SrTe, BaTe, etc.), transition metal telluride (for example, $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, $Au_2Te$, etc.), post-transition metal telluride (for example, ZnTe, etc.), and lanthanide metal telluride (for example, LaTe, CeTe, PrTe, NdTe, PmTe, EuTe, GdTe, TbTe, DyTe, HoTe, ErTe, TmTe, YbTe, LuTe, etc.).

[Emission Layer in Interlayer 130]

The light-emitting device according to an embodiment may include an emission layer 135 in an interlayer.

When the light-emitting device 10 is a full-color light-emitting device, the emission layer may be patterned into a red emission layer, a green emission layer, and/or a blue emission layer, according to a sub-pixel. In one or more embodiments, the emission layer may have a stacked structure of two or more layers of a red emission layer, a green emission layer, and a blue emission layer, in which the two or more layers contact each other or are separated from each other. In one or more embodiments, the emission layer may include two or more materials of a red light-emitting material, a green light-emitting material, and a blue light-emitting material, in which the two or more materials are mixed with each other in a single layer to emit white light.

The emission layer may include a host and a dopant. In this regard, the dopant may include a phosphorescent dopant, a fluorescent dopant, a delayed fluorescence material, or any combination thereof.

The amount of the dopant in the emission layer may be from about 0.01 to about 15 parts by weight based on 100 parts by weight of the host.

In one or more embodiments, the emission layer may include a quantum dot.

Meanwhile, the emission layer may include a delayed fluorescence material. The delayed fluorescence material may act as a host or a dopant in the emission layer.

A thickness of the emission layer may be in a range of about 100 Å to about 1,000 Å, for example, about 200 Å to about 600 Å. When the thickness of the emission layer is within these ranges, excellent light-emission characteristics may be obtained without a substantial increase in driving voltage.

[Host]

In one or more embodiments, the host may include a compound represented by Formula 301 below:

Formula 301

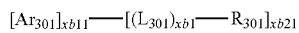

In Formula 301, $Ar_{301}$ and $L_{301}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xb11 may be 1, 2, or 3, xb1 may be an integer from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), or —P(=O)($Q_{301}$)($Q_{302}$), xb21 may be an integer from 1 to 5, wherein $R_{10a}$ may be understood by referring to the previous description of $R_{10a}$ provided above, and $Q_{301}$ to $Q_{303}$ are the same as described in connection with $Q_1$.

For example, when xb11 in Formula 301 is 2 or more, two or more of $Ar_{301}$(s) may be linked to each other via a single bond.

In one or more embodiments, the host may include a compound represented by Formula 301-1, a compound represented by Formula 301-2, or any combination thereof:

Formula 301-1

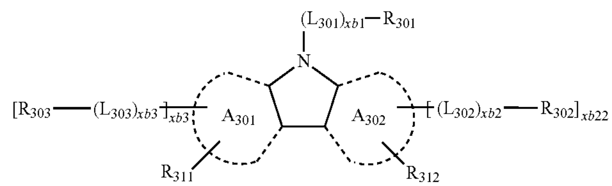

Formula 301-2

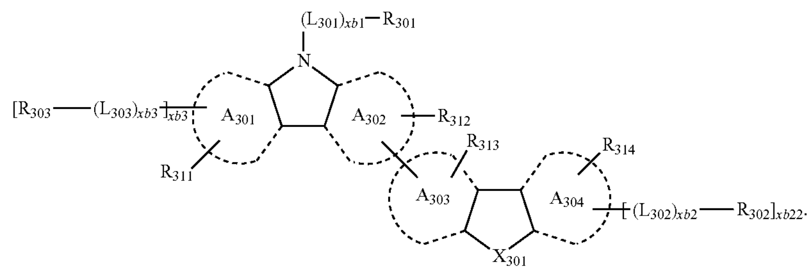

In Formulae 301-1 to 301-2, ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $X_{301}$ may be O, S, N-[$(L_{304})_{xb4}$-$R_{304}$], C($R_{304}$)($R_{305}$), or Si($R_{304}$)($R_{305}$), xb22 and xb23 may each independently be 0, 1, or 2, $L_{301}$, xb1, and $R_{301}$ are the same as described in the present specification, $L_{302}$ to $L_{304}$ may each independently be the same as described in connection with $L_{301}$, xb2 to xb4 may each independently be the same as described in connection with xb1, $R_{10a}$ may be understood by referring to the previous description of $R_{10a}$ provided above, and $R_{302}$ to $R_{305}$ and $R_{311}$ to $R_{314}$ are the same as described in connection with $R_{301}$.

In one or more embodiments, the host may include an alkali earth metal complex, a post-transition metal complex, or any combination thereof. In one or more embodiments, the host may include a Be complex (for example, Compound H55), an Mg complex, a Zn complex, or any combination thereof.

In an embodiment, the host may include one of Compounds H1 to H124, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolyl-benzene (mCP), 1,3,5-tri(carbazol-9-yl)benzene (TCP), or any combination thereof:

H1

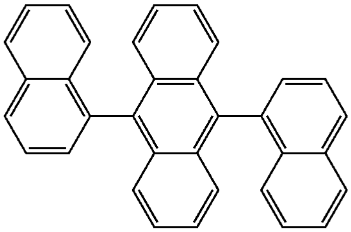

H2

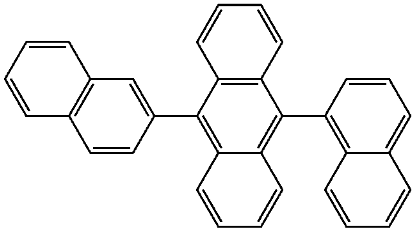

H3

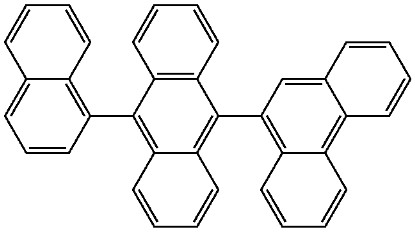

H4

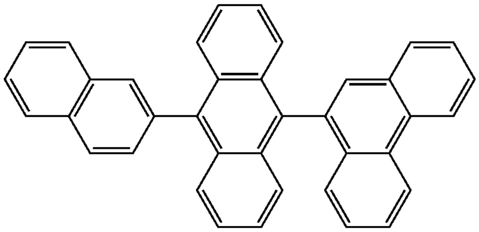

H5

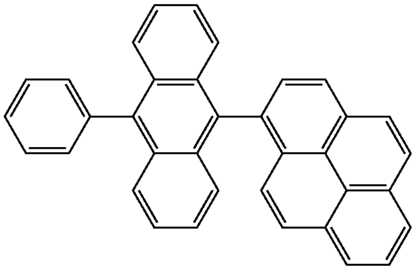

-continued

H6

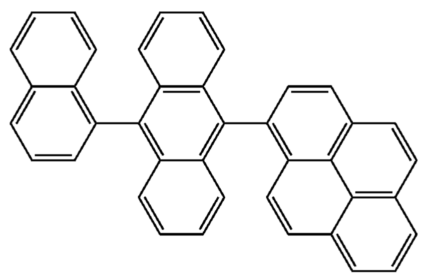

H7

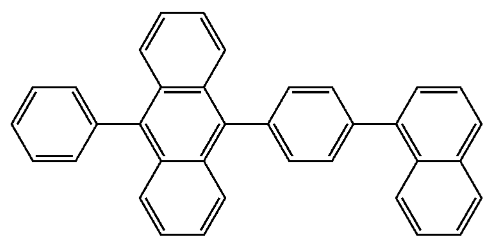

H8

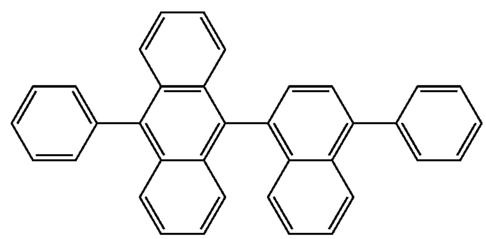

H9

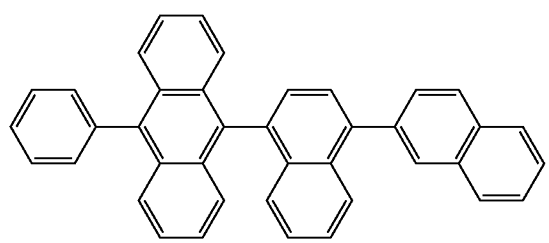

H10

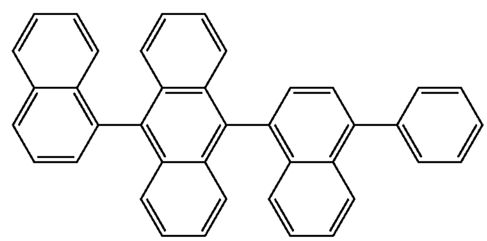

H11

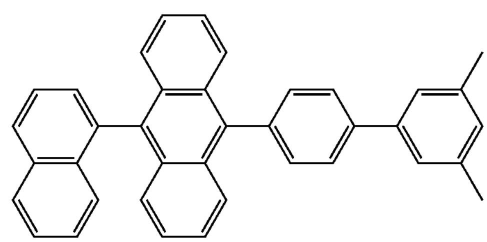

-continued
H12
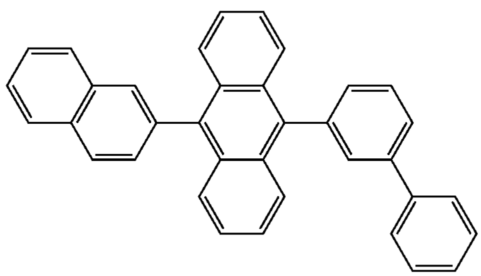
H13
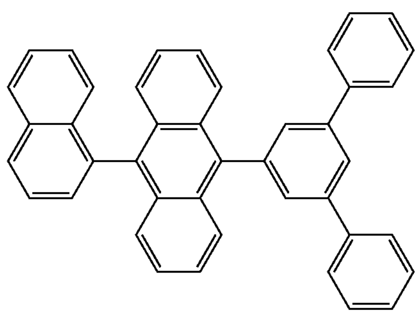
H14
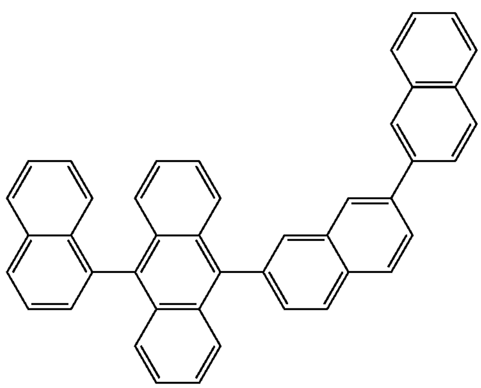
H15
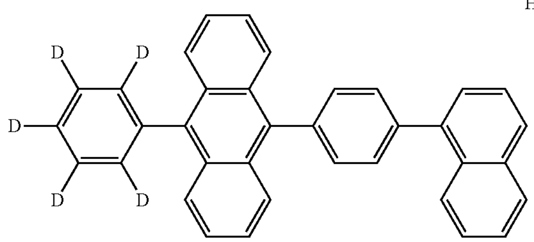
H16
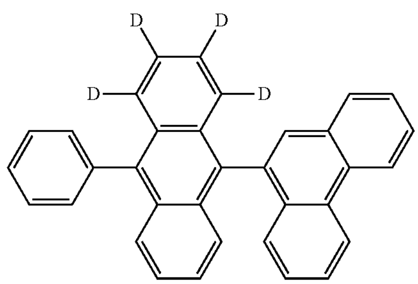
-continued
H17
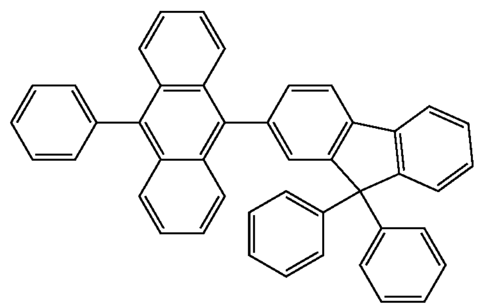
H18
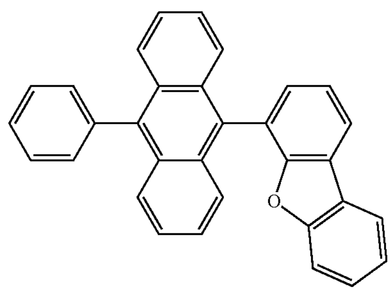
H19
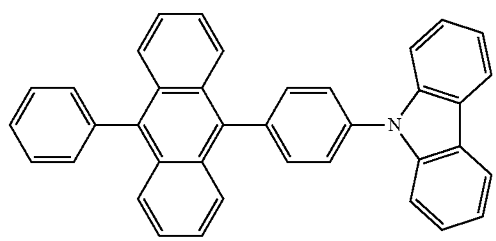
H20
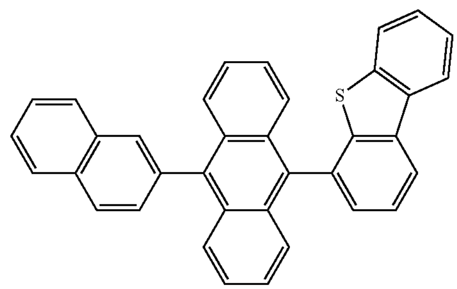
H21
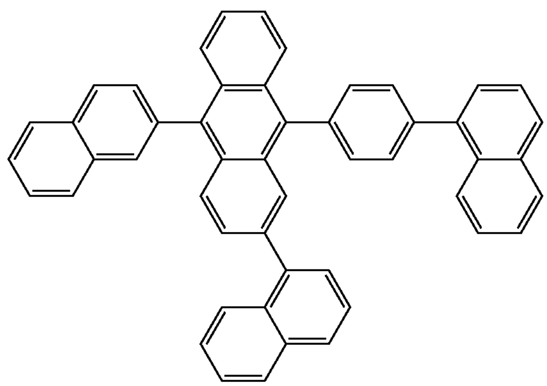

-continued
H22
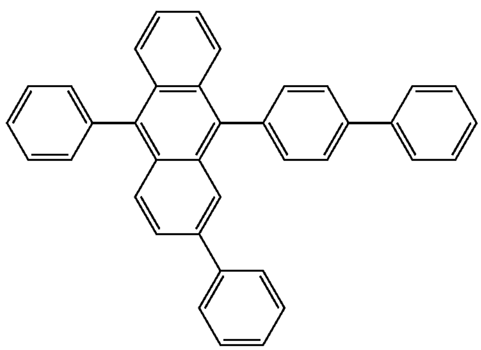
H23
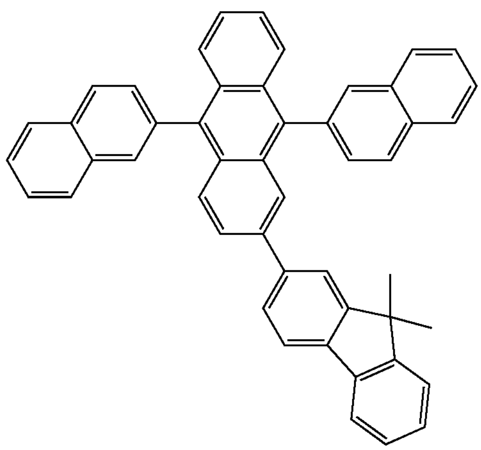
H24
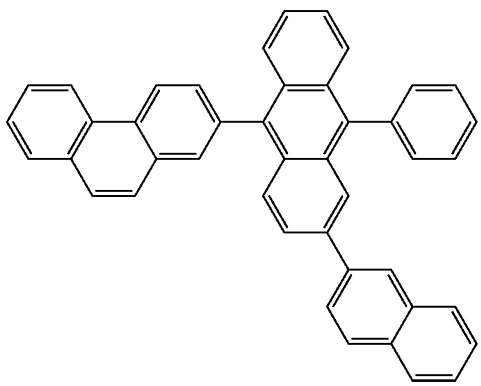
-continued
H25
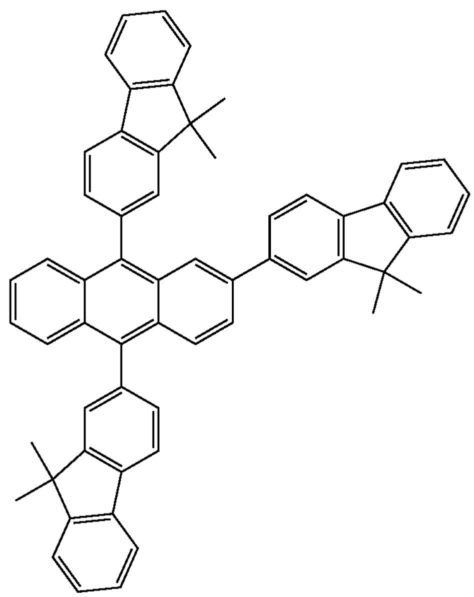
H26
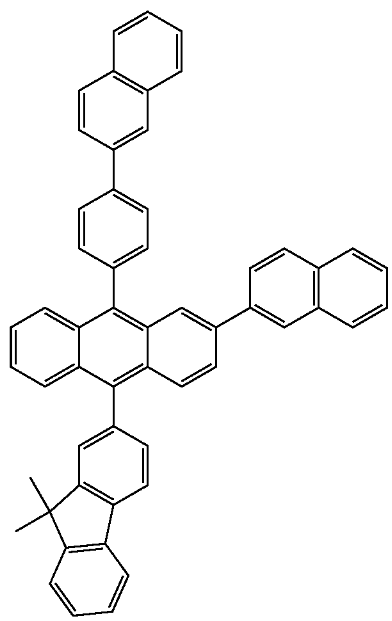

-continued
H27
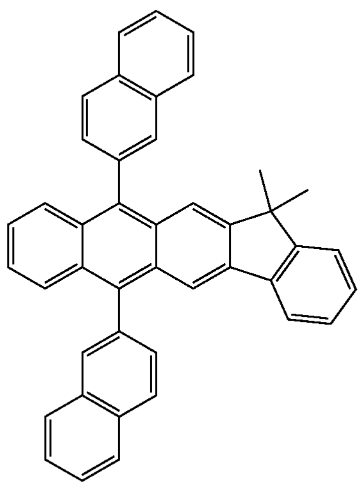
H28
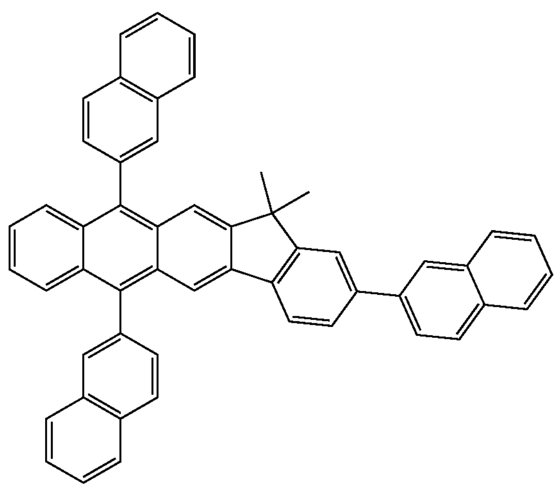
H29
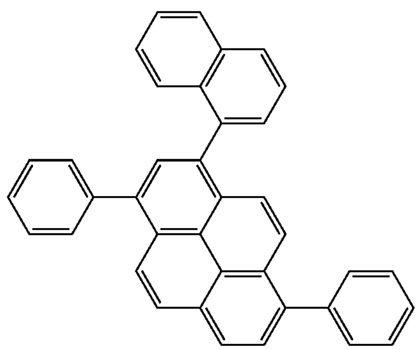
-continued
H30
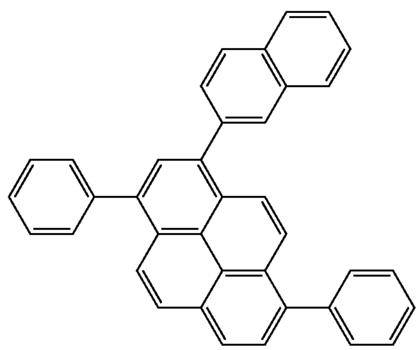
H31
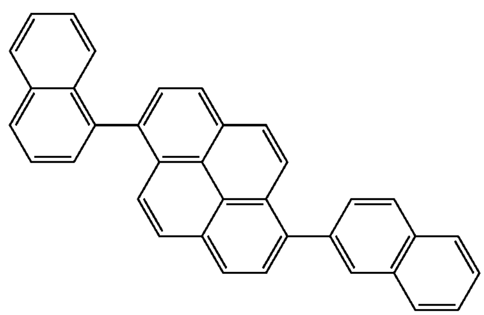
H32
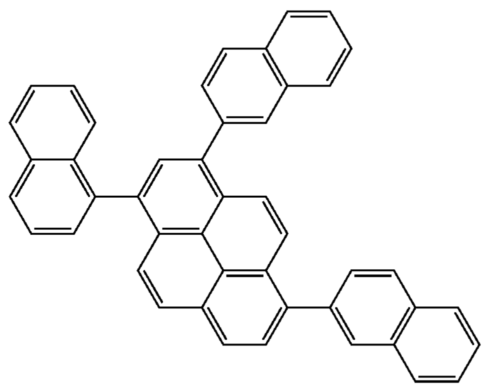
H33
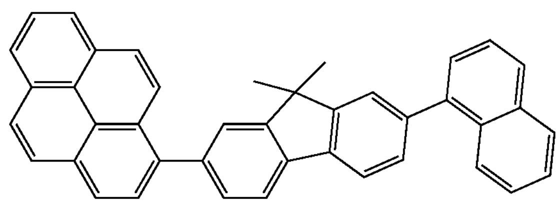
H34
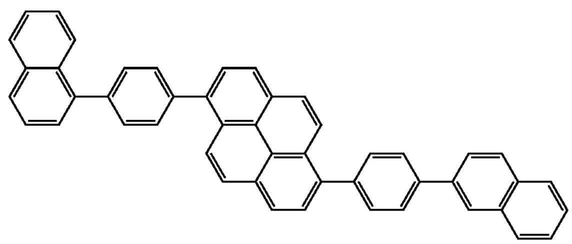

-continued
H35
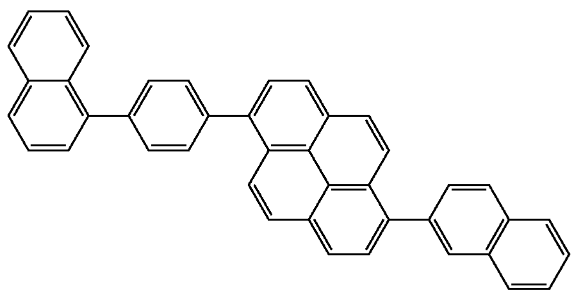
H36
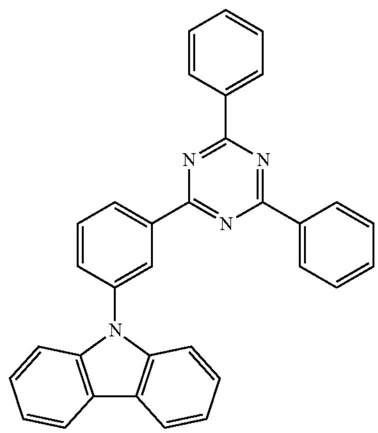
H37
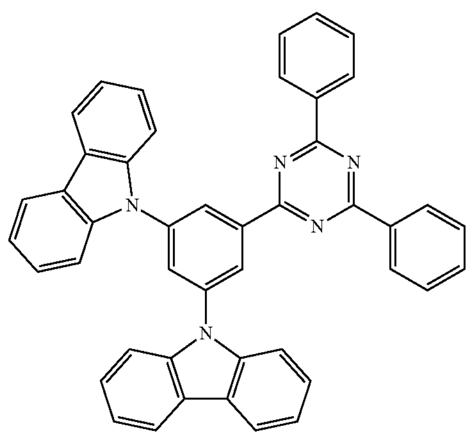
H38
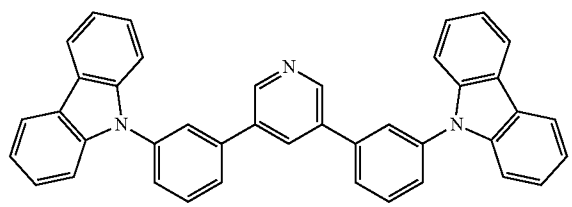
-continued
H39
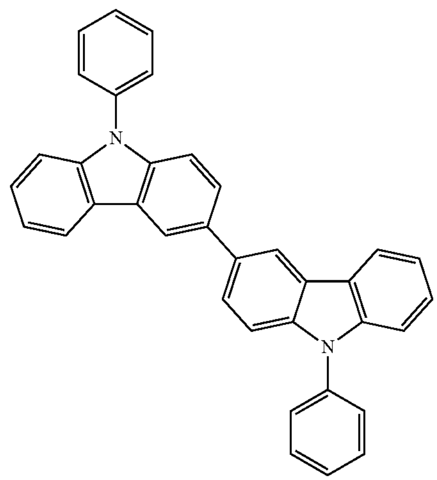
H40
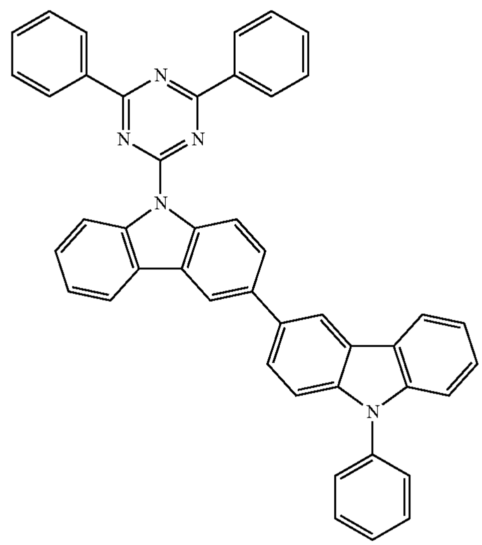
H41
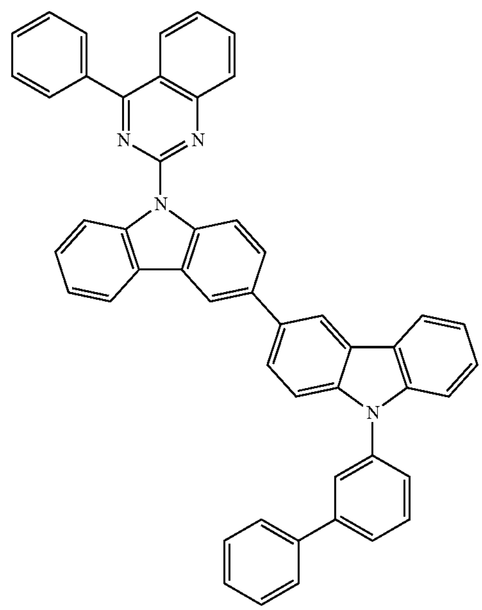

-continued
H42
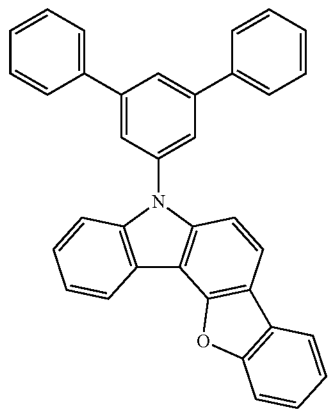
H43
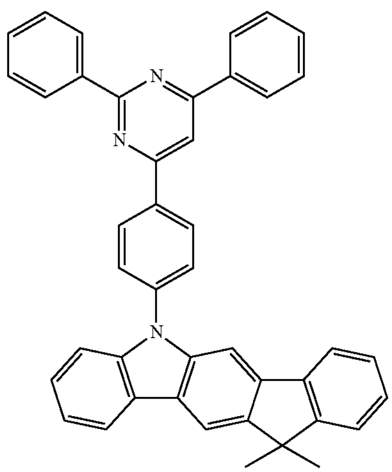
H44
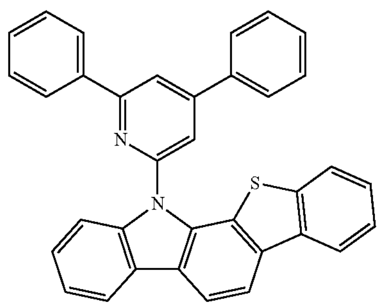
H45
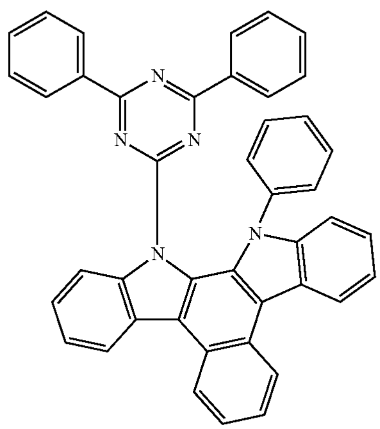
-continued
H46
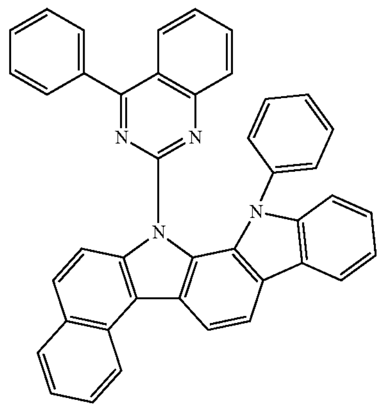
H47
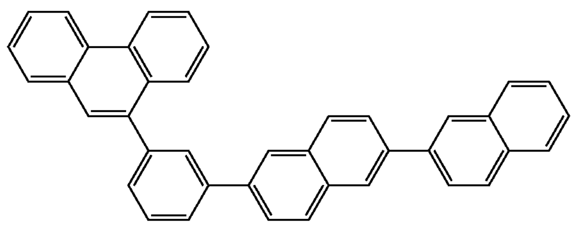
H48
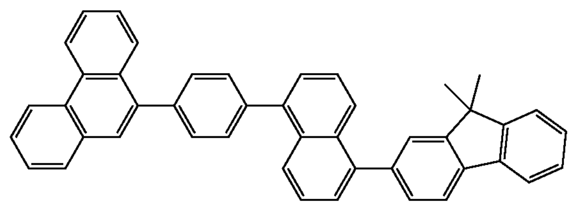
H49
H50
H51
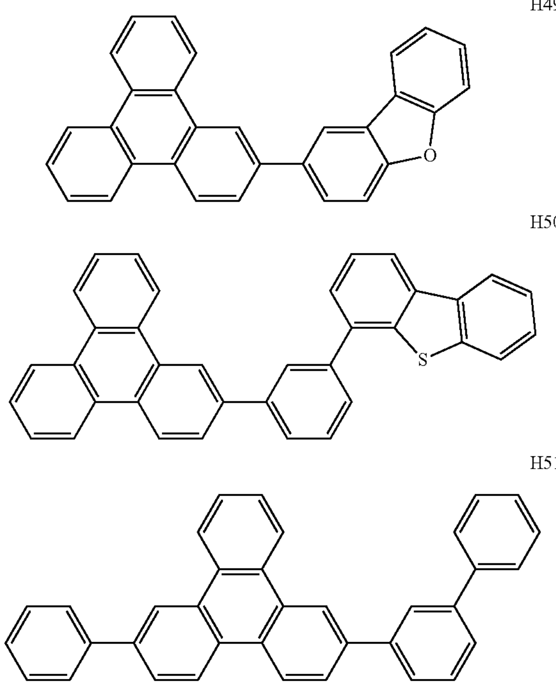

-continued
H52
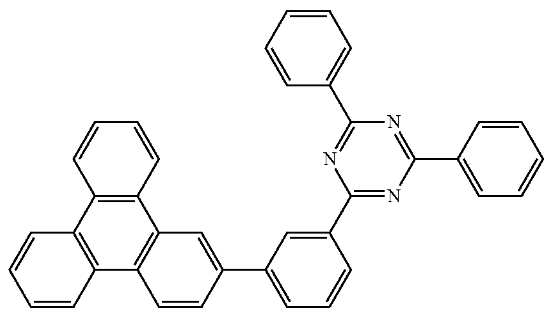
H53
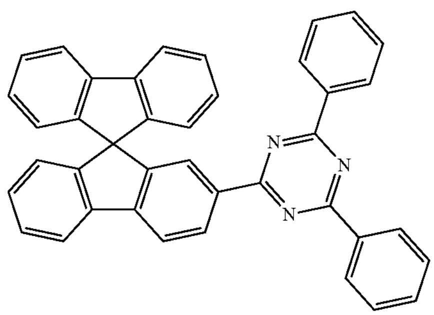
H54
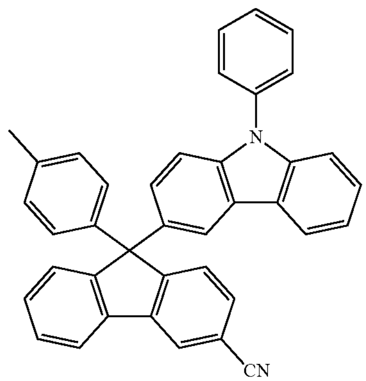
H55
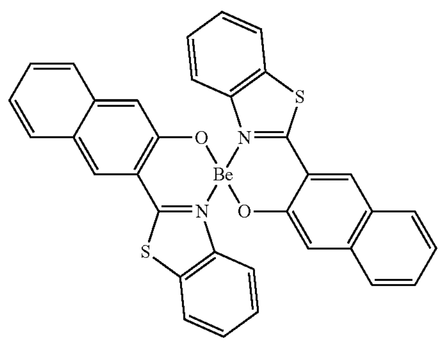
-continued
H56
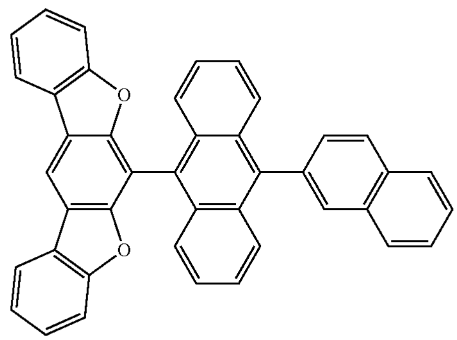
H57
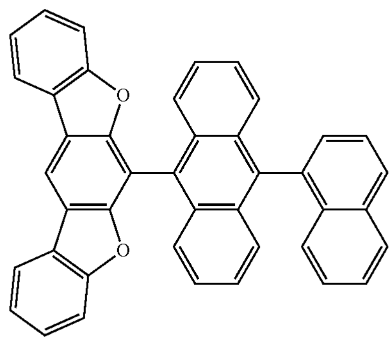
H58
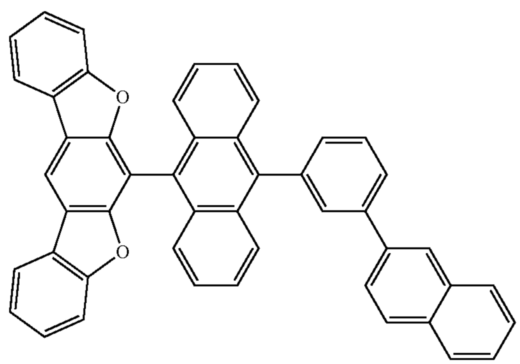
H59
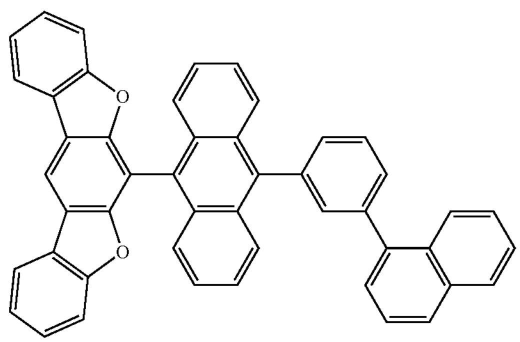

-continued
H60
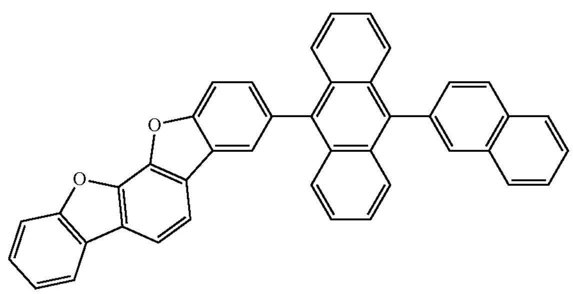
H61
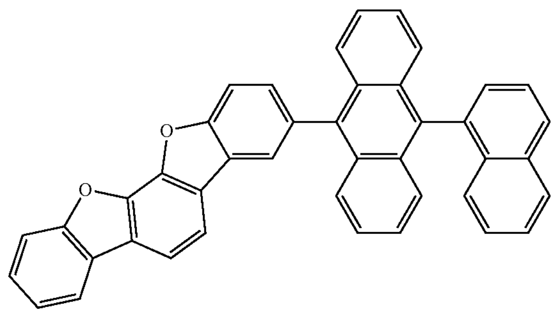
H62
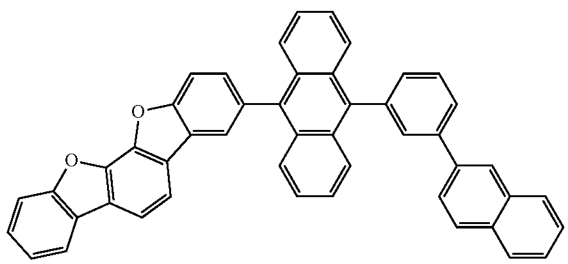
H63
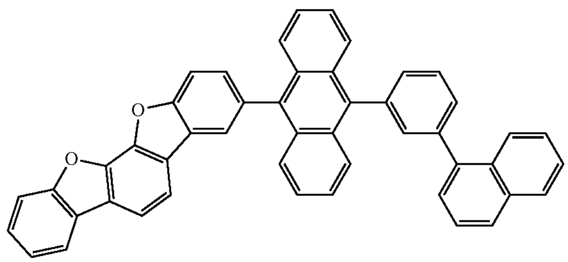
H64
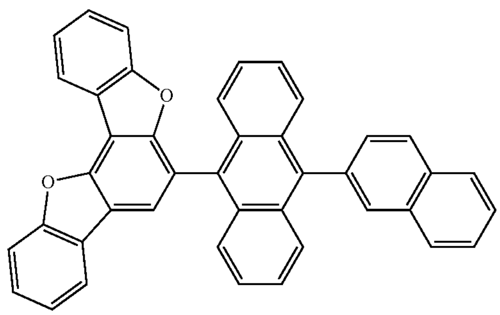
-continued
H65
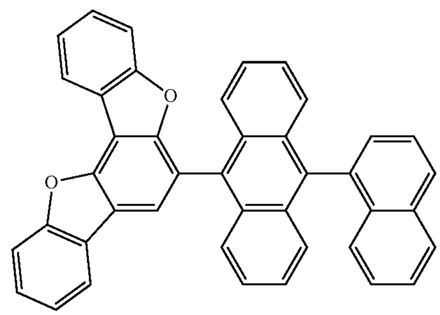
H66
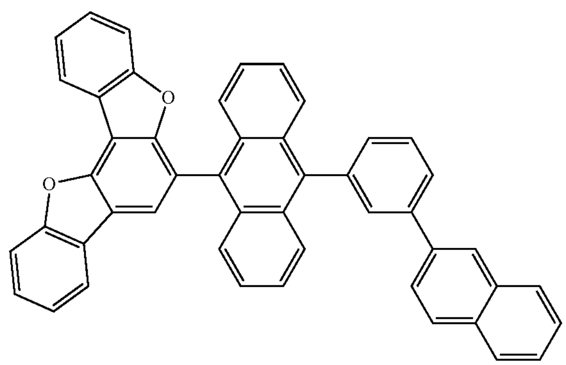
H67
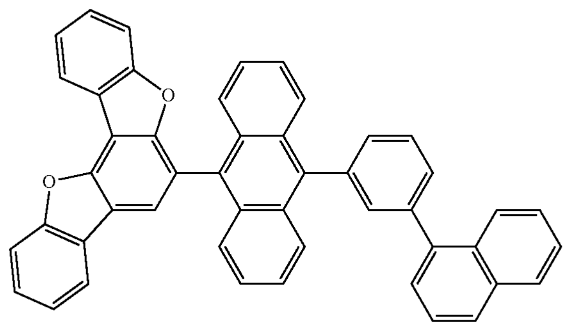
H68
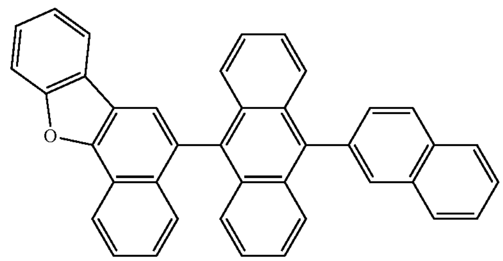
H69
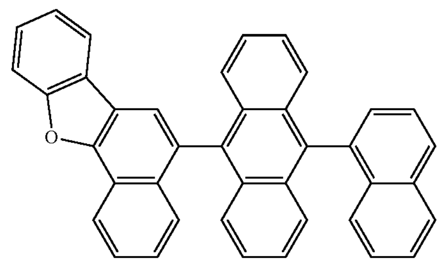

-continued
H70
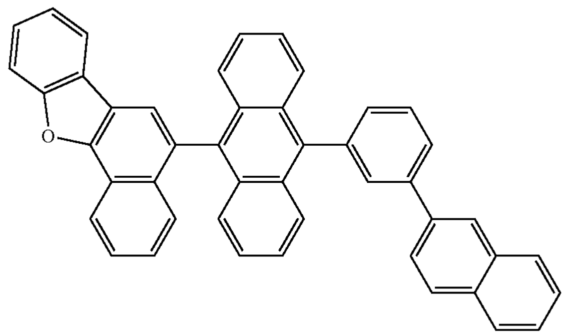
H71
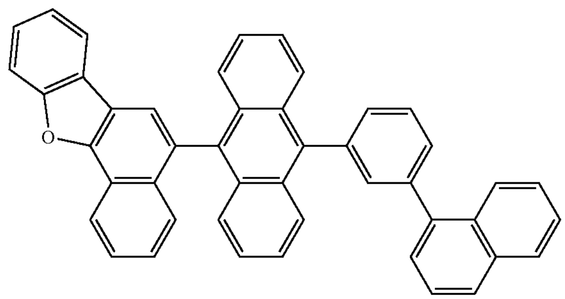
H72
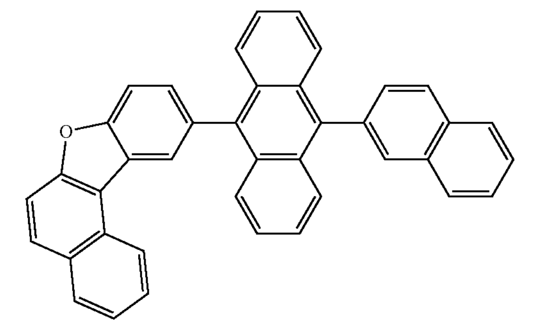
H73
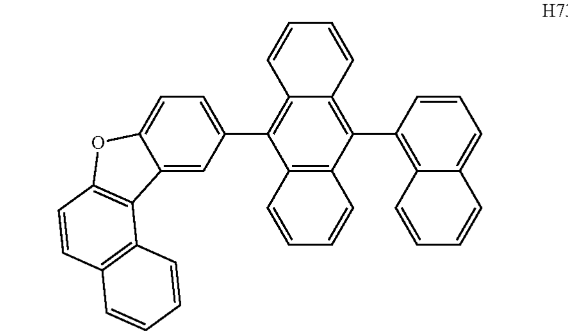
-continued
H74
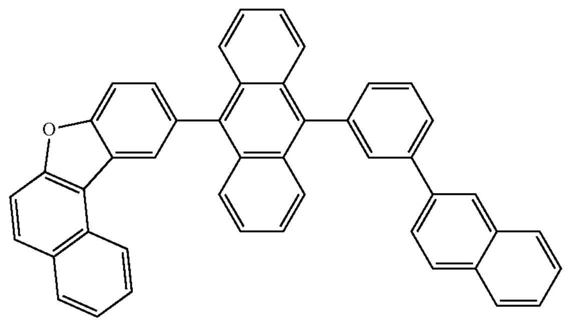
H75
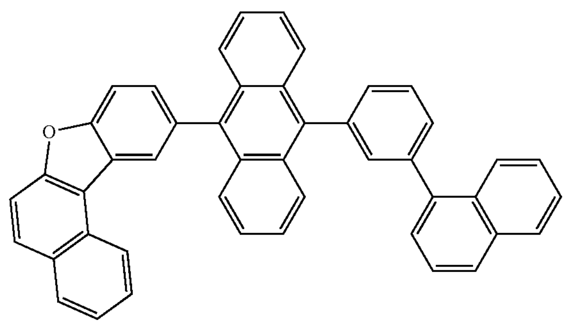
H76
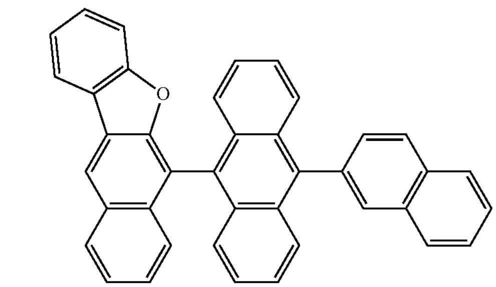
H77
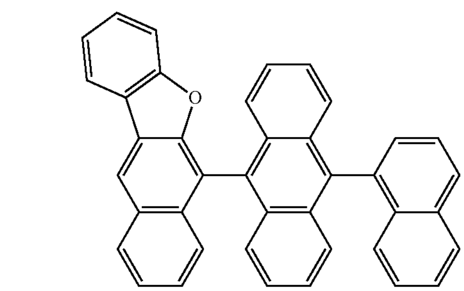
H78
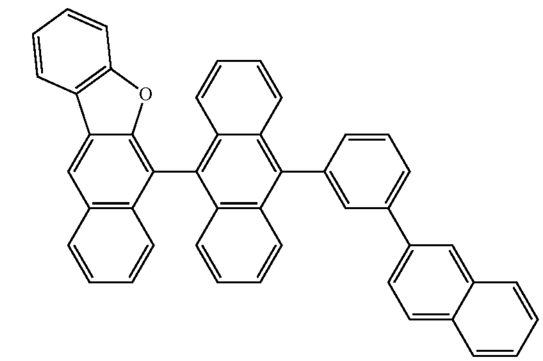

-continued
H79
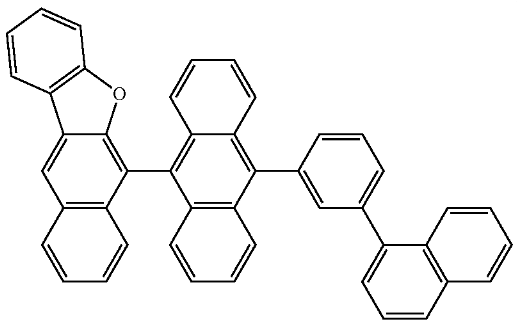
H80
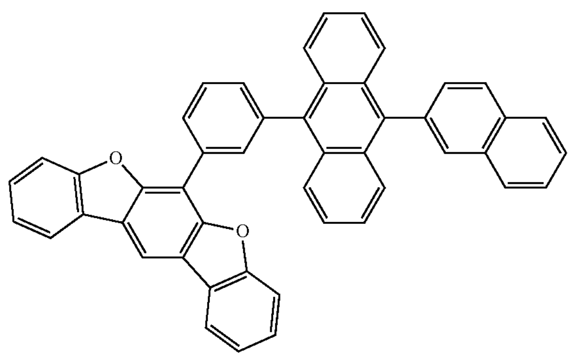
H81
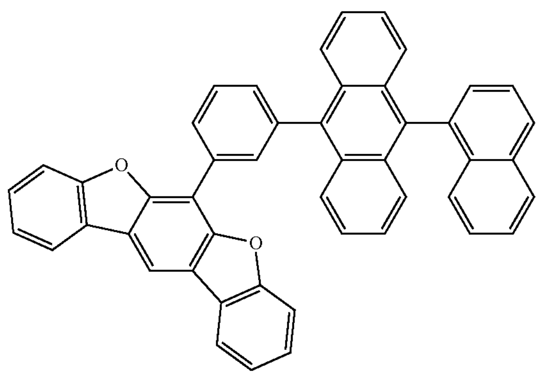
H82
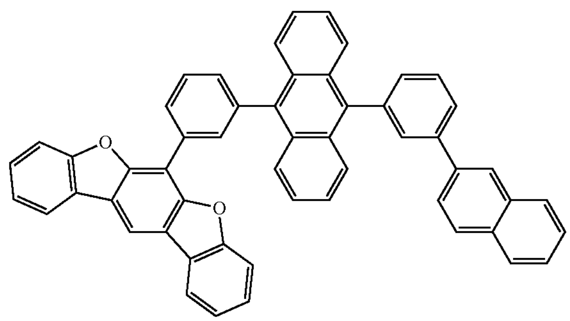
-continued
H83
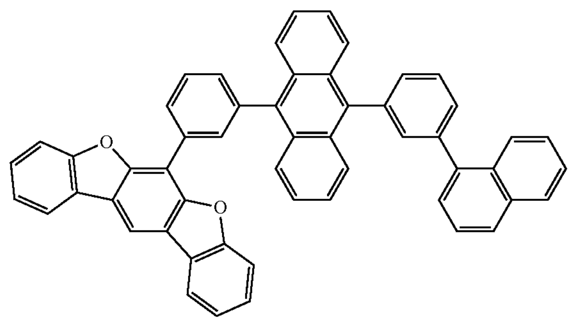
H84
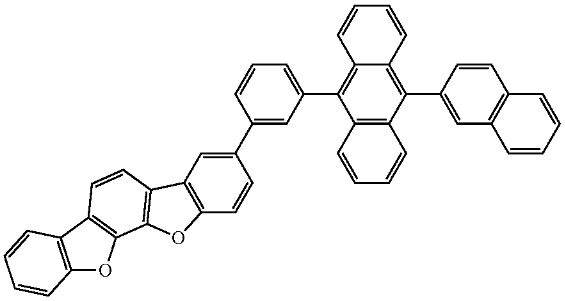
H85
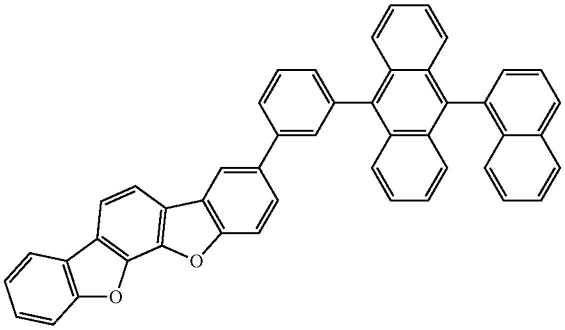
H86
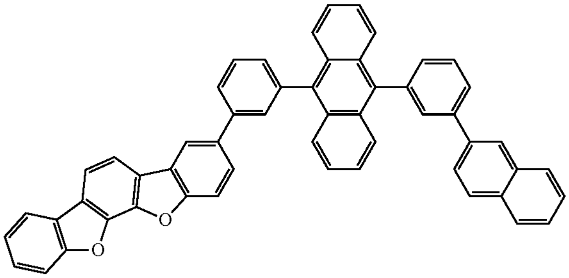
H87
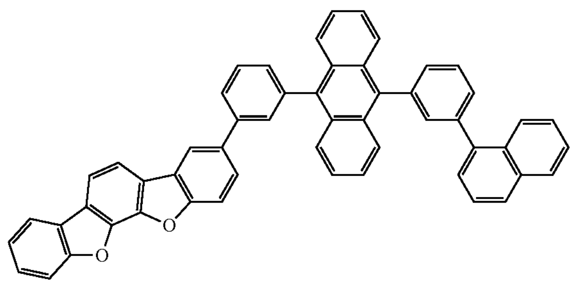

H88
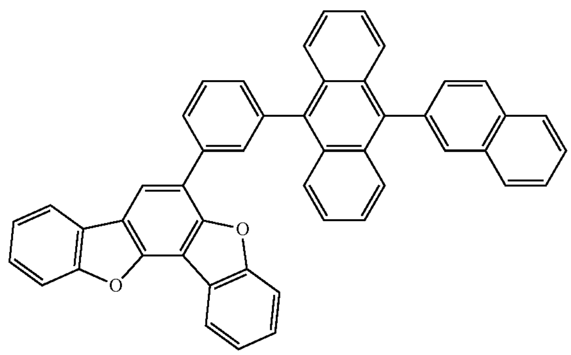
H89
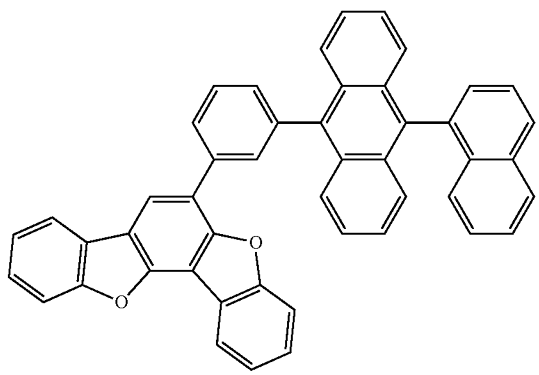
H90
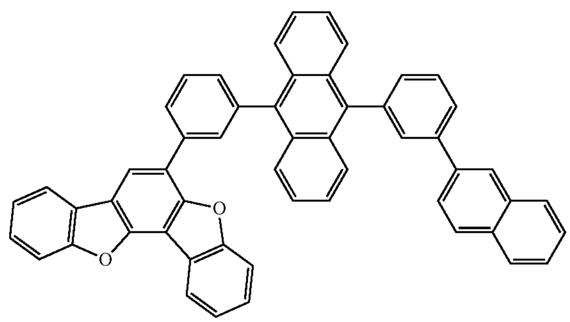
H91
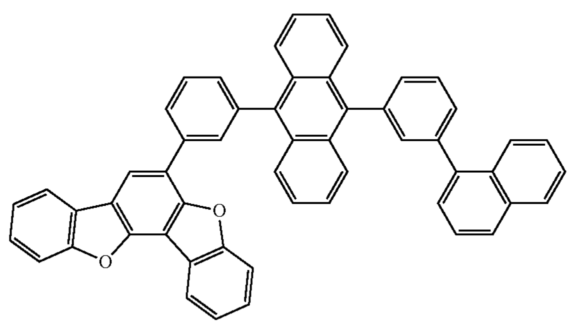
H92
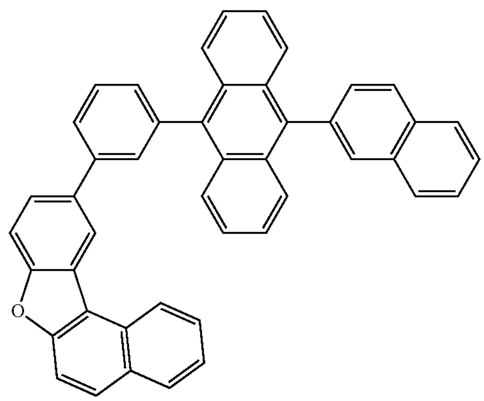
H93
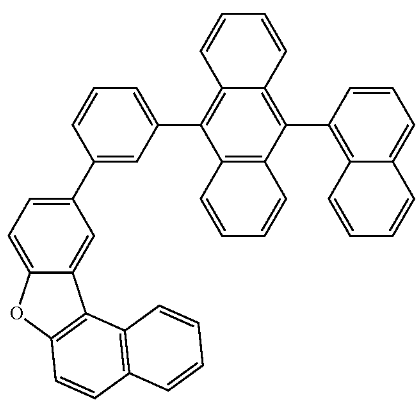
H94
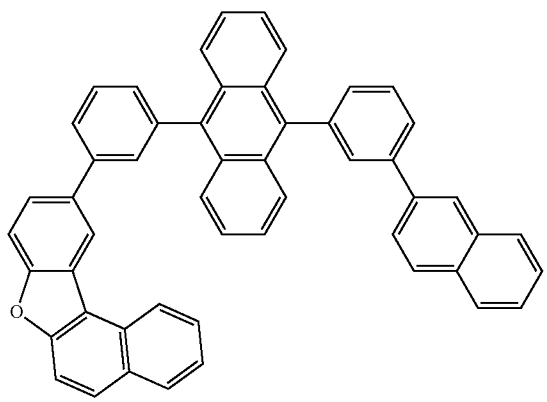
H95
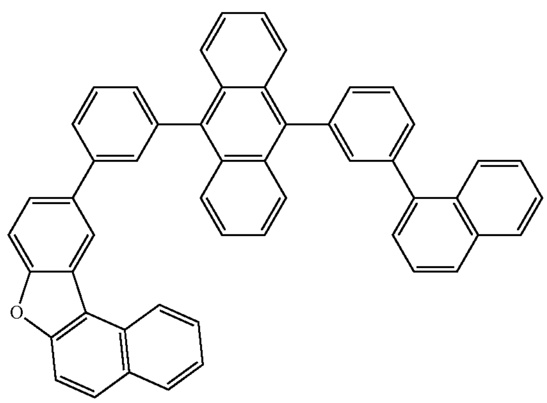

-continued
H96
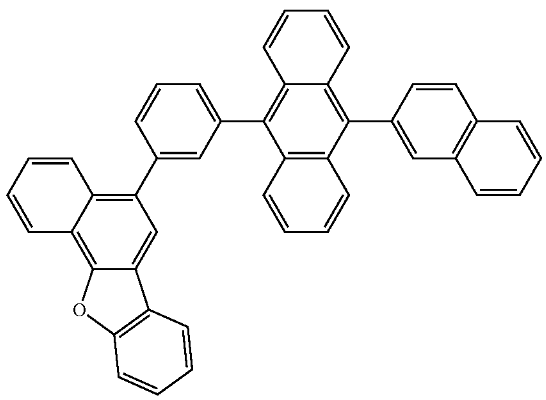
H97
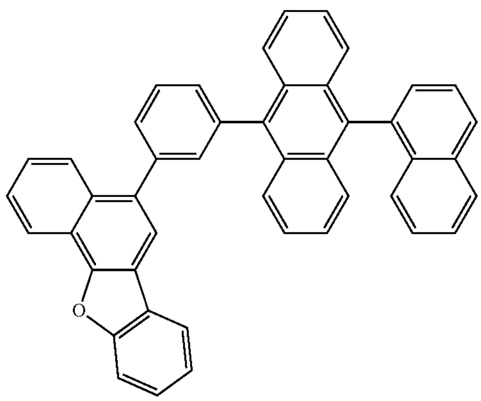
H98
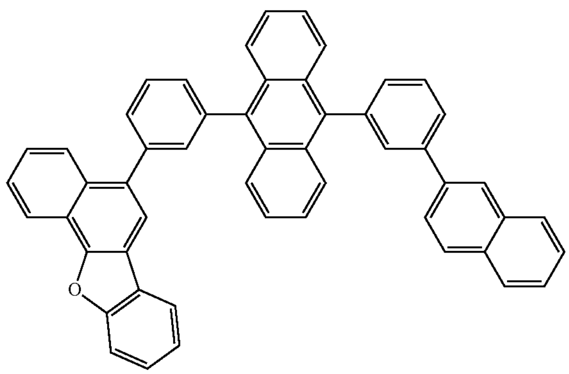
H99
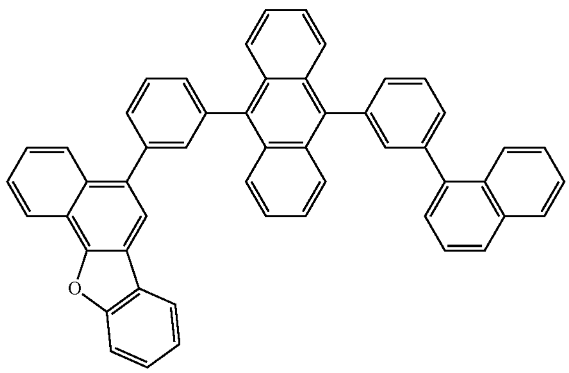
-continued
H100
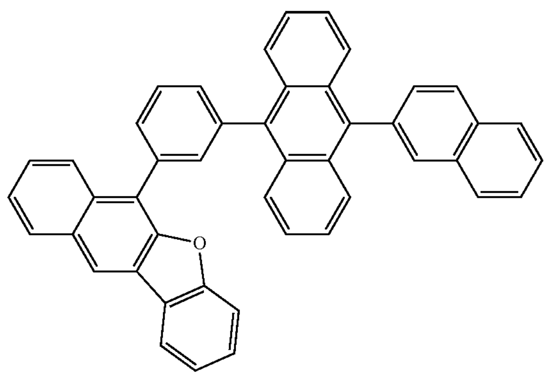
H101
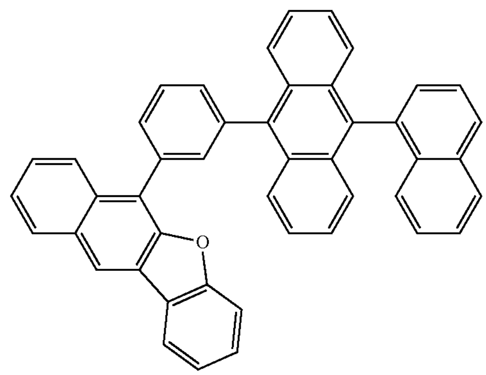
H102
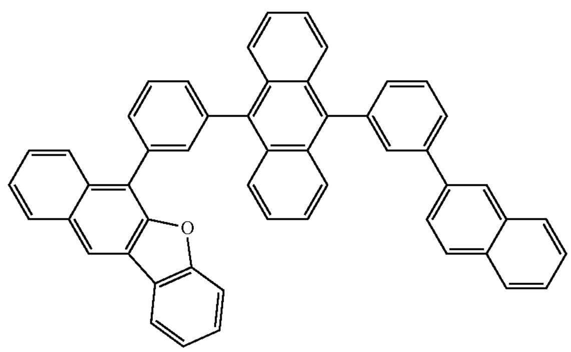
H103
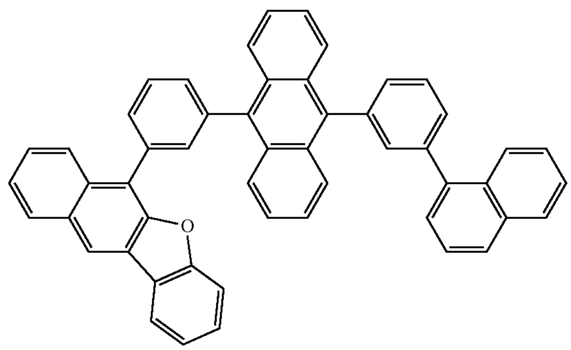

-continued
H104
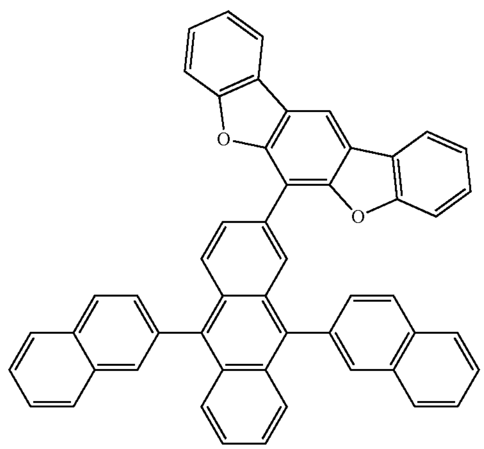
H105
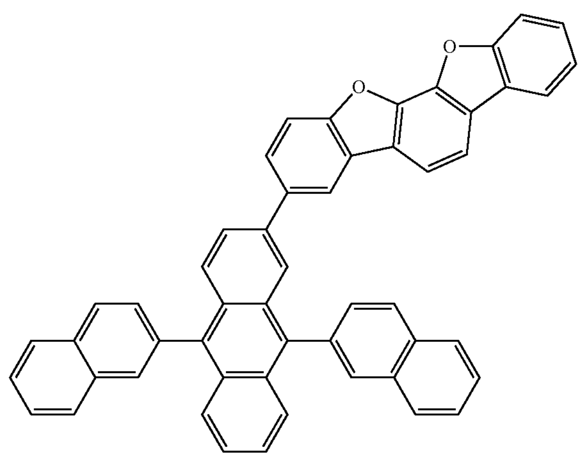
H106
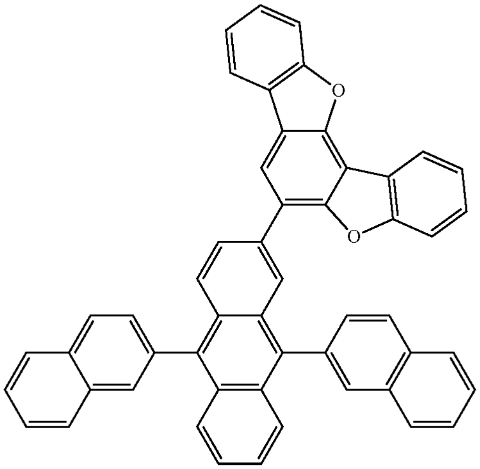
-continued
H107
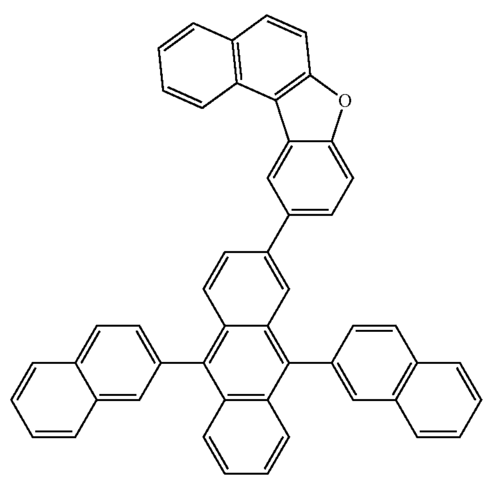
H108
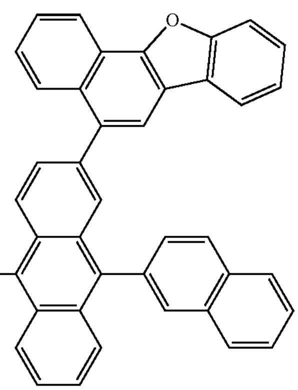
H109
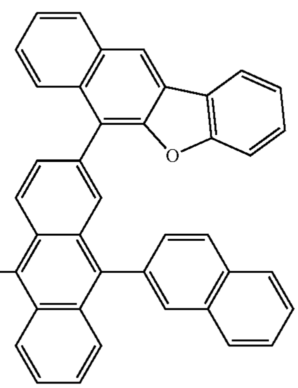
H110
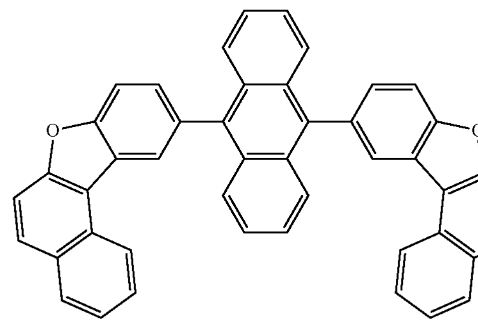

-continued
H111
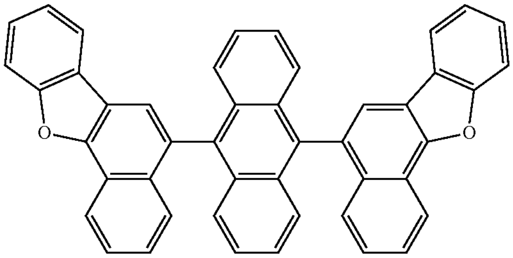
H112
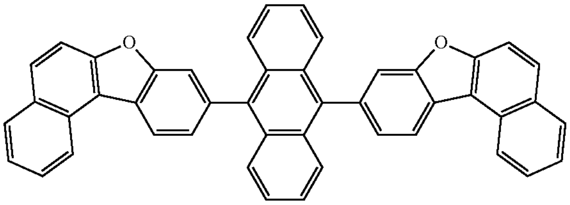
H113
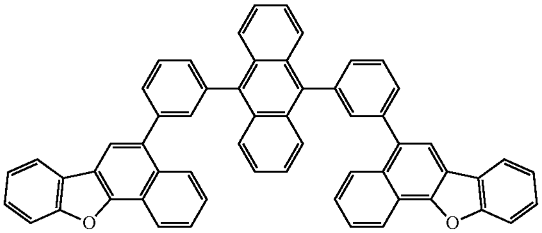
H114
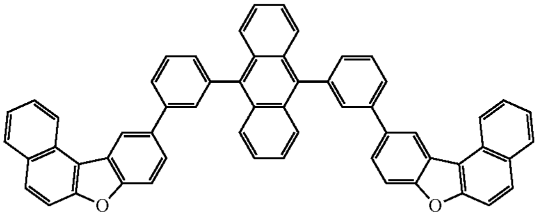
H115
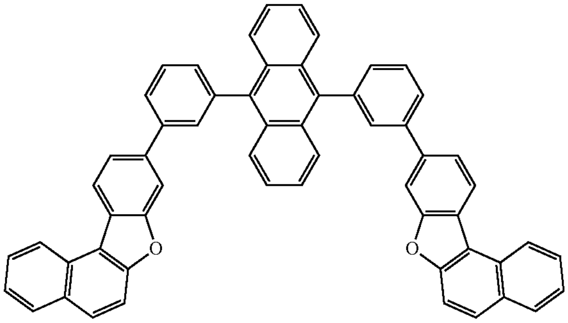
-continued
H116
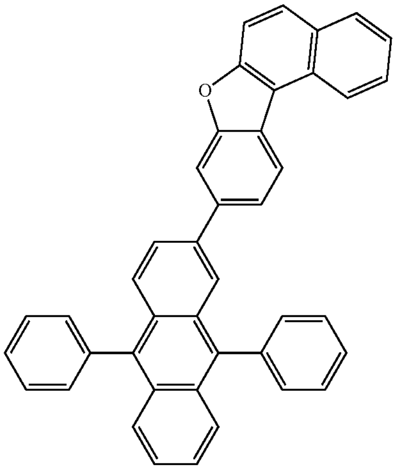
H117
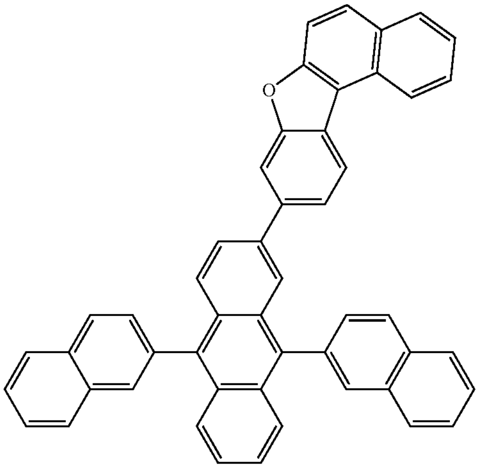
H118
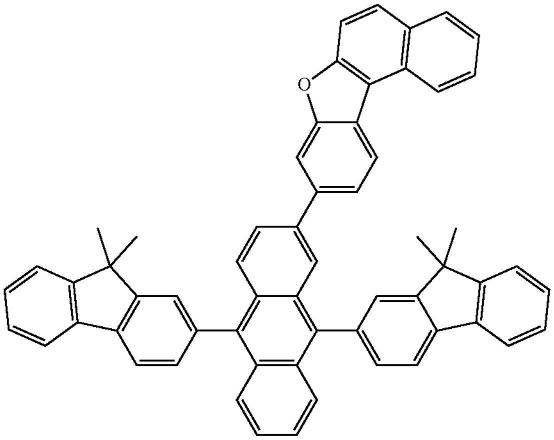

-continued

H119

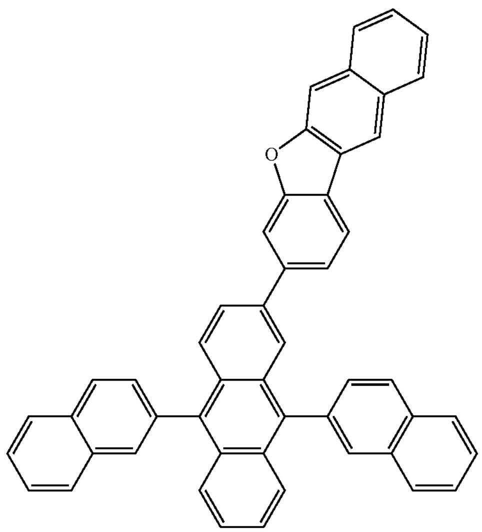

H120

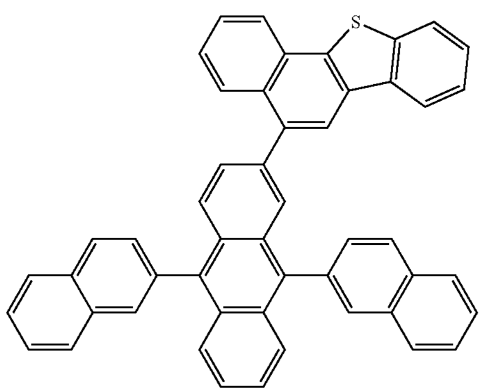

H121

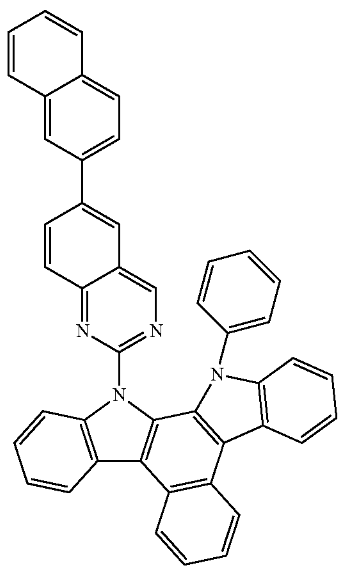

-continued

H122

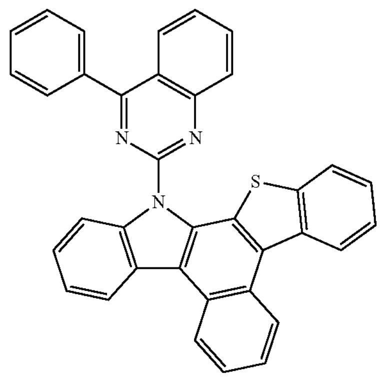

H123

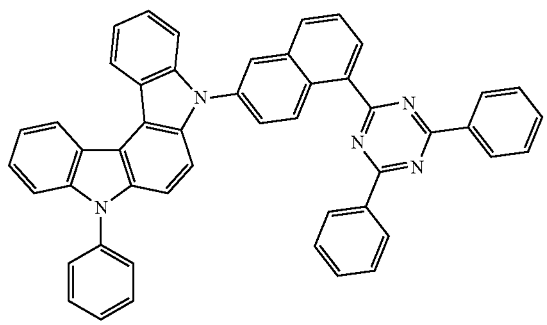

H124

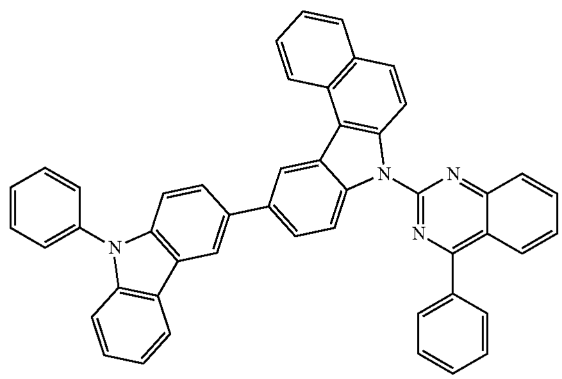

[Phosphorescent Dopant]

In one or more embodiments, the phosphorescent dopant may include at least one transition metal as a central metal.

The phosphorescent dopant may include a monodentate ligand, a bidentate ligand, a tridentate ligand, a tetradentate ligand, a pentadentate ligand, a hexadentate ligand, or any combination thereof.

The phosphorescent dopant may be electrically neutral.

For example, the phosphorescent dopant may include an organometallic compound represented by Formula 401:

Formula 401

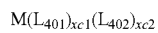

Formula 402

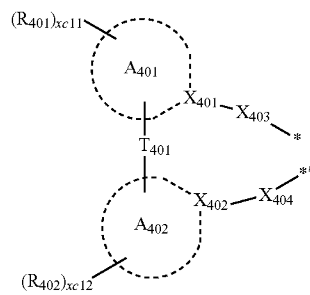

In Formulae 401 and 402,

M may be transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, wherein when xc1 is two or more, two or more of $L_{401}$(s) may be identical to or different from each other, $L_{402}$ may be an organic ligand, and xc2 may be 0, 1, 2, 3, or 4, and when xc2 is 2 or more, two or more of $L_{402}$(s) may be identical to or different from each other, $X_{401}$ and $X_{402}$ may each independently be nitrogen or carbon, ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—*', *—S—*', *—C(═O)—*', *—N($Q_{411}$)-*', *—C($Q_{411}$)($Q_{412}$)-*', *—C($Q_{411}$)═C($Q_{412}$)-*', *—C($Q_{411}$)═*', or *═C═*', $X_{403}$ and $X_{404}$ may each independently be a chemical bond (for example, a covalent bond or a coordination bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ are the same as described in connection with $Q_1$, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(═O)($Q_{401}$), —S(═O)$_2$($Q_{401}$), or —P(═O)($Q_{401}$)($Q_{402}$), $Q_{401}$ to $Q_{403}$ are the same as described in connection with $Q_1$, xc11 and xc12 may each independently be an integer from 0 to 10, $R_{10a}$ may be understood by referring to the previous description of $R_{10a}$ provided above, and

* and *' in $T_{401}$ each indicate a binding site to a neighboring atom, and * and *' in Formula 402 each indicates a binding site to M in Formula 401.

For example, in Formula 402, i) $X_{401}$ is nitrogen, and $X_{402}$ is carbon, or ii) each of $X_{401}$ and $X_{402}$ is nitrogen.

In one or more embodiments, when xc1 in Formula 401 is 2 or more, two ring $A_{401}$ in two or more of $L_{401}$(s) may be optionally linked to each other via $T_{402}$, which is a linking group, and two ring $A_{402}$ are optionally linked to each other via $T_{403}$, which is a linking group (see Compounds PD1 to PD4 and PD7). $T_{402}$ and $T_{403}$ are the same as described in connection with $T_{401}$.

$L_{402}$ in Formula 401 may be an organic ligand. For example, $L_{402}$ may include a halogen group, a diketone group (for example, an acetylacetonate group), a carboxylic acid group (for example, a picolinate group), —C(═O), an isonitrile group, —CN group, a phosphorus-containing group (for example, a phosphine group, a phosphite group, etc.), or any combination thereof.

The phosphorescent dopant may include, for example, one of compounds PD1 to PD25, or any combination thereof.

PD1

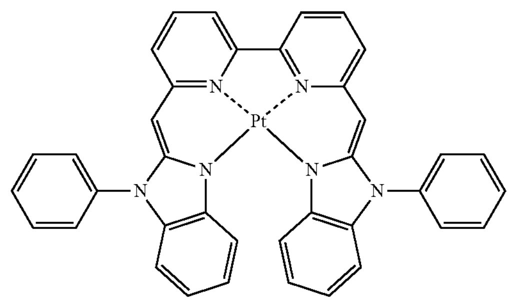

PD2

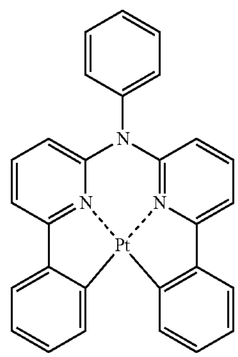

PD3

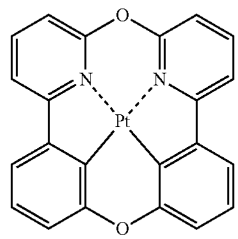

-continued
PD4
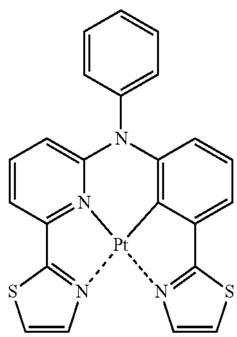
PD5
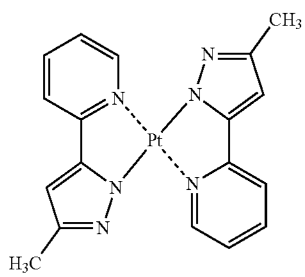
PD6
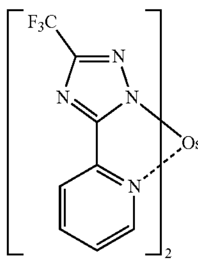
PD7
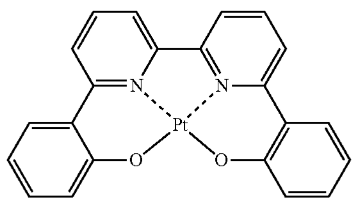
PD8
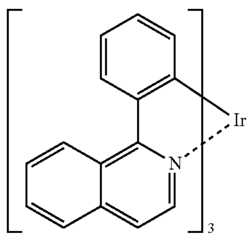
PD9
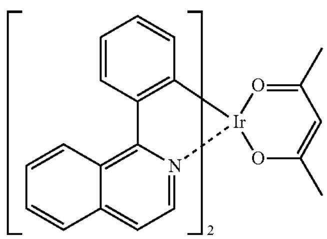
-continued
PD10
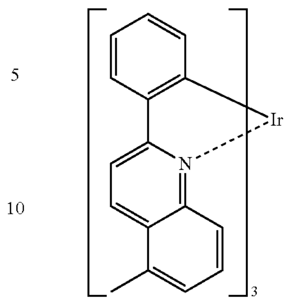
PD11
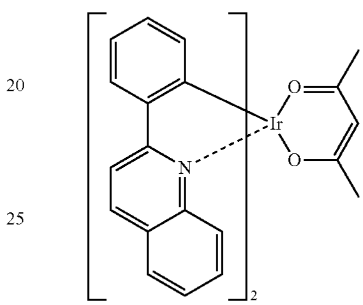
PD12
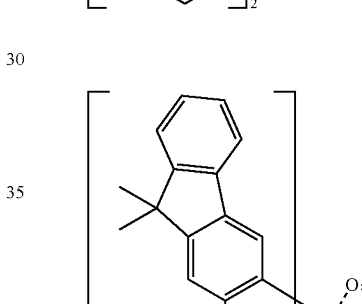
PD13
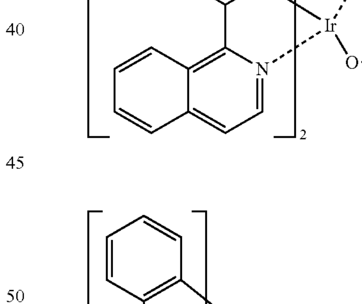
PD14
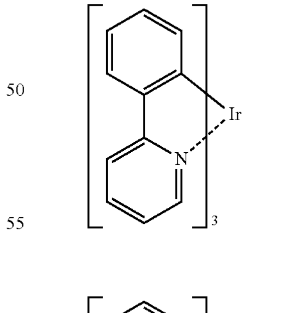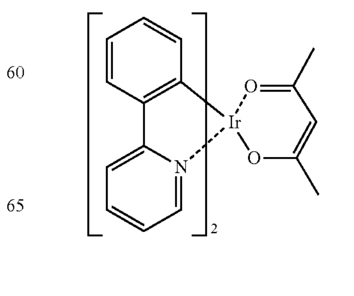

-continued
PD15
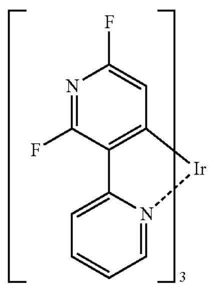
PD16
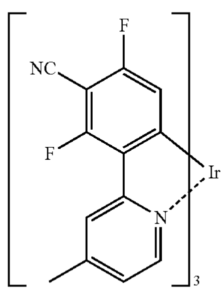
PD17
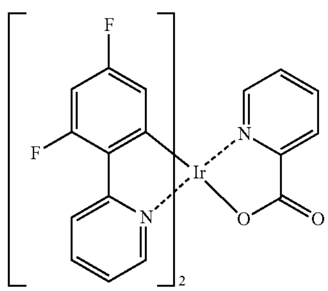
PD18
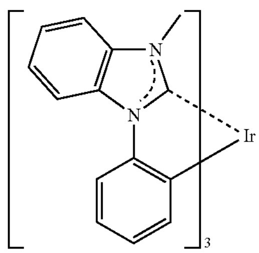
PD19
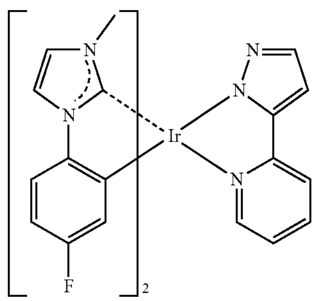
-continued
PD20
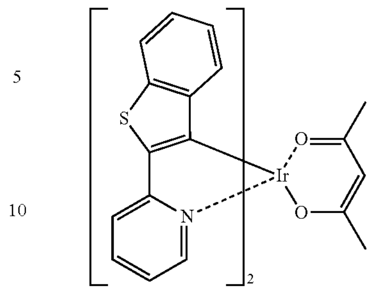
PD21
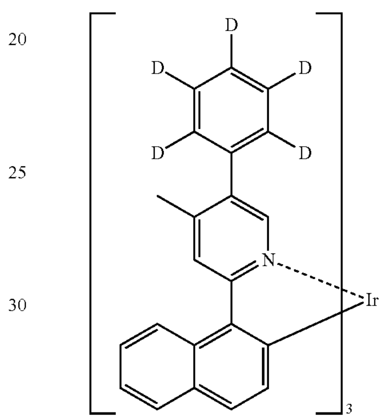
PD22
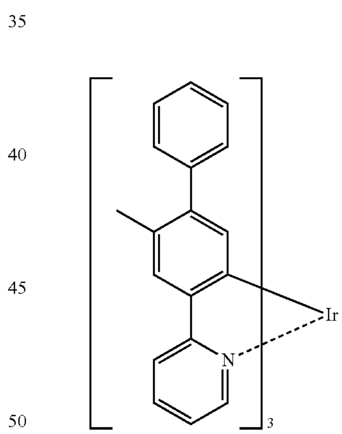
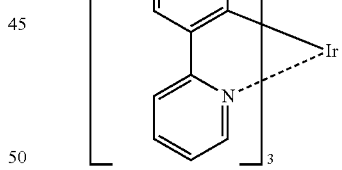
PD23
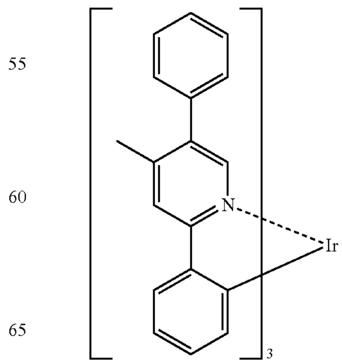

-continued

PD24

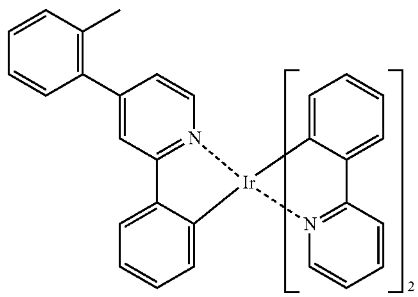

PD25

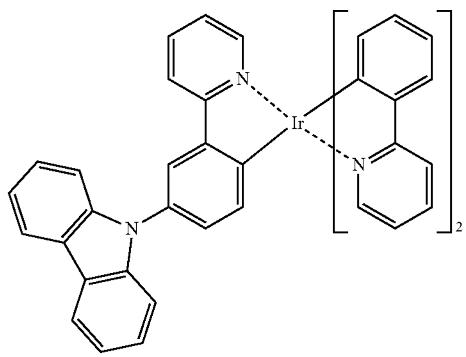

[Fluorescent Dopant]

The fluorescent dopant may include an amine group-containing compound, a styryl group-containing compound, or any combination thereof.

In one of more embodiments, the fluorescent dopant may include a compound represented by Formula 501:

Formula 501

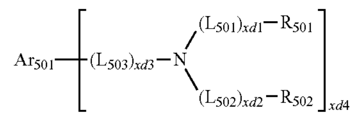

wherein, in Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xd1 to xd3 may each independently be 0, 1, 2, or 3, xd4 may be 1, 2, 3, 4, 5, or 6, $R_{10a}$ may be understood by referring to the previous description of $R_{10a}$ provided above.

In one or more embodiments, $Ar_{501}$ in Formula 501 may be a condensed cyclic group (for example, an anthracene group, a chrysene group, or a pyrene group) in which three or more monocyclic groups are condensed together.

In one or more embodiments, xd4 in Formula 501 may be 2.

In one or more embodiments, the fluorescent dopant may include: one of Compounds FD1 to FD36; DPVBi; DPAVBi; or any combination thereof.

FD1

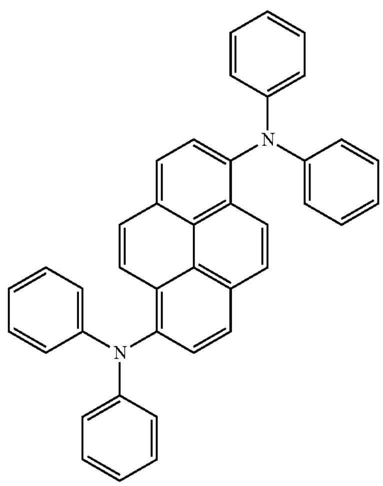

FD2

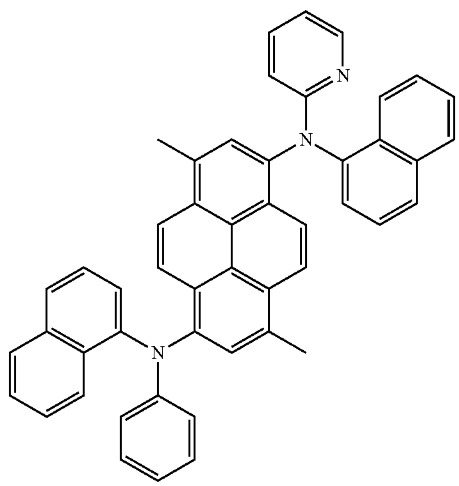

-continued
FD3
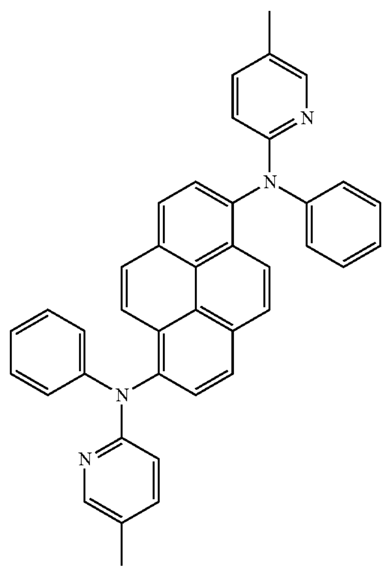
FD4
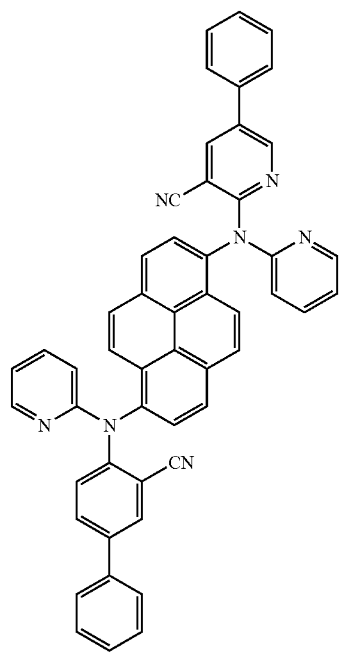
FD5
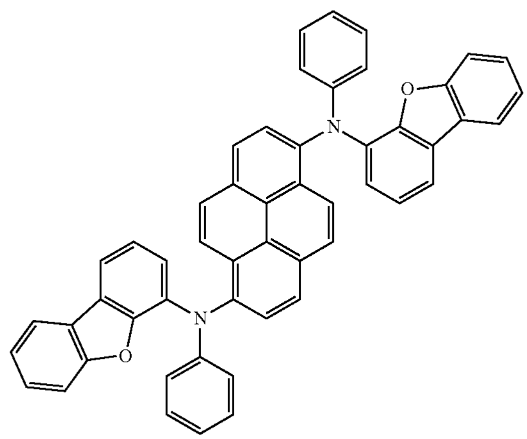
FD6
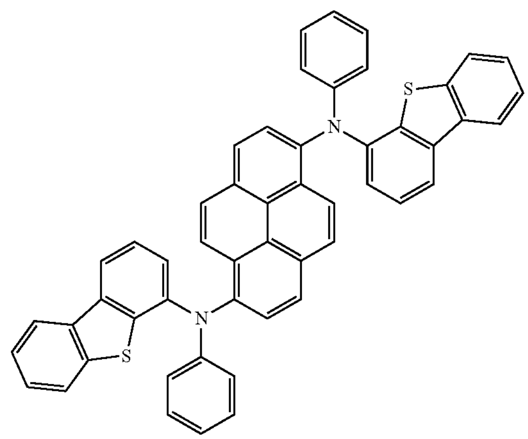

-continued
FD7
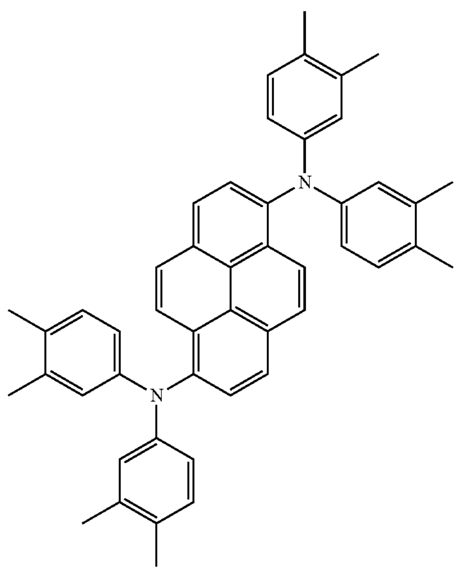
FD8
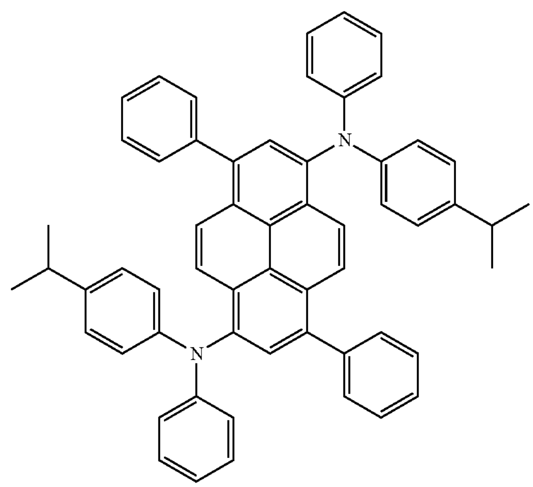
FD9
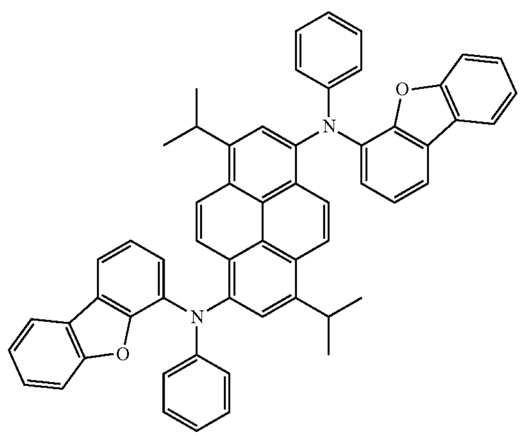
FD10
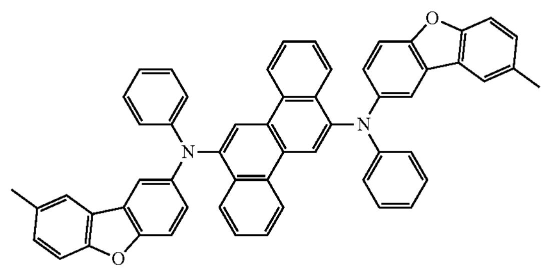
FD11
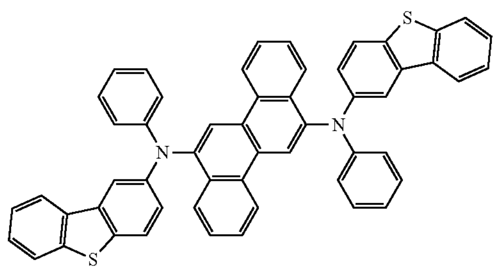
FD12
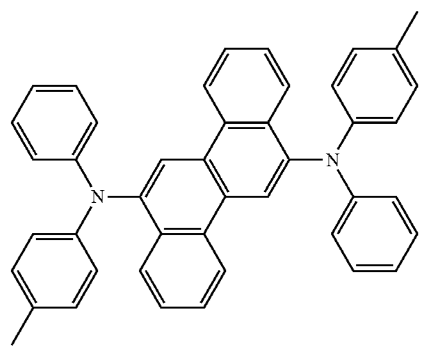
FD13
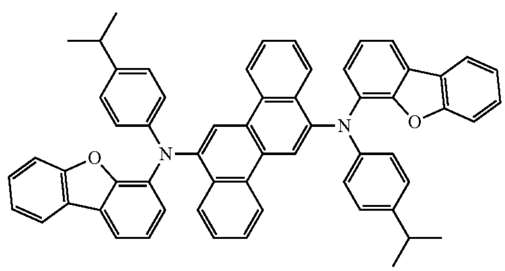
FD14
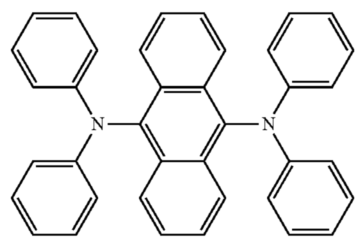

-continued
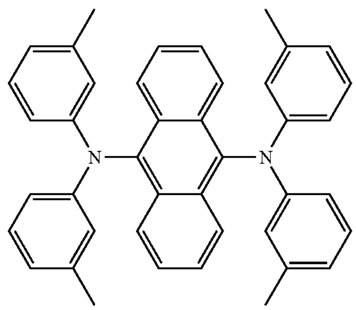
FD15
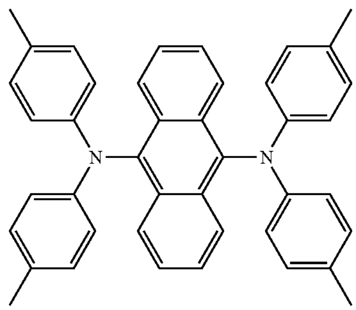
FD16
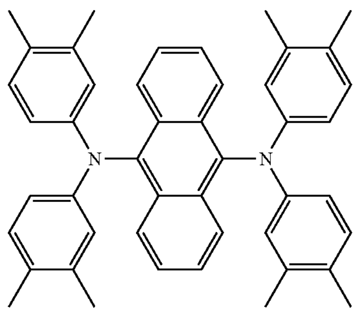
FD17
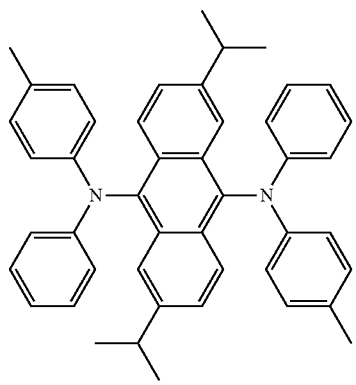
FD18
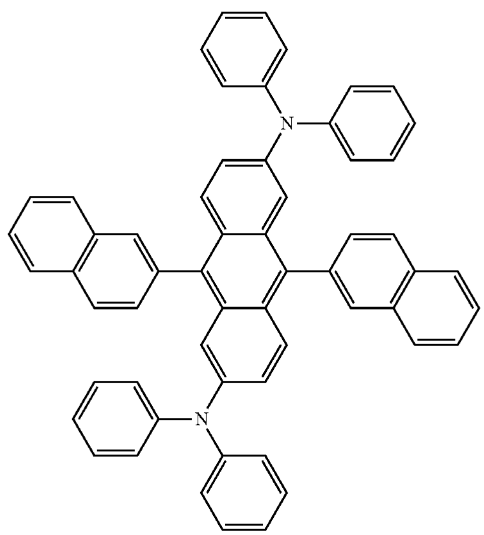
FD19
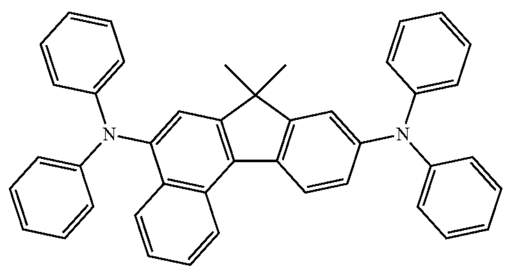
FD20
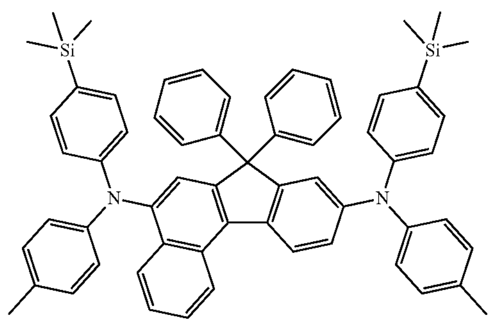
FD21
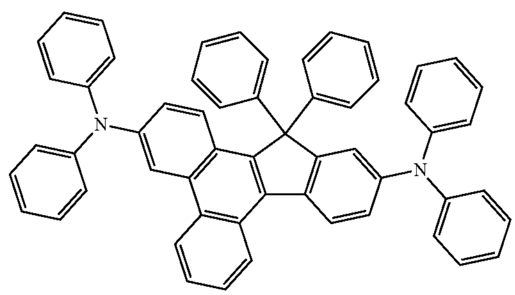
FD22

-continued
FD23
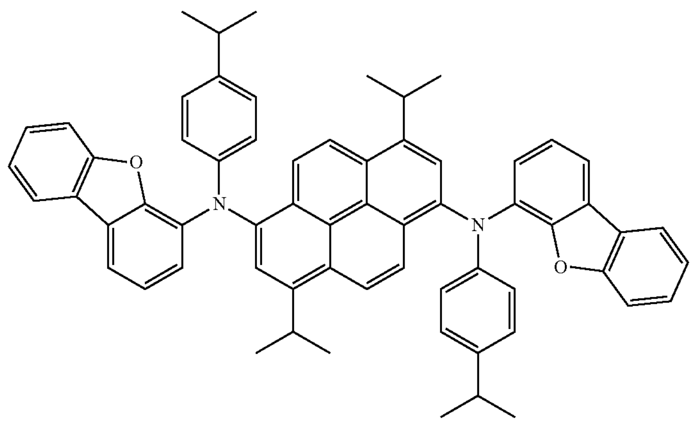
FD24
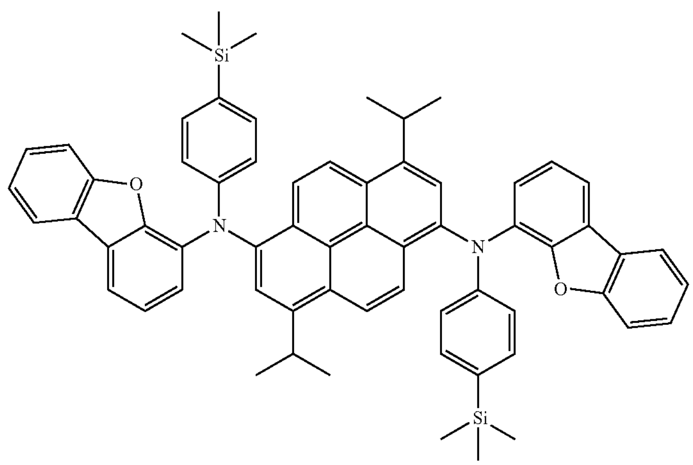
FD25
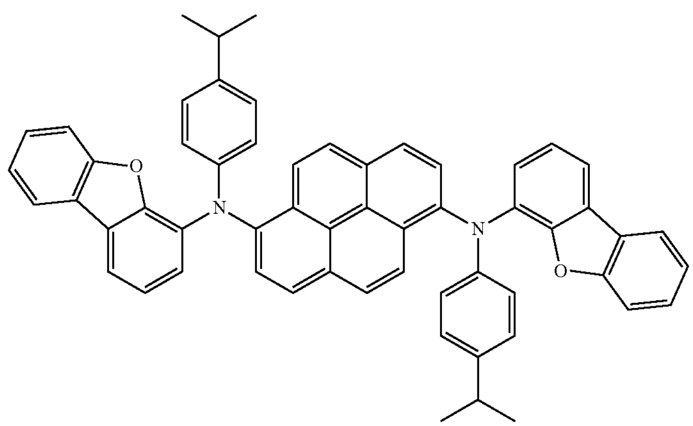

-continued
FD26
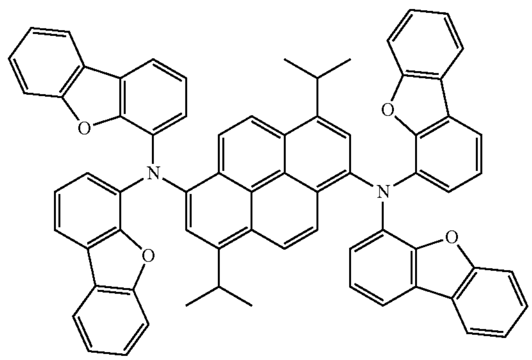
FD27
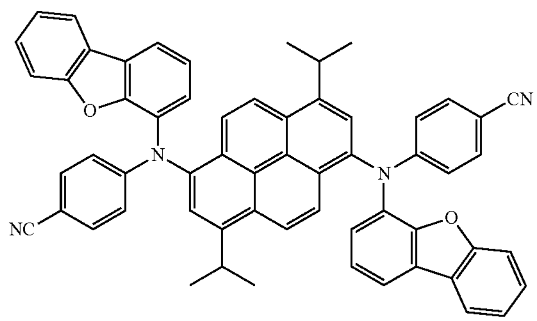
FD28
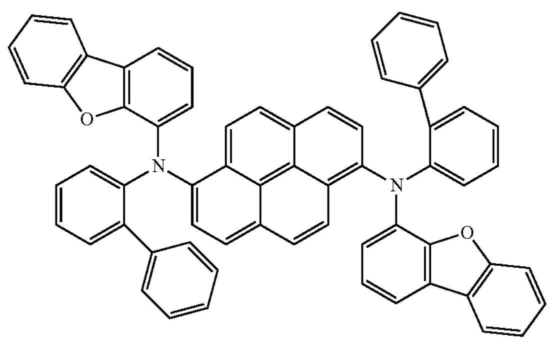
FD29
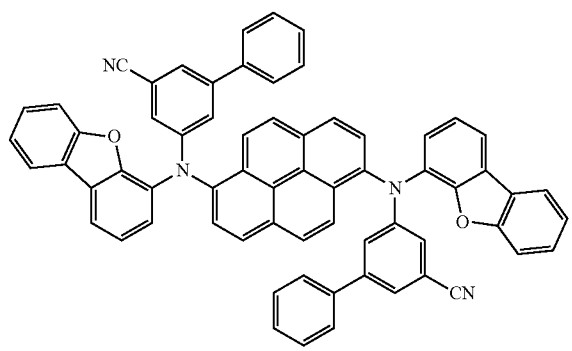
FD30
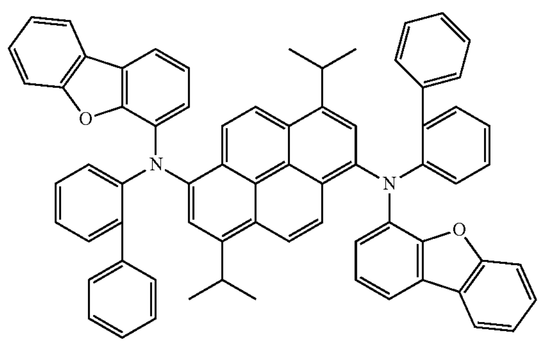
FD31
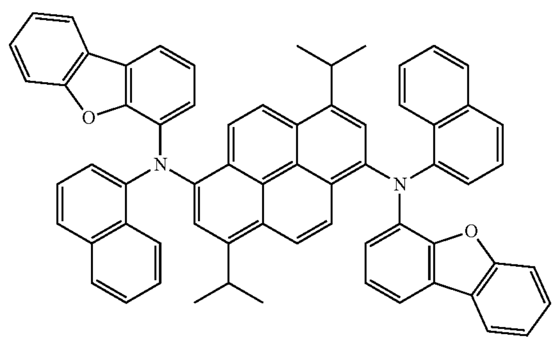
FD32
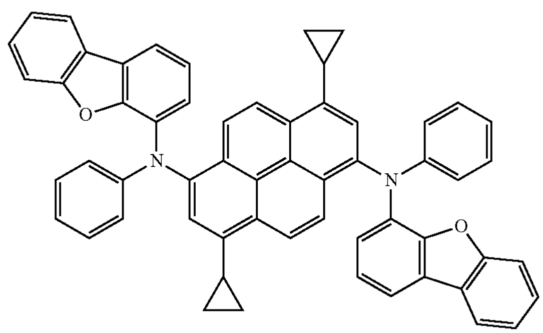
FD33
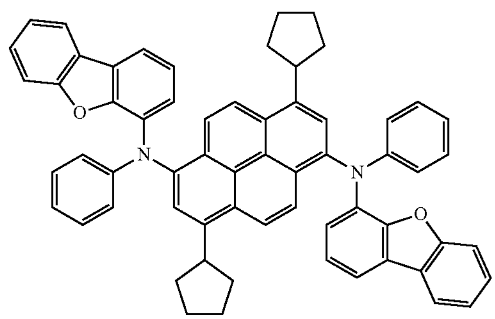

-continued
FD28
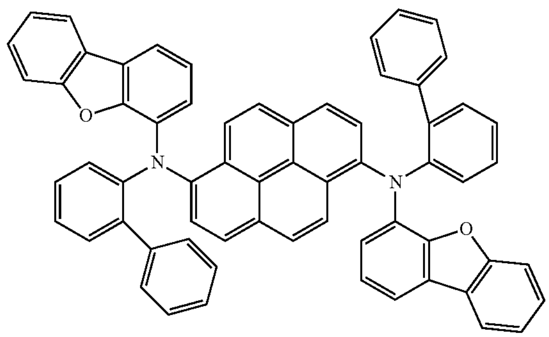
FD29
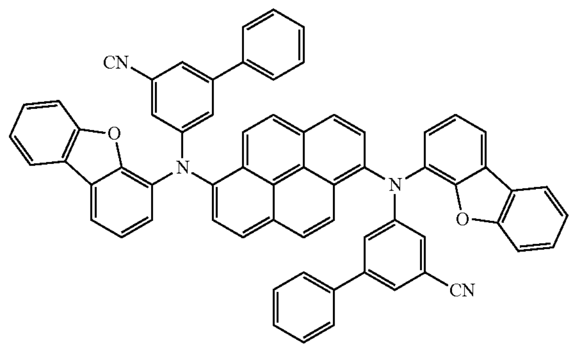
FD30
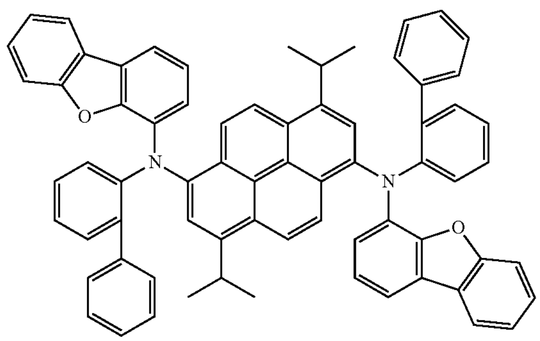
FD31
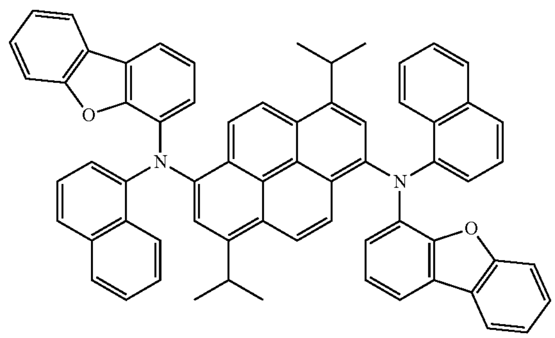
FD32
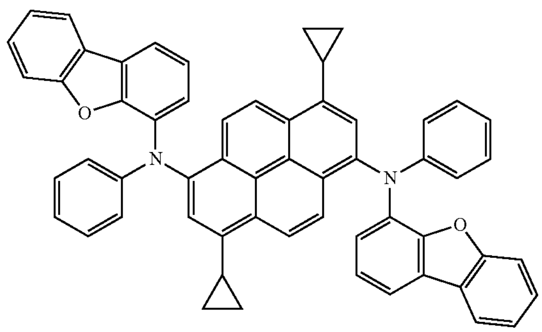
FD33
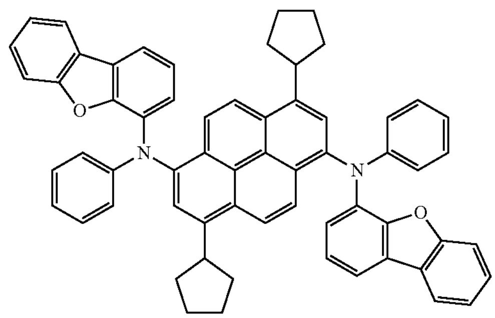
FD34
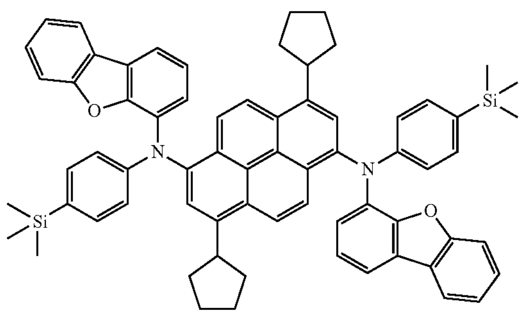
FD35
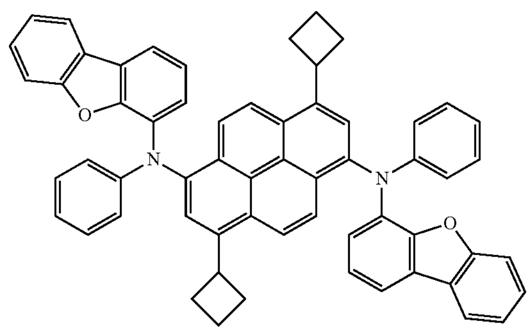

-continued

FD36

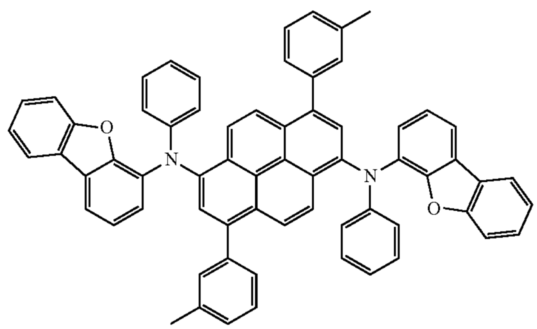

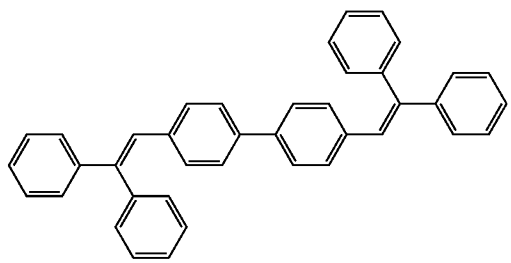

DPVBi

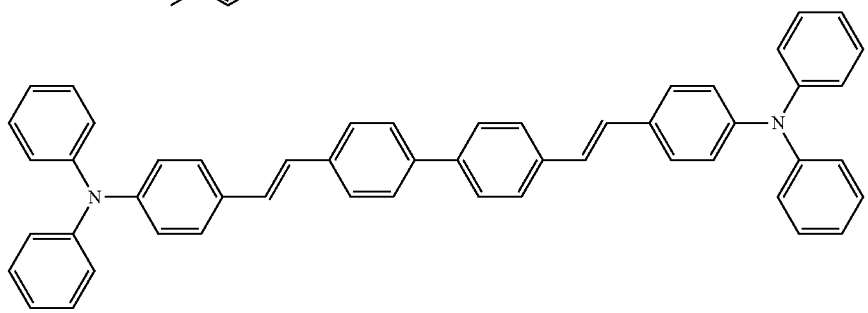

DPAVBi

[Delayed Fluorescence Material]

The emission layer may include a delayed fluorescence material.

In the present specification, the delayed fluorescence material may be selected from compounds capable of emitting delayed fluorescence based on a delayed fluorescence emission mechanism.

The delayed fluorescent material included in the emission layer may act as a host or a dopant depending on the type of other materials included in the emission layer.

In one or more embodiments, the difference between the triplet energy level (eV) of the delayed fluorescence material and the singlet energy level (eV) of the delayed fluorescence material may be greater than or equal to 0 eV and less than or equal to 0.5 eV. When the difference between the triplet energy level (eV) of the delayed fluorescent material and the singlet energy level (eV) of the delayed fluorescent material satisfies the above-described range, up-conversion from the triplet state to the singlet state of the delayed fluorescent materials may effectively occur, and thus, the luminescence efficiency of the light-emitting device 10 may be improved.

In one or more embodiments, the delayed fluorescence material may include i) a material including at least one electron donor (for example, a π electron-rich $C_3$-$C_{60}$ cyclic group, such as a carbazole group) and at least one electron acceptor (for example, a sulfoxide group, a cyano group, or a π electron-deficient nitrogen-containing $C_1$-$C_{60}$ cyclic group), and ii) a material including a $C_8$-$C_{60}$ polycyclic group in which two or more cyclic groups are condensed while sharing boron (B).

In one or more embodiments, the delayed fluorescence material may include at least one of the following compounds DF1 to DF9:

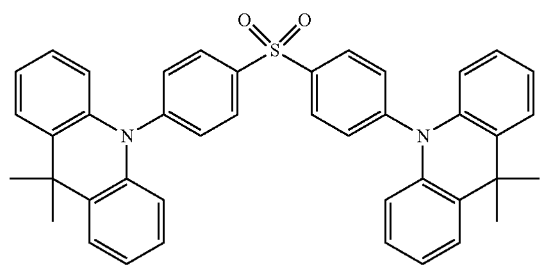

DF1(DMAC-DPS)

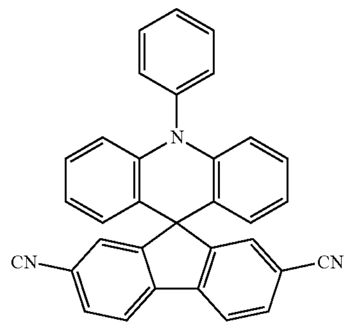

DF2(ACRFLCN)

-continued

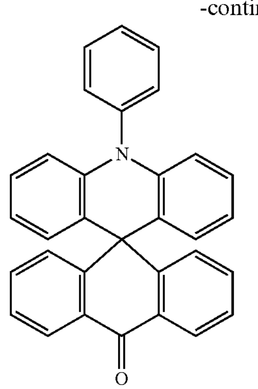

DF3(ACRSA)

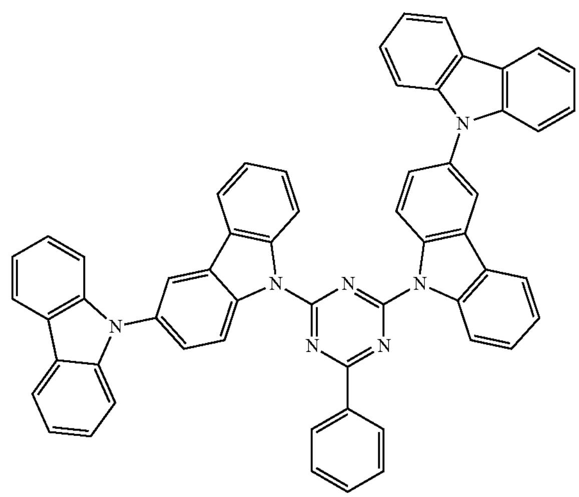

DF4(CC2TA)

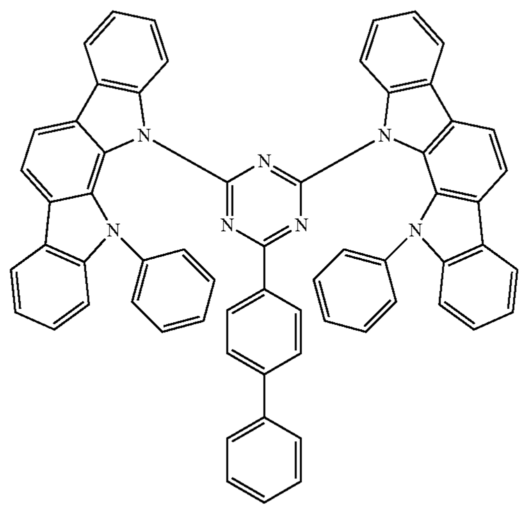

DF5(PIC-TRZ)

-continued

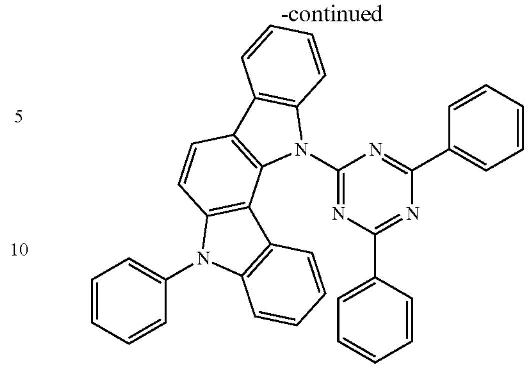

DF6(PIC-TRZ2)

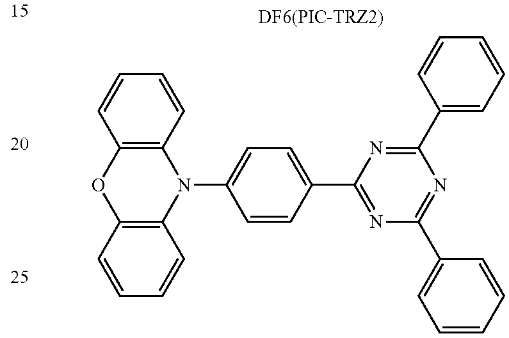

DF7(PXZ-TRZ)

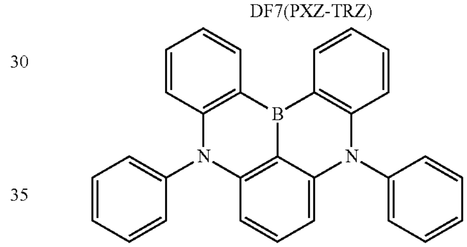

DF8(DABNA-1)

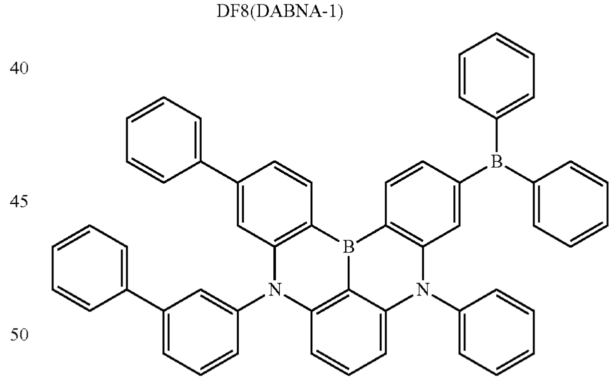

DF9(DABNA-2)

[Quantum Dot]

The emission layer may include a quantum dot.

In the present specification, a quantum dot refers to a crystal of a semiconductor compound, and may include any material capable of emitting light of various emission wavelengths according to the size of the crystal.

A diameter of the quantum dot may be, for example, in a range of about 1 nm to about 10 nm.

The quantum dot may be synthesized by a wet chemical process, a metal organic chemical vapor deposition process, a molecular beam epitaxy process, or any process similar thereto.

According to the wet chemical process, a precursor material is mixed with an organic solvent to grow a quantum dot particle crystal. When the crystal grows, the organic solvent naturally acts as a dispersant coordinated on the surface of the quantum dot crystal and controls the growth of the crystal so that the growth of quantum dot particles can be controlled through a process which is more easily performed than vapor deposition methods, such as metal organic chemical vapor deposition (MOCVD) or molecular beam epitaxy (MBE), and which requires low costs.

The quantum dot may include Group II-VI semiconductor compounds, Group III-V semiconductor compounds, Group III-VI semiconductor compounds, Group I-III-VI semiconductor compounds, Group IV-VI semiconductor compounds, a Group IV element or compound; or any combination thereof.

Examples of the Group II-VI semiconductor compound are a binary compound, such as CdSe, CdTe, ZnS, ZnSe, ZnTe, ZnO, HgS, HgSe, HgTe, MgSe, or MgS; a ternary compound, such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, or MgZnS; a quaternary compound, such as CdZnSeS, CdZnSeTe, CdZnSTe, CdHgSeS, CdHgSeTe, CdHgSTe, HgZnSeS, HgZnSeTe, or HgZnSTe; or any combination thereof.

Examples of the Group III-V semiconductor compound are: a binary compound, such as GaN, GaP, GaAs, GaSb, AlN, AlP, AlAs, AlSb, InN, InP, InAs, or InSb; a ternary compound, such as GaNP, GaNAs, GaNSb, GaPAs, GaPSb, AlNP, AlNAs, AlNSb, AlPAs, AlPSb, InGaP, InNP, InAlP, InNAs, InNSb, InPAs, or InPSb; a quaternary compound, such as GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, or InAlPSb; or any combination thereof. Meanwhile, the Group III-V semiconductor compound may further include Group II elements. Examples of the Groups III-V semiconductor compound further including Group II elements are InZnP, InGaZnP, InAlZnP, etc.

Examples of the Group III-VI semiconductor compound are: a binary compound, such as GaS, GaSe, $Ga_2Se_3$, GaTe, InS, InSe, $In_2S_3$, $In_2Se_3$, or InTe; a ternary compound, such as $InGaS_3$, or $InGaSe_3$; and any combination thereof.

Examples of the Group 1-III-VI semiconductor compound are: a ternary compound, such as AgInS, $AgInS_2$, CuInS, $CuInS_2$, $CuGaO_2$, $AgGaO_2$, or $AgAlO_2$; or any combination thereof.

Examples of the Group IV-VI semiconductor compound are: a binary compound, such as SnS, SnSe, SnTe, PbS, PbSe, or PbTe; a ternary compound, such as SnSeS, SnSeTe, SnSTe, PbSeS, PbSeTe, PbSTe, SnPbS, SnPbSe, or SnPbTe; a quaternary compound, such as SnPbSSe, SnPbSeTe, or SnPbSTe; or any combination thereof.

The Group IV element or compound may include: a single element material, such as Si or Ge; a binary compound, such as SiC or SiGe; or any combination thereof.

Each element included in a multi-element compound such as the binary compound, the ternary compound, and the quaternary compound, may exist at a uniform concentration or non-uniform concentration in a particle.

Meanwhile, the quantum dot may have a single structure or a core-shell dual structure. In the case of the quantum dot having a single structure, the concentration of each element included in the corresponding quantum dot may be uniform. In one or more embodiments, the material contained in the core and the material contained in the shell may be different from each other.

The shell of the quantum dot may act as a protective layer to prevent chemical degeneration of the core to maintain semiconductor characteristics and/or as a charging layer to impart electrophoretic characteristics to the quantum dot. The shell may be a single layer or a multi-layer. The interface between the core and the shell may have a concentration gradient in which the concentration of an element existing in the shell is decreased as the element is located closer to the center of the core.

Examples of the shell of the quantum dot may be an oxide of metal, metalloid, or non-metal, a semiconductor compound, and a combination thereof. Examples of the oxide of metal, metalloid, or non-metal are a binary compound, such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, or NiO; a ternary compound, such as $MgAl_2O_4$, $CoFe_2O_4$, $NiFe_2O_4$, or $CoMn_2O_4$; and any combination thereof. Examples of the semiconductor compound are, as described herein, Group II-VI semiconductor compounds; Group III-V semiconductor compounds; Group III-VI semiconductor compounds; Group 1-III-VI semiconductor compounds; Group IV-VI semiconductor compounds; and any combination thereof. In addition, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

A full width at half maximum (FWHM) of an emission wavelength spectrum of the quantum dot may be about 45 nm or less, for example, about 40 nm or less, for example, about 30 nm or less, and within these ranges, color purity or color gamut may be increased. In addition, since the light emitted through the quantum dot is emitted in all directions, the wide viewing angle may be improved.

In addition, the quantum dot may be a spherical particle, a pyramidal particle, a multi-arm particle, a cubic nanoparticle, a nanotube particle, a nanowire particle, a nanofiber particle, or a nanoplate particle.

Since the energy band gap can be adjusted by controlling the size of the quantum dot, light having various wavelength bands can be obtained from the quantum dot emission layer. Accordingly, by using quantum dots of different sizes, a light-emitting device that emits light of various wavelengths may be implemented. In one or more embodiments, the size of the quantum dot may be selected to emit red, green and/or blue light. In addition, the size of the quantum dot may be configured to emit white light by combining light of various colors.

[Electron Transport Region 136 in Interlayer 130]

As described above, the electron transport region 136 may include: the first compound represented by Formula 1, the second compound represented by Formula 2, or a combination thereof, and the metal dopant.

In an embodiment, the electron transport region 136 may include an electron transport layer, and the electron transport layer may include: the first compound, the second compound, or a combination thereof, and the metal dopant.

In an embodiment, the electron transport region 136 may further include a hole-blocking layer, an electron control layer, an electron injection layer, or a combination thereof.

In an embodiment, the electron transport region 136 may consist of the electron transport layer.

In an embodiment, the electron transport layer may be in direct contact with the second electrode 150.

In an embodiment, the electron transport layer may be in direct contact with the emission layer 135.

In an embodiment, the electron transport region may further include a compound represented by Formula 601:

Formula 601

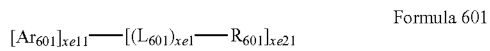

wherein, in Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, $-Si(Q_{601})(Q_{602})(Q_{603})$, $-C(=O)(Q_{601})$, $-S(=O)_2(Q_{601})$, or $-P(=O)(Q_{601})(Q_{602})$, $Q_{601}$ to $Q_{603}$ are the same as described in connection with $Q_1$, xe21 may be 1, 2, 3, 4, or 5, and at least one of $Ar_{601}$, $L_{601}$, and $R_{601}$ may each independently be a π electron-deficient nitrogen-containing $C_1$-$C_{60}$ cyclic group unsubstituted or substituted with at least one $R_{10a}$, wherein $R_{10a}$ may be understood by referring to the previous description of $R_{10a}$ provided above.

For example, when xe11 in Formula 601 is 2 or more, two or more of $Ar_{601}$(s) may be linked to each other via a single bond.

In one or more embodiments, $Ar_{601}$ in Formula 601 may be a substituted or unsubstituted anthracene group.

In an embodiment, the electron transport region may include a compound represented by Formula 601-1:

Formula 601-1

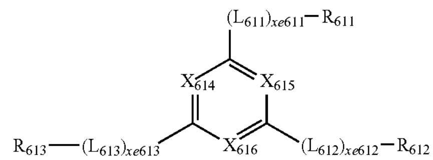

wherein, in Formula 601-1, $X_{614}$ may be N or $C(R_{614})$, $X_{615}$ may be N or $C(R_{615})$, $X_{616}$ may be N or $C(R_{616})$, at least one of $X_{614}$ to $X_{616}$ may be N, $L_{611}$ to $L_{613}$ are the same as described in connection with $L_{601}$, xe611 to xe613 are the same as described in connection with xe1, $R_{611}$ to $R_{613}$ are the same as described in connection with $R_{601}$, and $R_{614}$ to $R_{16}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, wherein $R_{10a}$ may be understood by referring to the previous description of $R_{10a}$ provided above.

For example, xe1 and xe611 to xe613 in Formulae 601 and 601-1 may each independently be 0, 1, or 2.

The electron transport region 136 may include one of Compounds ET1 to ET45, 2,9-dimethyl-4,7-diphenyl-1,10-phenanthroline (BCP), 4,7-diphenyl-1,10-phenanthroline (Bphen), $Alq_3$, BAlq, TAZ, NTAZ, or any combination thereof:

ET1

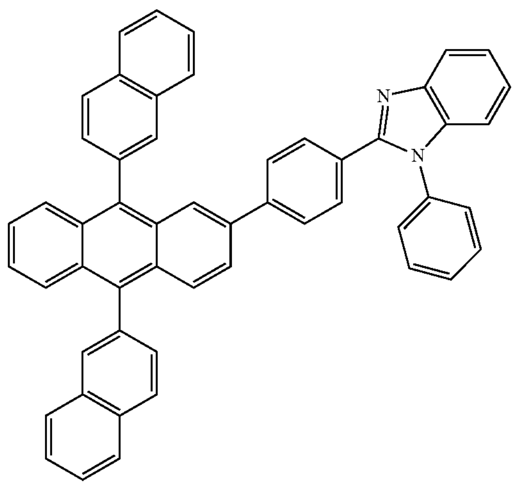

ET2

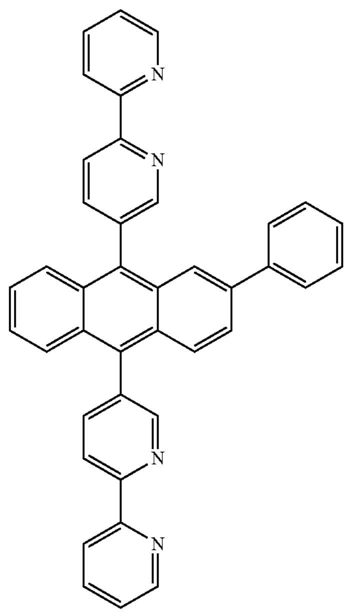

-continued
ET3
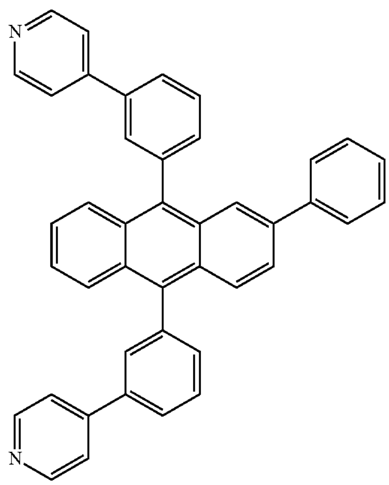
ET4
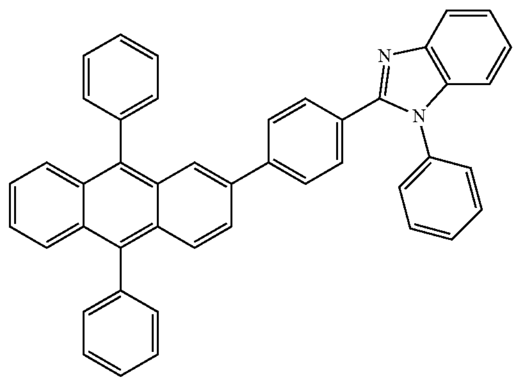
ET5
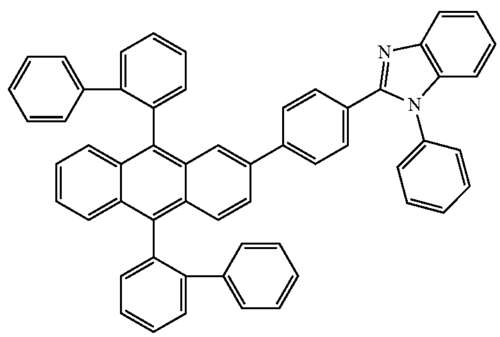
ET6
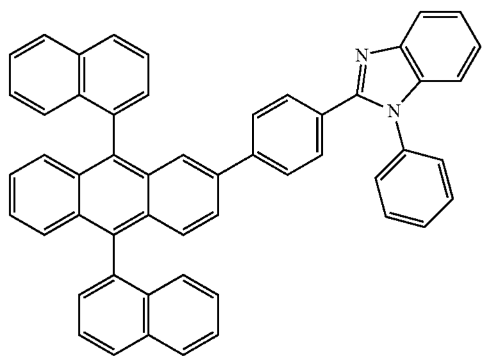
ET7
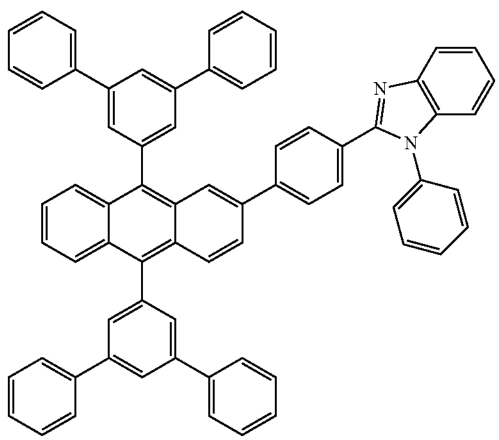
ET8
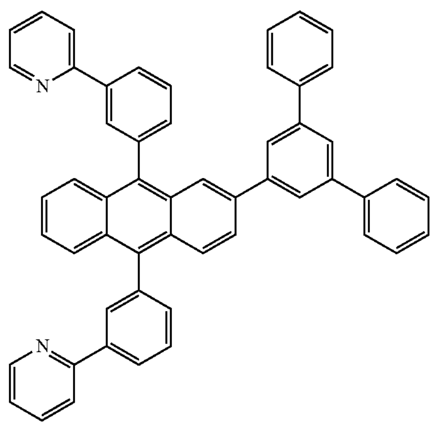

-continued
ET9
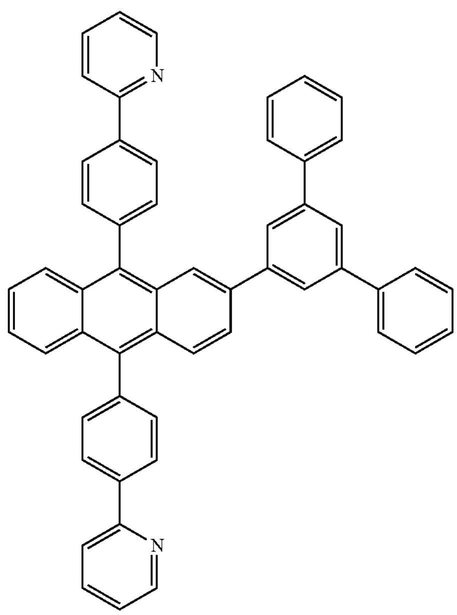
ET10
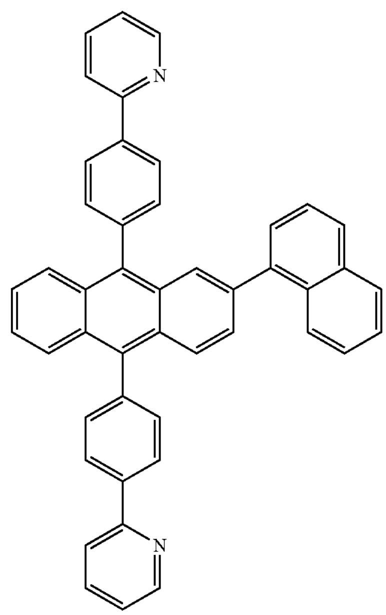
ET11
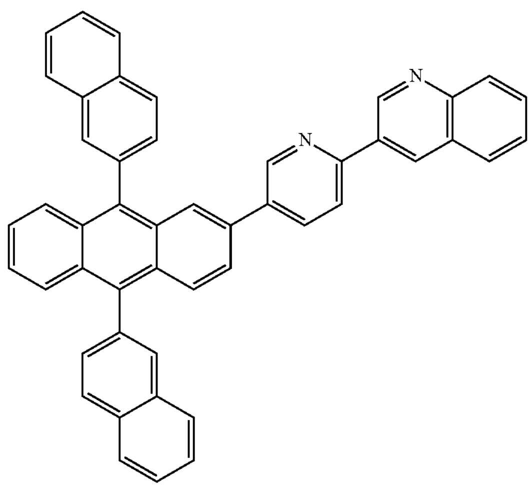
ET12
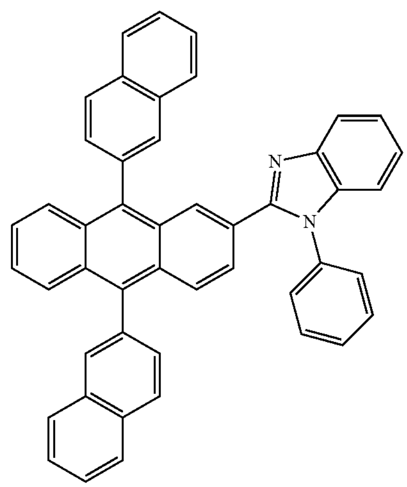
ET13
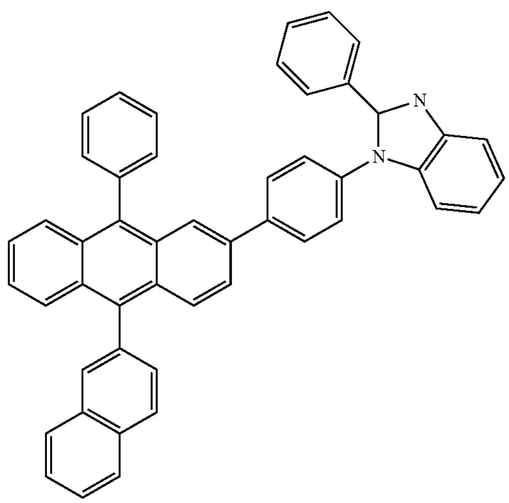
ET14
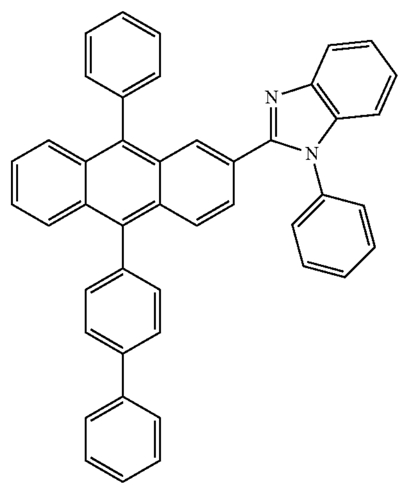

-continued
ET15
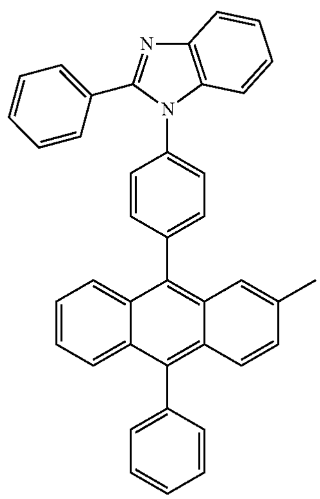
ET16
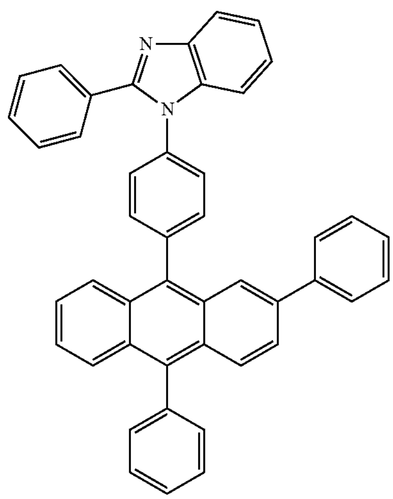
ET17
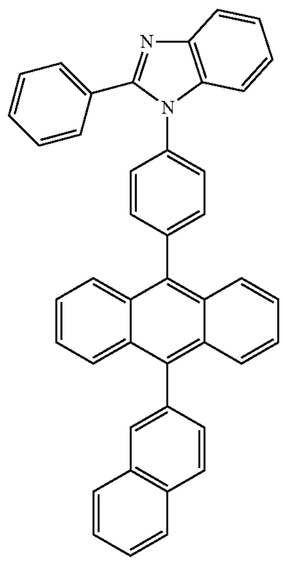
ET18
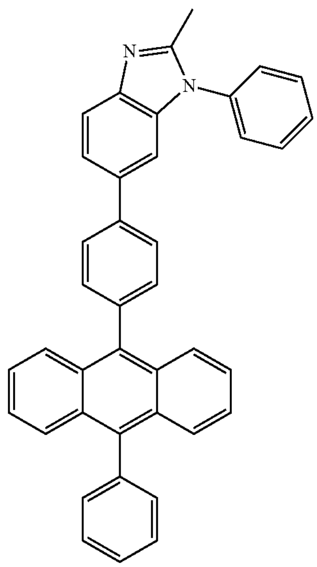
ET19
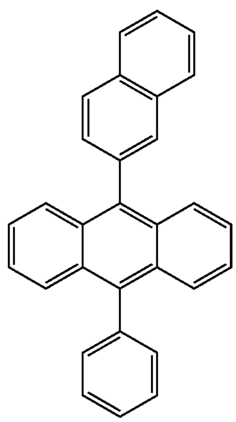
ET20
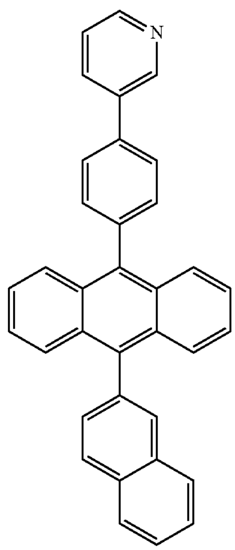

-continued
ET21
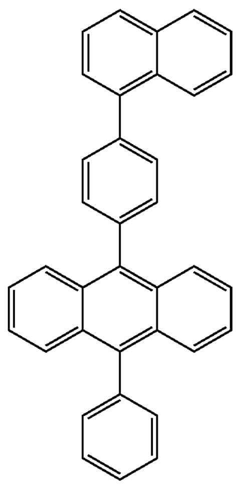
ET22
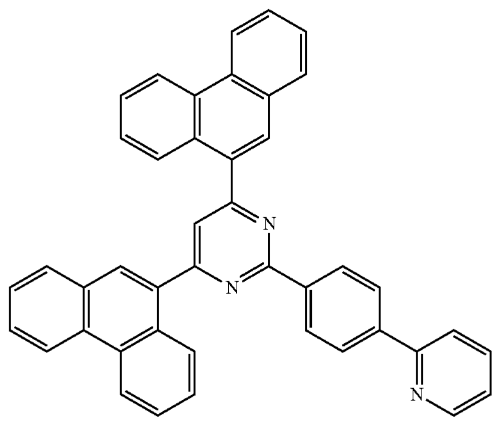
ET23
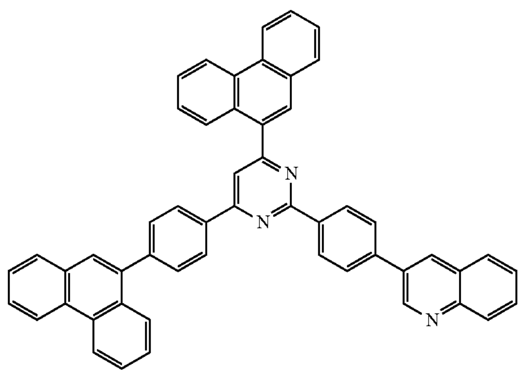
ET24
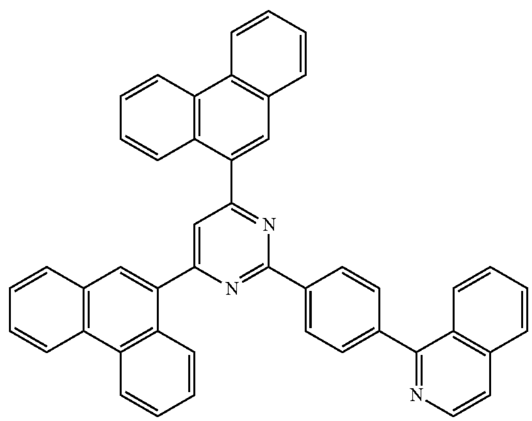
ET25
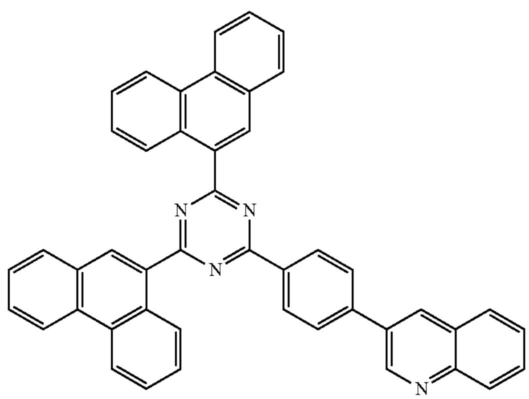
ET26
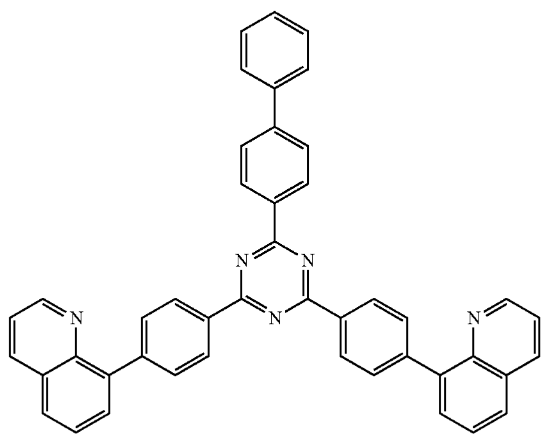

-continued
ET27
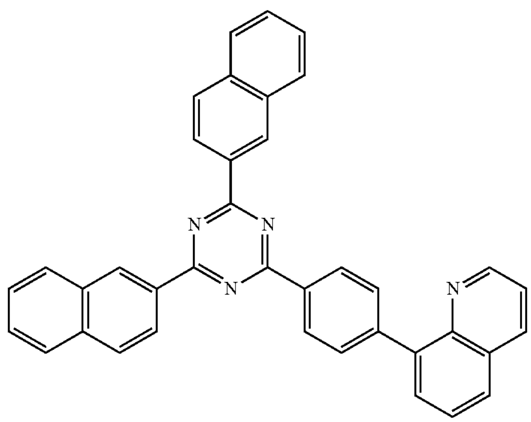
ET28
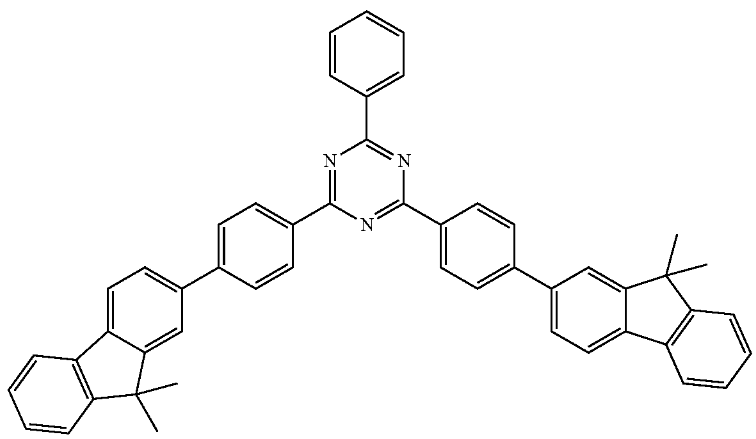
ET29
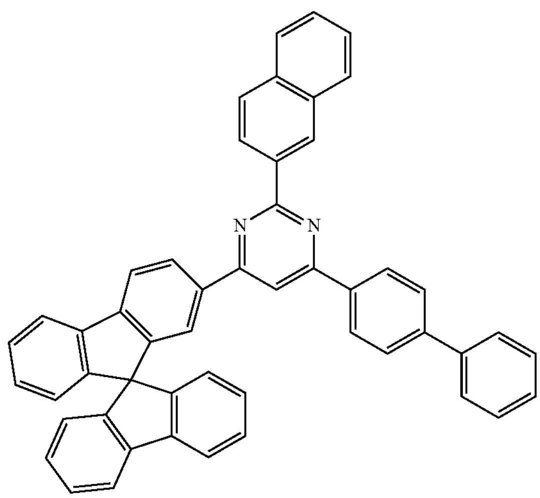
ET30
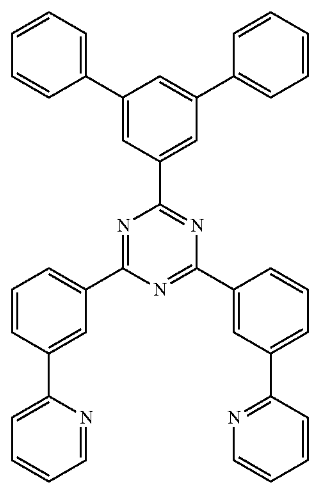

-continued
ET31
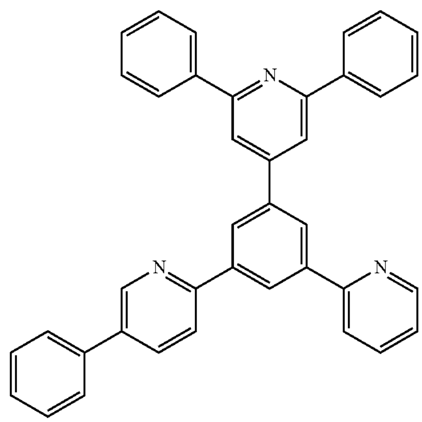
ET32
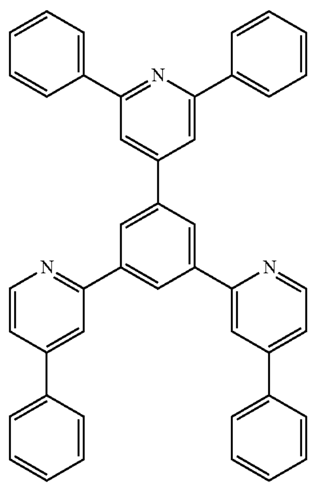
ET33
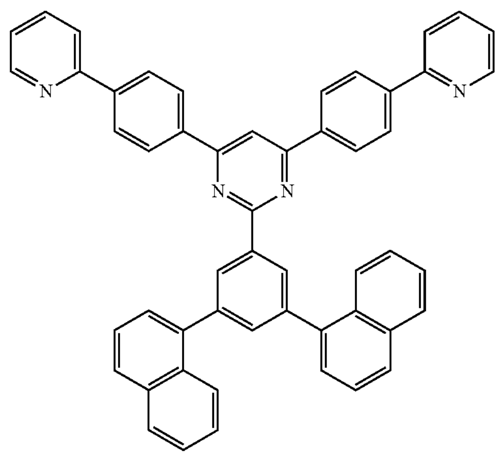
ET34
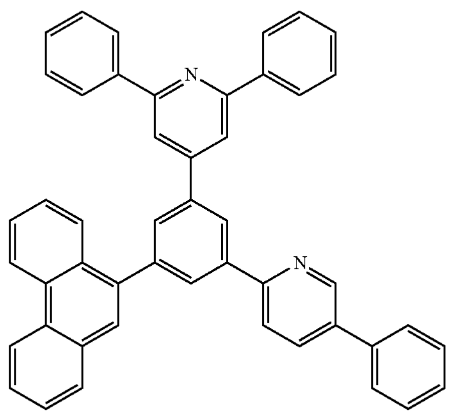
ET35
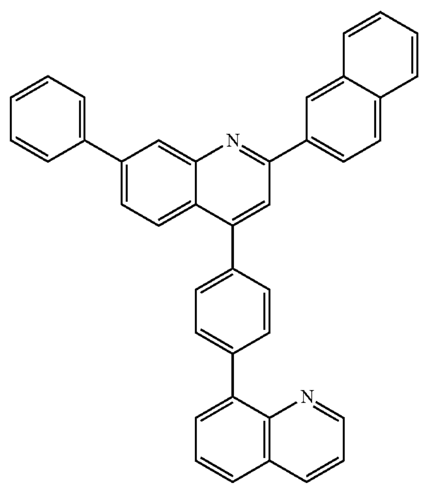
ET36
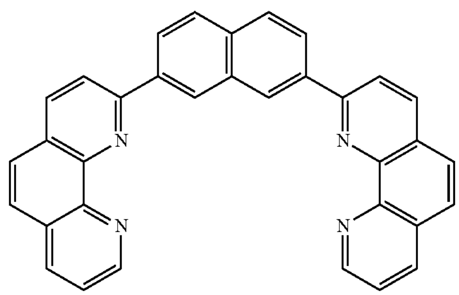

-continued
ET37
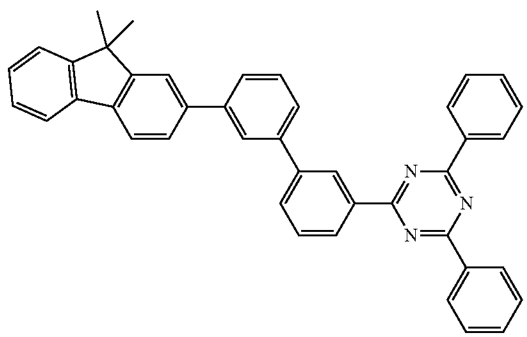
ET38
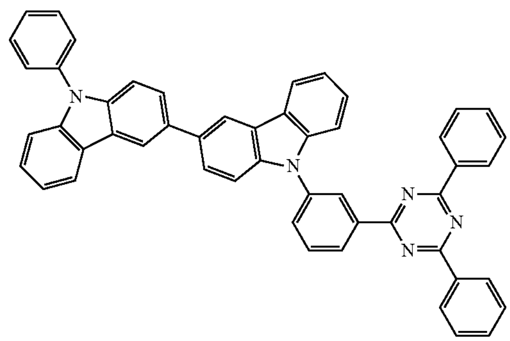
ET39
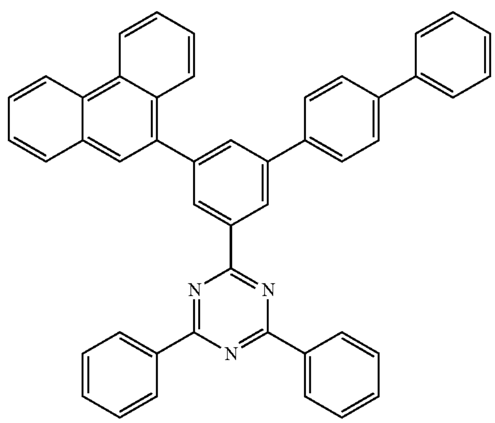
ET40
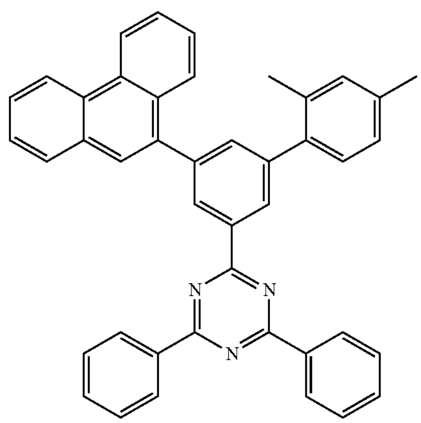
ET41
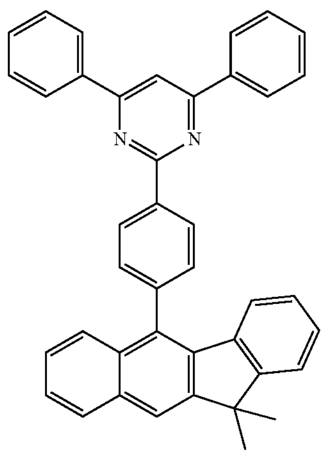
ET42
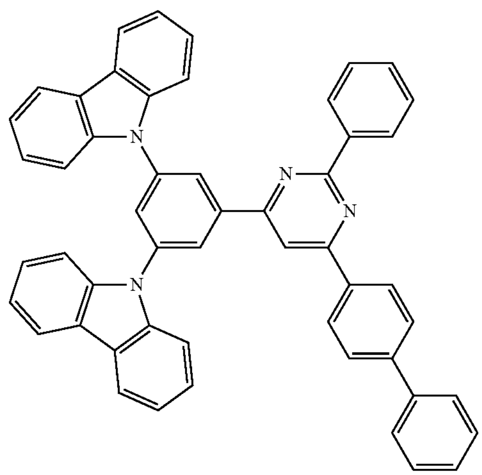

-continued

ET43

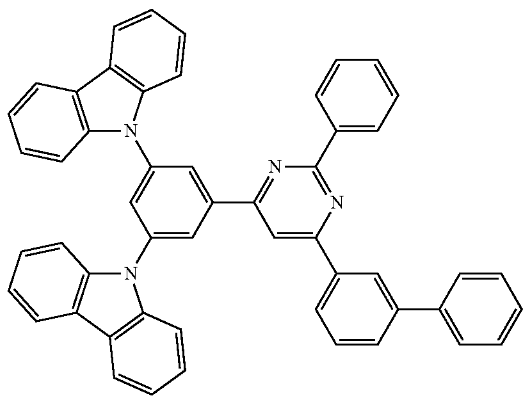

ET44

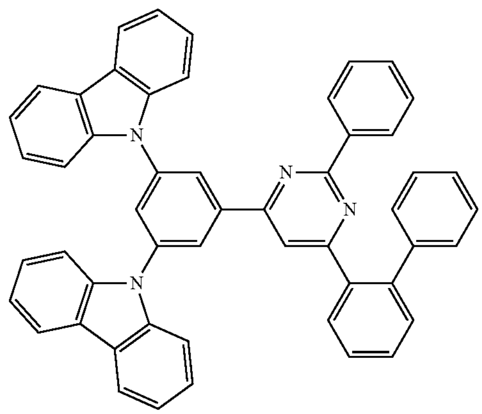

ET45

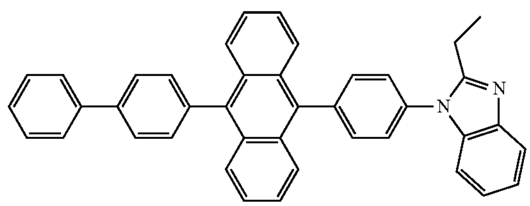

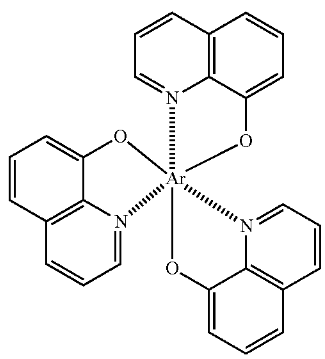

Alq3

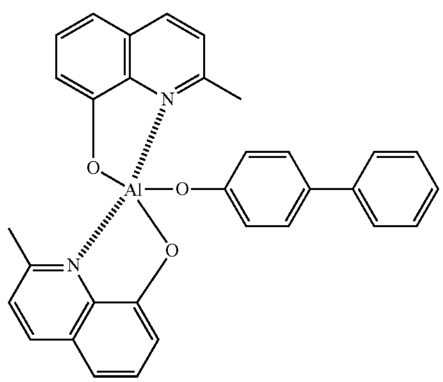

BAlq

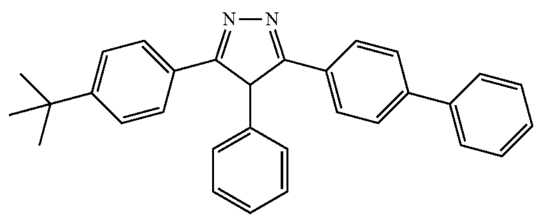

TAZ

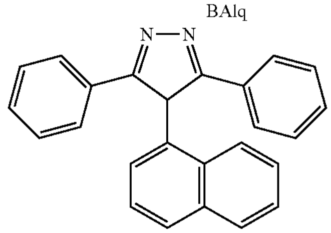

NTAZ

.

The thickness of the electron transport region 136 may be from about 100 Å to about 5,000 Å, for example, about 160 Å to about 4,000 Å. When the electron transport region 136 includes an electron transport layer, a buffer layer, a hole-blocking layer, an electron control layer, or any combination thereof, the thickness of the buffer layer, the hole-blocking layer, or the electron control layer may each independently be from about 20 Å to about 1000 Å, for example, about 30

Å to about 300 Å, and the thickness of the electron transport layer may be from about 100 Å to about 1000 Å, for example, about 150 Å to about 500 Å. When the thicknesses of the buffer layer, the hole-blocking layer, the electron control layer, and/or the electron transport layer are within these ranges, satisfactory electron transporting characteristics may be obtained without a substantial increase in driving voltage.

The electron transport region 136 (for example, the electron transport layer in the electron transport region) may further include, in addition to the materials described above, a metal-containing material.

The metal-containing material may include an alkali metal complex, alkaline earth metal complex, or any combination thereof. The metal ion of an alkali metal complex may be a Li ion, a Na ion, a K ion, a Rb ion, or a Cs ion, and the metal ion of alkaline earth metal complex may be a Be ion, a Mg ion, a Ca ion, a Sr ion, or a Ba ion. A ligand coordinated with the metal ion of the alkali metal complex or the alkaline earth-metal complex may include a hydroxyquinoline, a hydroxyisoquinoline, a hydroxybenzoquinoline, a hydroxyacridine, a hydroxyphenanthridine, a hydroxyphenyloxazole, a hydroxyphenylthiazole, a hydroxyphenyloxadiazole, a hydroxyphenylthiadiazole, a hydroxyphenylpyridine, a hydroxyphenylbenzimidazole, a hydroxyphenylbenzothiazole, a bipyridine, a phenanthroline, a cyclopentadiene, or any combination thereof.

For example, the metal-containing material may include a $L_1$ complex. The Li complex may include, for example, Compound ET-D1 (LiQ) or ET-D2:

ET-D1

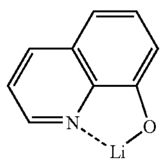

ET-D2

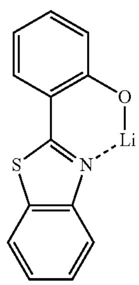

The electron transport region 136 may include an electron injection layer that facilitates the injection of electrons from the second electrode 150. The electron injection layer may be in direct contact with the second electrode 150.

The electron injection layer may have: i) a single-layered structure consisting of a single layer consisting of a single material, ii) a single-layered structure consisting of a single layer consisting of a plurality of different materials, or iii) a multi-layered structure including a plurality of layers including different materials.

The electron injection layer may include an alkali metal, alkaline earth metal, a rare earth metal, an alkali metal-containing compound, alkaline earth metal-containing compound, a rare earth metal-containing compound, an alkali metal complex, alkaline earth metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may be oxides, halides (for example, fluorides, chlorides, bromides, or iodides), or tellurides of the alkali metal, the alkaline earth metal, and the rare earth metal, or any combination thereof.

The alkali metal-containing compound may include alkali metal oxides, such as $Li_2O$, $Cs_2O$, or $K_2O$, alkali metal halides, such as LiF, NaF, CsF, KF, LiI, NaI, CsI, or KI, or any combination thereof. The alkaline earth metal-containing compound may include an alkaline earth metal compound, such as BaO, SrO, CaO, $Ba_xSr_{1-x}O$ (x is a real number satisfying the condition of $0<x<1$), $Ba_xCa_{1-x}O$ (x is a real number satisfying the condition of $0<x<1$), or the like. The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In one or more embodiments, the rare earth metal-containing compound may include lanthanide metal telluride. Examples of the lanthanide metal telluride are LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may include i) one of ions of the alkali metal, the alkaline earth metal, and the rare earth metal and ii), as a ligand bonded to the metal ion, for example, hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenyl benzimidazole, hydroxyphenylbenzothiazole, bipyridine, phenanthroline, cyclopentadiene, or any combination thereof.

The electron injection layer may consist of an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In one or more embodiments, the electron injection layer may further include an organic material (for example, a compound represented by Formula 601).

In one or more embodiments, the electron injection layer may consist of i) an alkali metal-containing compound (for example, an alkali metal halide), ii) a) an alkali metal-containing compound (for example, an alkali metal halide); and b) an alkali metal, an alkaline earth metal, a rare earth metal, or any combination thereof. In one or more embodiments, the electron injection layer may be a KI:Yb co-deposited layer, an RbI:Yb co-deposited layer, or the like.

When the electron injection layer further includes an organic material, alkali metal, alkaline earth metal, rare earth metal, an alkali metal-containing compound, an alkaline earth metal-containing compound, a rare earth metal-containing compound, alkali metal complex, alkaline earth-metal complex, rare earth metal complex, or any combination thereof may be homogeneously or non-homogeneously dispersed in a matrix including the organic material.

A thickness of the electron injection layer may be in a range of about 1 Å to about 100 Å, and, for example, about 3 Å to about 90 Å. When the thickness of the electron injection layer is within the range described above, the electron injection layer may have satisfactory electron injection characteristics without a substantial increase in driving voltage.

[Second Electrode 150]

The second electrode 150 may be located on the interlayer 130 having such a structure. The second electrode 150 may be a cathode, which is an electron injection electrode, and as the material for the second electrode 150, a metal, an alloy, an electrically conductive compound, or any combination thereof, each having a low work function, may be used.

In an embodiment, an amount of silver (Ag) in the second electrode 150 may be 95 wt % or more.

In an embodiment, the second electrode may further include magnesium (Mg). For example, the amount of the magnesium in the second electrode may be 5 wt % or less.

In an embodiment, the second electrode 150 may further include lithium (Li), silver (Ag), magnesium (Mg), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or a combination thereof.

In an embodiment, the second electrode 150 may further include magnesium (Mg), and the amount of the magnesium may be 5 wt % or less.

The second electrode 150 may be a transmissive electrode, a semi-transmissive electrode, or a reflective electrode.

The second electrode 150 may have a single-layered structure or a multi-layered structure including two or more layers.

[Capping Layer]

An electron transport capping layer may be located outside the second electrode 150.

In addition, a first capping layer may be located outside the first electrode 110, and/or a second capping layer may be additionally located outside the second electrode 150. In an embodiment, the light-emitting device 10 may have a structure in which a first capping layer, the first electrode 110, the interlayer 130, the second electrode 150, and the electron transport capping layer 170 are sequentially stacked, a structure in which the first electrode 110, the first capping layer, the interlayer 130, the second electrode 150, and the electron transport capping layer 170 are sequentially stacked, a structure in which the first electrode 110, the interlayer 130, the second electrode 150, the electron transport capping layer 170, and the second capping layer are sequentially stacked, a structure in which the first capping layer, the first electrode 110, the interlayer 130, the second electrode 150, the electron transport capping layer 170, and the second capping layer are sequentially stacked, or a structure in which the first electrode 110, the first capping layer, the interlayer 130, the second electrode 150, the electron transport capping layer 170, and the second capping layer are sequentially stacked.

The light generated by the emission layer 135 in the interlayer 130 of the light-emitting device 10 may be extracted to the outside through the second electrode 150, which is a semi-transmissive electrode or a transmissive electrode, and the electron transport capping layer 170.

In an embodiment, light generated in an emission layer of the interlayer 130 of the light-emitting device 10 may be extracted toward the outside through the first electrode 110, which is a semi-transmissive electrode or a transmissive electrode, and the first capping layer or light generated in an emission layer of the interlayer 130 of the light-emitting device 10 may be extracted toward the outside through the second electrode 150, which is a semi-transmissive electrode or a transmissive electrode, the electron transport capping layer 170 and the second capping layer.

The electron transport capping layer, the first capping layer and the second capping layer may increase external luminescence efficiency according to the principle of constructive interference. Accordingly, the light extraction efficiency of the light-emitting device 10 is increased, so that the luminescence efficiency of the light-emitting device 10 may be improved.

Each of the electron transport capping layer 170, the first capping layer, and the second capping layer may include a material having a refractive index of 1.6 or more (at 589 nm).

The electron transport capping layer 170 may be understood based on the description provided in the present specification. In addition, in an embodiment, the electron transport capping layer 170 may be understand based on the description provided in connection with the first capping layer and the second capping layer.

The first capping layer and the second capping layer may each independently be an organic capping layer including an organic material, an inorganic capping layer including an inorganic material, or an organic-inorganic composite capping layer including an organic material and an inorganic material.

At least one selected from the first capping layer and the second capping layer may each independently include carbocyclic compounds, heterocyclic compounds, amine group-containing compounds, porphyrin derivatives, phthalocyanine derivatives, naphthalocyanine derivatives, alkali metal complexes, alkaline earth metal complexes, or any combination thereof. The carbocyclic compound, the heterocyclic compound, and the amine group-containing compound may be optionally substituted with a substituent containing O, N, S, Se, Si, F, Cl, Br, I, or any combination thereof.

In one or more embodiments, at least one of the first capping layer and the second capping layer may each independently include an amine group-containing compound.

In one or more embodiments, at least one of the first capping layer and the second capping layer may each independently include a compound represented by Formula 201, a compound represented by Formula 202, or any combination thereof.

In one or more embodiments, at least one of the first capping layer and the second capping layer may each independently include one of Compounds HT28 to HT33, one of Compounds CP1 to CP6, β-NPB, or any combination thereof.

CP1

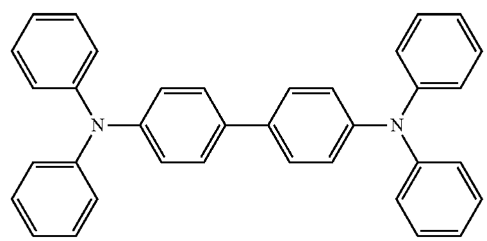

-continued

CP2

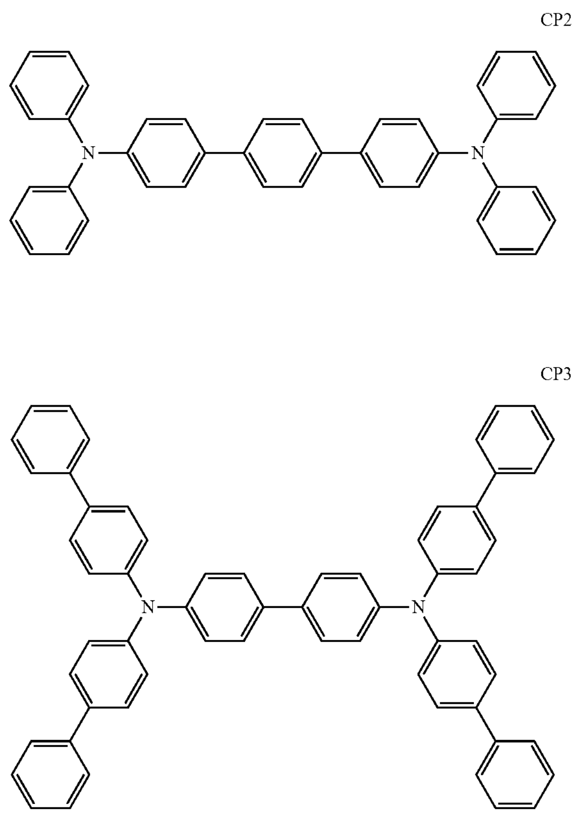

CP3

CP4

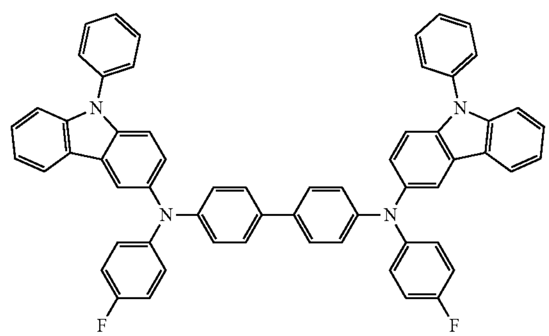

CP5

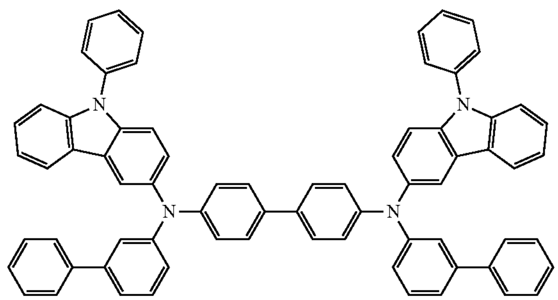

-continued

CP6

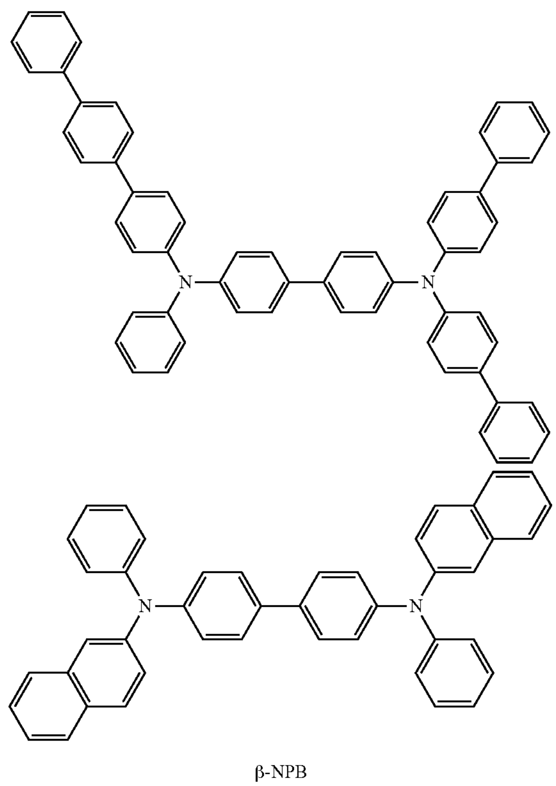

β-NPB

[Film]

The first compound represented by Formula 1 may be included in various films. Accordingly, according to another aspect, a film including the first compound represented by Formula 1 and/or the second compound represented by Formula 2 may be provided. The film may be, for example, an optical member (or, light control means) (for example, a color filter, a color conversion member, a capping layer, a light extraction efficiency enhancement layer, a selective light absorbing layer, a polarizing layer, or a quantum dot-containing layer), a light-blocking member (for example, a light reflective layer or a light absorbing layer), a protective member (for example, an insulating layer or a dielectric layer).

[Electronic Apparatus]

The light-emitting device may be included in various electronic apparatuses. In one or more embodiments, the electronic apparatus including the light-emitting device may be a light-emitting apparatus, an authentication apparatus, or the like.

The electronic apparatus (for example, light-emitting apparatus) may further include, in addition to the light-emitting device, i) a color filter, ii) a color conversion layer, or iii) a color filter and a color conversion layer. The color filter and/or the color conversion layer may be located in at least one traveling direction of light emitted from the light-emitting device. In one or more embodiments, the light emitted from the light-emitting device may be blue light or white light. The light-emitting device may be the same as described above. In one or more embodiments, the color conversion layer may include quantum dots. The quantum dot may be, for example, a quantum dot as described herein.

The electronic apparatus may include a first substrate. The first substrate may include a plurality of subpixel areas, the color filter may include a plurality of color filter areas respectively corresponding to the subpixel areas, and the color conversion layer may include a plurality of color conversion areas respectively corresponding to the subpixel areas.

A pixel-defining film may be located among the subpixel areas to define each of the subpixel areas.

The color filter may further include a plurality of color filter areas and light-shielding patterns located among the color filter areas, and the color conversion layer may include a plurality of color conversion areas and light-shielding patterns located among the color conversion areas.

The color filter areas (or the color conversion areas) may include a first area emitting first color light, a second area emitting second color light, and/or a third area emitting third color light, and the first color light, the second color light, and/or the third color light may have different maximum emission wavelengths from one another. In one or more embodiments, the first color light may be red light, the second color light may be green light, and the third color light may be blue light. In one or more embodiments, the color filter areas (or the color conversion areas) may include quantum dots. In detail, the first area may include a red quantum dot, the second area may include a green quantum dot, and the third area may not include a quantum dot. The quantum dot is the same as described in the present specification. The first area, the second area, and/or the third area may each include a scatter.

In one or more embodiments, the light-emitting device may emit first light, the first area may absorb the first light to emit first first-color light, the second area may absorb the first light to emit second first-color light, and the third area may absorb the first light to emit third first-color light. In this regard, the first first-color light, the second first-color light, and the third first-color light may have different maximum emission wavelengths. In detail, the first light may be blue light, the first first-color light may be red light, the second first-color light may be green light, and the third first-color light may be blue light.

The electronic apparatus may further include a thin-film transistor in addition to the light-emitting device as described above. The thin-film transistor may include a source electrode, a drain electrode, and an activation layer, wherein any one of the source electrode and the drain electrode may be electrically connected to any one of the first electrode and the second electrode of the light-emitting device.

The thin-film transistor may further include a gate electrode, a gate insulating film, etc.

The activation layer may include crystalline silicon, amorphous silicon, organic semiconductor, oxide semiconductor, or the like.

The electronic apparatus may further include a sealing portion for sealing the light-emitting device. The sealing portion and/or the color conversion layer may be placed between the color filter and the light-emitting device. The sealing portion allows light from the light-emitting device to be extracted to the outside, while simultaneously preventing ambient air and moisture from penetrating into the light-emitting device. The sealing portion may be a sealing substrate including a transparent glass substrate or a plastic substrate. The sealing portion may be a thin-film encapsulation layer including at least one layer of an organic layer and/or an inorganic layer. When the sealing portion is a thin film encapsulation layer, the electronic apparatus may be flexible.

Various functional layers may be additionally located on the sealing portion, in addition to the color filter and/or the color conversion layer, according to the use of the electronic apparatus. The functional layers may include a touch screen layer, a polarizing layer, and the like. The touch screen layer may be a pressure-sensitive touch screen layer, a capacitive touch screen layer, or an infrared touch screen layer. The authentication apparatus may be, for example, a biometric authentication apparatus that authenticates an individual by using biometric information of a living body (for example, fingertips, pupils, etc.).

The authentication apparatus may further include, in addition to the light-emitting device, a biometric information collector.

The electronic apparatus may be applied to various displays, light sources, lighting, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, or endoscope displays), fish finders, various measuring instruments, meters (for example, meters for a vehicle, an aircraft, and a vessel), projectors, and the like.

Figure 3:
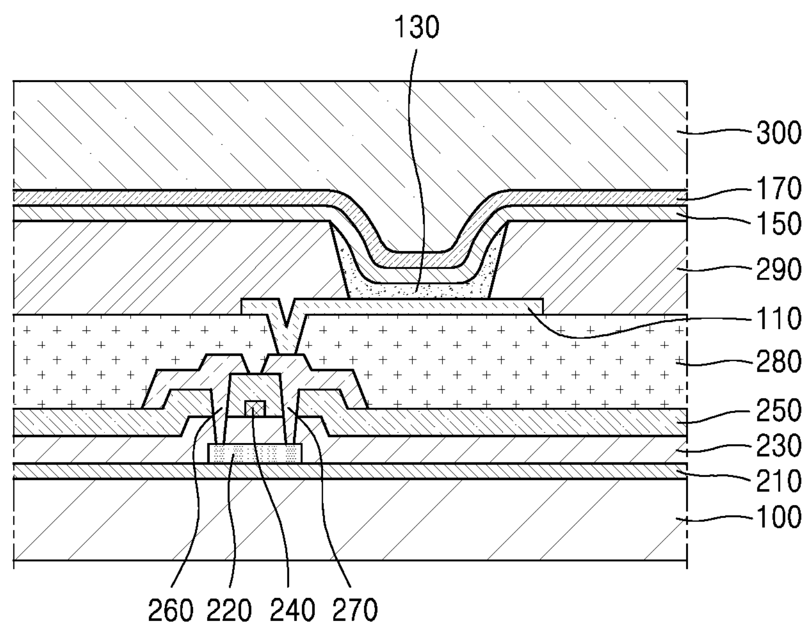
FIG. 3 shows a diagram schematically showing the structure of an electronic apparatus according to an embodiment.
Figure 4:
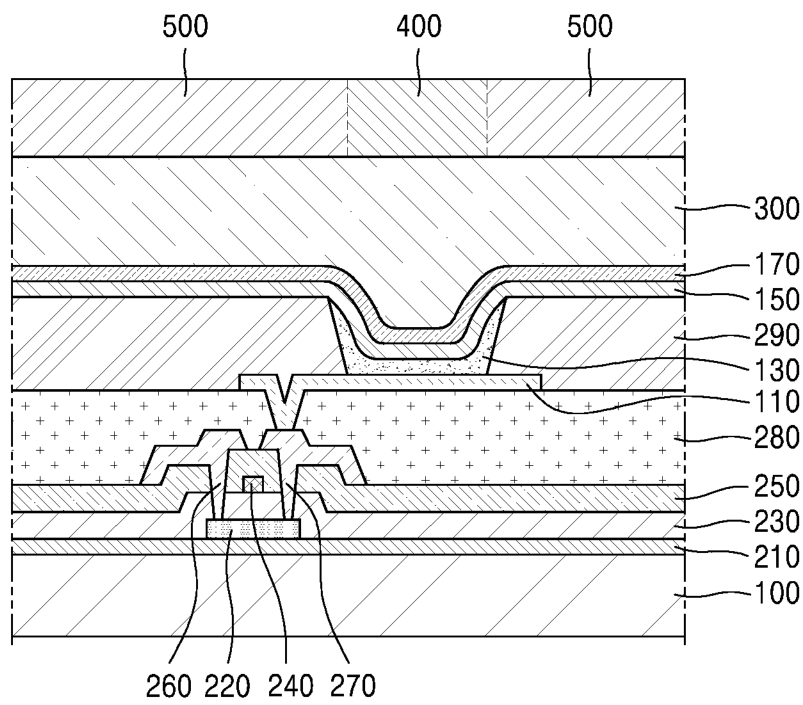
FIG. 4 shows a diagram schematically showing the structure of an electronic apparatus according to an embodiment.

[Description of FIGS. 3 and 4]

FIG. 3 is a cross-sectional view showing a light-emitting apparatus according to an embodiment of the present disclosure.

The light-emitting apparatus of FIG. 3 includes a substrate 100, a thin-film transistor (TFT), a light-emitting device, and an encapsulation portion 300 that seals the light-emitting device.

The substrate 100 may be a flexible substrate, a glass substrate, or a metal substrate. A buffer layer 210 may be formed on the substrate 100. The buffer layer 210 may prevent penetration of impurities through the substrate 100 and may provide a flat surface on the substrate 100.

A TFT may be located on the buffer layer 210. The TFT may include an activation layer 220, a gate electrode 240, a source electrode 260, and a drain electrode 270.

The activation layer 220 may include an inorganic semiconductor such as silicon or polysilicon, an organic semiconductor, or an oxide semiconductor, and may include a source region, a drain region and a channel region.

A gate insulating film 230 for insulating the activation layer 220 from the gate electrode 240 may be located on the activation layer 220, and the gate electrode 240 may be located on the gate insulating film 230.

An interlayer insulating film 250 is located on the gate electrode 240. The interlayer insulating film 250 may be placed between the gate electrode 240 and the source electrode 260 to insulate the gate electrode 240 from the source electrode 260 and between the gate electrode 240 and the drain electrode 270 to insulate the gate electrode 240 from the drain electrode 270.

The source electrode 260 and the drain electrode 270 may be located on the interlayer insulating film 250. The interlayer insulating film 250 and the gate insulating film 230 may be formed to expose the source region and the drain region of the activation layer 220, and the source electrode 260 and the drain electrode 270 may be in contact with the exposed portions of the source region and the drain region of the activation layer 220.

The TFT is electrically connected to a light-emitting device to drive the light-emitting device, and is covered by a passivation layer 280. The passivation layer 280 may include an inorganic insulating film, an organic insulating film, or any combination thereof. A light-emitting device is provided on the passivation layer 280. The light-emitting device may include a first electrode 110, an interlayer 130, and a second electrode 150.

The first electrode 110 may be formed on the passivation layer 280. The passivation layer 280 does not completely cover the drain electrode 270 and exposes a portion of the drain electrode 270, and the first electrode 110 is connected to the exposed portion of the drain electrode 270.

A pixel defining layer 290 containing an insulating material may be located on the first electrode 110. The pixel defining layer 290 exposes a region of the first electrode 110, and an interlayer 130 may be formed in the exposed region of the first electrode 110. The pixel defining layer 290 may be a polyimide or polyacrylic organic film. Although not shown in FIG. 3, at least some layers of the interlayer 130 may extend beyond the upper portion of the pixel defining layer 290 and may thus be located in the form of a common layer.

The second electrode 150 may be located on the interlayer 130, and the electron transport capping layer 170 may be additionally formed on the second electrode 150. The electron transport capping layer 170 may be formed to cover the second electrode 150.

The encapsulation portion 300 may be located on the electron transport capping layer 170. The encapsulation portion 300 may be located on a light-emitting device to protect the light-emitting device from moisture or oxygen. The encapsulation portion 300 may include: an inorganic film including silicon nitride ($SiN_x$), silicon oxide ($SiO_x$), indium tin oxide, indium zinc oxide, or any combination thereof, an organic film including polyethylene terephthalate, polyethylene naphthalate, polycarbonate, polyimide, polyethylene sulfonate, polyoxymethylene, polyarylate, hexamethyldisiloxane, an acrylic resin (for example, polymethyl methacrylate, polyacrylic acid, or the like), an epoxy-based resin (for example, aliphatic glycidyl ether (AGE), or the like), or any combination thereof, or any combination of the inorganic film and the organic film.

FIG. 4 is a cross-sectional view showing a light-emitting apparatus according to an embodiment of the present disclosure.

The light-emitting apparatus of FIG. 4 is the same as the light-emitting apparatus of FIG. 3, except that a light-shielding pattern 500 and a functional region 400 are additionally located on the encapsulation portion 300. The functional region 400 may be a combination of i) a color filter area, ii) a color conversion area, or iii) a combination of the color filter area and the color conversion area. In one or more embodiments, the light-emitting device included in the light-emitting apparatus of FIG. 4 may be a tandem light-emitting device.

[Manufacture Method]

Respective layers included in the hole transport region, the emission layer, and respective layers included in the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec, depending on a material to be included in a layer to be formed and the structure of a layer to be formed.

[Definition of Terms]

The term "$C_3$-$C_{60}$ carbocyclic group" as used herein refers to a cyclic group consisting of carbon only as a ring-forming atom and having three to sixty carbon atoms, and the term "$C_1$-$C_{60}$ heterocyclic group" as used herein refers to a cyclic group that has one to sixty carbon atoms and further has, in addition to carbon, a heteroatom as a ring-forming atom. The $C_3$-$C_{60}$ carbocyclic group and the $C_1$-$C_{60}$ heterocyclic group may each be a monocyclic group consisting of one ring or a polycyclic group in which two or more rings are condensed with each other. For example, the $C_1$-$C_{60}$ heterocyclic group has 3 to 61 ring-forming atoms.

The "cyclic group" as used herein may include the $C_3$-$C_{60}$ carbocyclic group, and the $C_1$-$C_{60}$ heterocyclic group.

The term "π electron-rich $C_3$-$C_{60}$ cyclic group" as used herein refers to a cyclic group that has three to sixty carbon atoms and does not include *—N═*' as a ring-forming moiety, and the term "n electron-deficient nitrogen-containing $C_1$-$C_{60}$ cyclic group" as used herein refers to a heterocyclic group that has one to sixty carbon atoms and includes *—N═*' as a ring-forming moiety.

For example, the $C_3$-$C_{60}$ carbocyclic group may be i) group T1 or ii) a condensed cyclic group in which two or more groups T1 are condensed with each other (for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, or an indenoanthracene group), the $C_1$-$C_{60}$ heterocyclic group may be i) group T2, ii) a condensed cyclic group in which two or more groups T2 are condensed with each other, or iii) a condensed cyclic group in which at least one group T2 and at least one group T1 are condensed with each other (for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), the π electron-rich $C_3$-$C_{60}$ cyclic group may be i) group T1, ii) a condensed cyclic group in which two or more groups T1 are condensed with each other, iii) group T3, iv) a condensed cyclic group in which two or more groups T3 are condensed with each other, or v) a condensed cyclic group in which at least one group T3 and at least one group T1 are condensed with each other (for example, the $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, etc.), the π electron-deficient nitrogen-containing $C_1$-$C_{60}$ cyclic group may be i) group T4, ii) a condensed cyclic group in which two or more groups T4 are condensed with each other, iii) a condensed cyclic group in which at least one group T4 and at least one group T1 are condensed with each other, iv) a condensed cyclic group in which at least one group T4 and at least one group T3 are condensed with each other, or v) a condensed cyclic group in which at least one group T4, at least one group T1, and at least one group T3 are condensed with one another (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), group T1 may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or a bicyclo[2.2.1]heptane) group, a norbornene group, a bicyclo[1.1.1]pentane group, a bicyclo[2.1.1]hexane group, a bicyclo[2.2.2]octane group, or a benzene group, group T2 may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group, group T3 may be a furan group, a thiophene group, a 1H-pyrrole group, a silole group, or a borole group, and group T4 may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "the cyclic group, the $C_3$-$C_{60}$ carbocyclic group, the $C_1$-$C_{60}$ heterocyclic group, the π electron-rich $C_3$-$C_{60}$ cyclic group, or the π electron-deficient nitrogen-containing $C_1$-$C_{60}$ cyclic group" as used herein refer to a group condensed to any cyclic group, a monovalent group or a polyvalent group (for example, a divalent group, a trivalent group, a tetravalent group, etc.), depending on the structure of a formula in connection with which the terms are used. In an embodiment, "a benzene group" may be a benzo group, a phenyl group, a phenylene group, or the like, which may be easily understand by one of ordinary skill in the art according to the structure of a formula including the "benzene group."

Examples of the monovalent $C_3$-$C_{60}$ carbocyclic group and the monovalent $C_1$-$C_{60}$ heterocyclic group are a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and examples of the divalent $C_3$-$C_{60}$ carbocyclic group and the divalent $C_1$-$C_{60}$ heterocyclic group are a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a divalent non-aromatic condensed heteropolycyclic group.

The term "$C_1$-$C_{60}$ alkyl group" as used herein refers to a linear or branched aliphatic hydrocarbon monovalent group that has one to sixty carbon atoms, and examples thereof are a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a monovalent hydrocarbon group having at least one carbon-carbon double bond in the middle or at the terminus of the $C_2$-$C_{60}$ alkyl group, and examples thereof are an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a monovalent hydrocarbon group having at least one carbon-carbon triple bond in the middle or at the terminus of the $C_2$-$C_{60}$ alkyl group, and examples thereof include an ethynyl group and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon cyclic group having 3 to 10 carbon atoms, and examples thereof are a cyclopropyl group, a cyclobutyl group, a cyclopentyl group, a cyclohexyl group, a cycloheptyl group, a cyclooctyl group, an adamantanyl group, a norbornanyl group (or bicyclo [2.2.1]heptyl group), a bicyclo[1.1.1]pentyl group, a bicyclo [2.1.1]hexyl group, and a bicyclo[2.2.2]octyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent cyclic group that further includes, in addition to a carbon atom, at least one heteroatom as a ring-forming atom and has 1 to 10 carbon atoms, and examples thereof are a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term $C_3$-$C_{10}$ cycloalkenyl group used herein refers to a monovalent cyclic group that has three to ten carbon atoms and at least one carbon-carbon double bond in the ring thereof and no aromaticity, and examples thereof are a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent cyclic group that has, in addition to a carbon atom, at least one heteroatom as a ring-forming atom, 1 to 10 carbon atoms, and at least one carbon-carbon double bond in the cyclic structure thereof. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having six to sixty carbon atoms, and the term "$C_6$-$C_{60}$ arylene group" as used herein refers to a divalent group having a carbocyclic aromatic system having six to sixty carbon atoms. Examples of the $C_6$-$C_{60}$ aryl group are a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, and an ovalenyl group. When the $C_6$-$C_{60}$ aryl group and the $C_6$-$C_{60}$ arylene group each include two or more rings, the rings may be condensed with each other.

The term "$C_1$-$C_{60}$ heteroaryl group" as used herein refers to a monovalent group having a heterocyclic aromatic system that has, in addition to a carbon atom, at least one heteroatom as a ring-forming atom, and 1 to 60 carbon atoms. The term "$C_1$-$C_{60}$ heteroarylene group" as used herein refers to a divalent group having a heterocyclic aromatic system that has, in addition to a carbon atom, at least one heteroatom as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. When the $C_1$-$C_{60}$ heteroaryl group and the $C_1$-$C_{60}$ heteroarylene group each include two or more rings, the rings may be condensed with each other.

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group are an indenyl group, a fluorenyl group, a spiro-bifluorenyl group, a benzofluorenyl group, an indenophenanthrenyl group, and an indeno anthracenyl group. The term "divalent non-aromatic condensed polycyclic group" as used herein refers to a divalent group having the same structure as a monovalent non-aromatic condensed polycyclic group.

The term "monovalent non-aromatic condensed heteropolycyclic group" as used herein refers to a monovalent group (for example, having 1 to 60 carbon atoms) having two or more rings condensed to each other, at least one heteroatom other than carbon atoms, as a ring-forming atom, and non-aromaticity in its entire molecular structure. Examples of the monovalent non-aromatic condensed heteropolycyclic group are a pyrrolyl group, a thiophenyl group, a furanyl group, an indolyl group, a benzoindolyl group, a naphtho indolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indenocarbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, and a benzothienodibenzothiophenyl group. The term "divalent non-aromatic heterocondensed polycyclic group" as used herein refers to a divalent group having the same structure as a monovalent non-aromatic heterocondensed polycyclic group.

The term "$C_6$-$C_{60}$ aryloxy group" as used herein indicates —$OA_{102}$ (wherein $A_{102}$ is the $C_6$-$C_{60}$ aryl group), and the term "$C_6$-$C_{60}$ arylthio group" as used herein indicates —$SA_{103}$ (wherein $A_{103}$ is the $C_6$-$C_{60}$ aryl group).

The term "$C_7$-$C_{60}$ aryl alkyl group" used herein refers to -$A_{104}A_{105}$ (where $A_{104}$ may be a $C_1$-$C_{54}$ alkylene group, and $A_{105}$ may be a $C_6$-$C_{59}$ aryl group), and the term $C_2$-$C_{60}$ heteroaryl alkyl group" used herein refers to -$A_{106}A_{107}$ (where $A_{106}$ may be a $C_1$-$C_{59}$ alkylene group, and $A_{107}$ may be a $C_1$-$C_{59}$ heteroaryl group).

The term "$R_{10a}$" as used herein refers to:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof, or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$.

$Q_1$ to $Q_3$, $Q_{11}$ to $Q_{13}$, $Q_{21}$ to $Q_{23}$, and $Q_{31}$ to $Q_{33}$ used herein may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof, a $C_7$-$C_{60}$ aryl alkyl group; or a $C_2$-$C_{60}$ heteroaryl alkyl group.

The term "hetero atom" as used herein refers to any atom other than a carbon atom. Examples of the heteroatom are O, S, N, P, Si, B, Ge, Se, and any combination thereof.

The term "the third-row transition metal" used herein includes hafnium (Hf), tantalum (Ta), tungsten (W), rhenium (Re), osmium (Os), iridium (Ir), platinum (Pt), gold (Au), etc.

The term "Ph" as used herein refers to a phenyl group, the term "Me" as used herein refers to a methyl group, the term "Et" as used herein refers to an ethyl group, the term "tert-Bu" or "$Bu^t$" as used herein refers to a tert-butyl group, and the term "OMe" as used herein refers to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The term "terphenyl group" as used herein refers to "a phenyl group substituted with a biphenyl group". In other words, the "terphenyl group" is a substituted phenyl group having, as a substituent, a $C_6$-$C_{60}$ aryl group substituted with a $C_6$-$C_{60}$ aryl group.

* and *' as used herein, unless defined otherwise, each refer to a binding site to a neighboring atom in a corresponding formula or moiety.

Hereinafter, a compound according to embodiments and a light-emitting device according to embodiments will be described in detail with reference to Examples. The wording "B was used instead of A" used in describing Examples refers to that an identical molar equivalent of B was used in place of A.

EXAMPLES

Example 1

An ITO glass substrate (50×50×0.5 mm, 15Ω/□), which is an organic light-emitting device (OLED) glass (manufactured by Samsung-Corning) substrate, was subjected to ultrasonic cleaning sequentially using distilled water and isopropanol, followed by UV ozone cleaning for 30 minutes.

The glass substrate with a transparent electrode line attached thereon after cleaning was mounted on a substrate holder of a vacuum deposition apparatus, and Compound HT3 was deposited on the ITO electrode (anode) to form a hole injection layer having a thickness of 120 nm. HT22 was deposited on the hole injection layer to form a hole transport layer having a thickness of 10 nm.

H8 (host) and DF8 (dopant) were co-deposited at a weight ratio of 98:2 on the hole transport layer to form an emission layer having a thickness of 20 nm.

Compound 2-1 and Yb (metal dopant) were co-deposited at a weight ratio of 97:3 on the emission layer to form an electron transport layer having a thickness of 30 nm.

Ag:Mg (weight ratio of 97:3) was deposited on the electron transport layer to form a cathode having a thickness of 10 nm, and Compound 1-53 was deposited on the cathode to form an electron transport capping layer having a thickness of 70 nm, thereby completing the manufacture of a light-emitting device. The equipment used for the deposition was a Suicel plus 200 evaporator from Sunic Systems Inc.

HT3

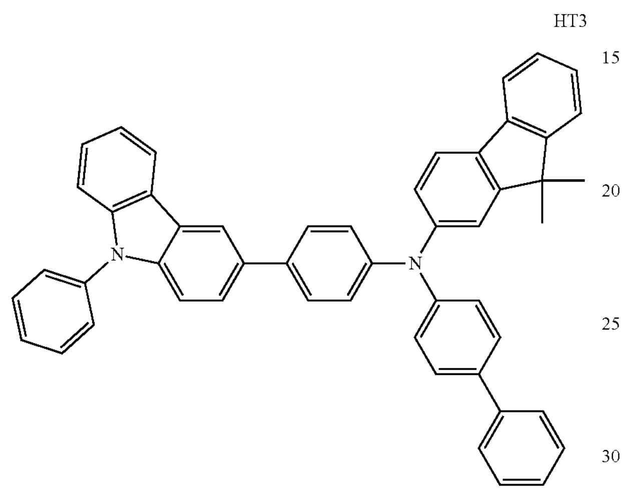

HT22

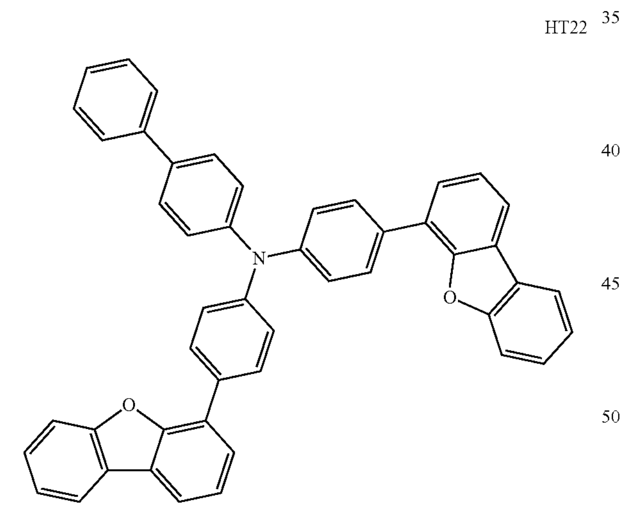

H8

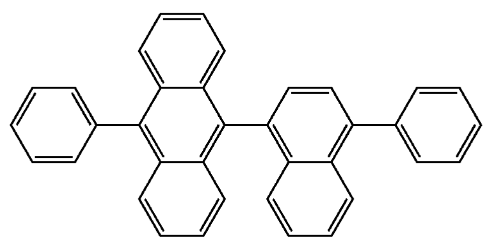

-continued

DF8

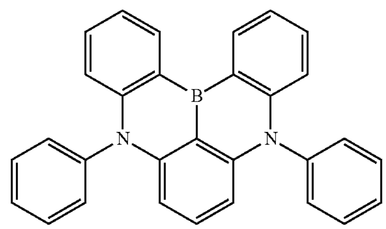

2-1

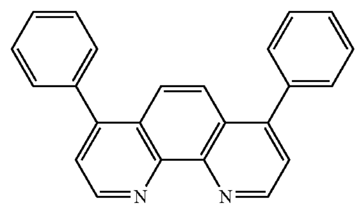

2-7

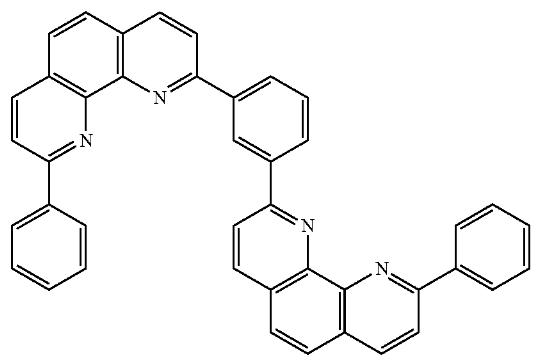

1-53

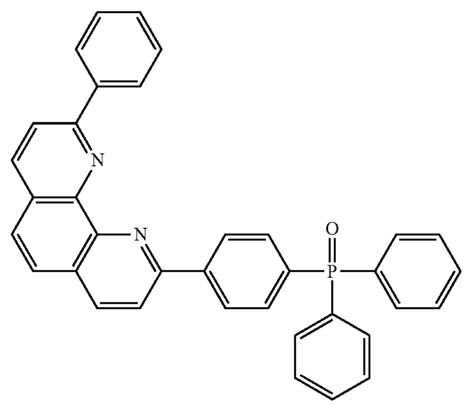

1-12

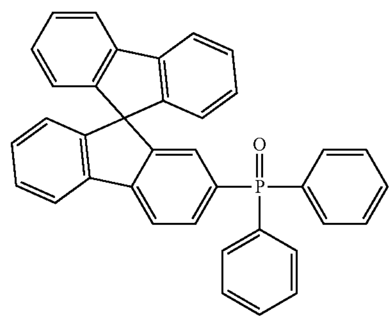

-continued 1-66

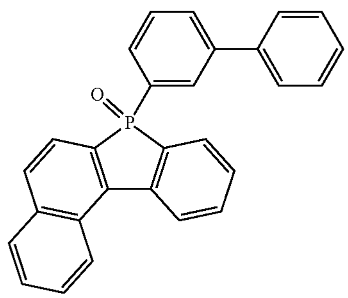

1-99

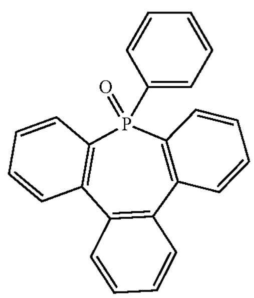

A

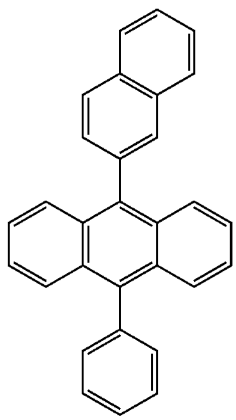

B

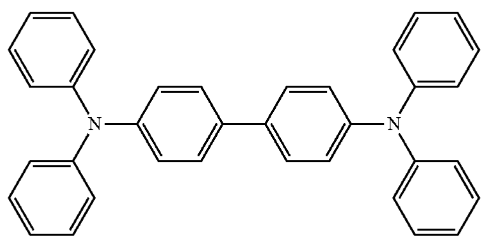

C

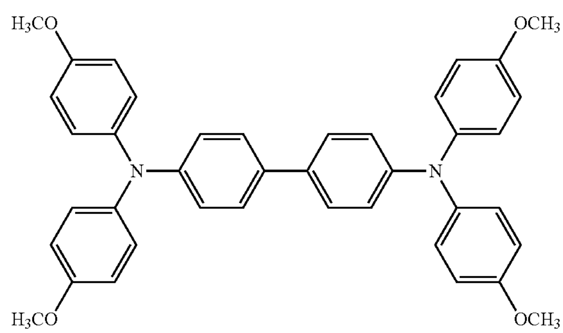

-continued

D

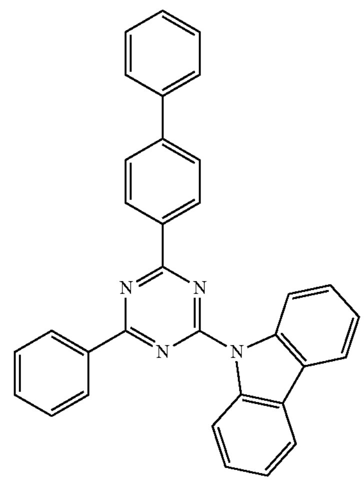

E

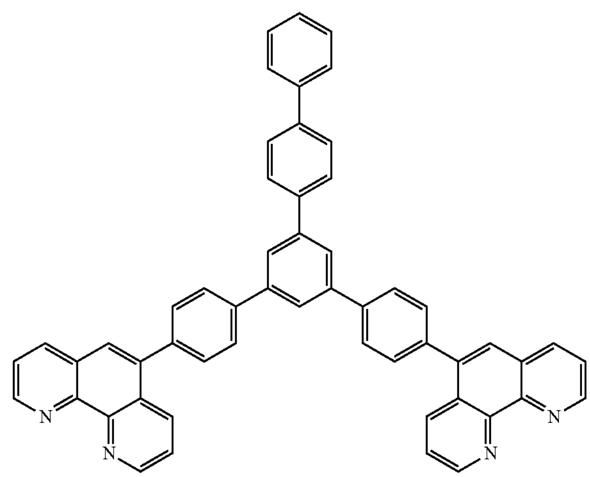

Examples 2 to 10 and Comparative Example 1 to 5

Light-emitting devices were manufactured in the same manner as in Example 1, except that the materials for light-emitting devices shown in Table 1 were used.

Evaluation Example 1

The driving voltage and current efficiency of each of the light-emitting devices manufactured according to Examples 1 to 10 and Comparative Examples 1 to 5 were measured using a Keithley SMU 236 and luminance meter PR650, and the results are shown in Table 1 as relative values.

TABLE 1

| No. | Electron transport layer First compound | Metal dopant | Electron transport capping layer | Driving voltage (relative value) | Current efficiency (relative value) |
|---|---|---|---|---|---|
| Example 1 | 2-1 | Yb | 1-53 | 91 | 107 |
| Example 2 | 2-1 | Yb | 1-12 | 93 | 105 |
| Example 3 | 2-1 | Yb | 1-66 | 90 | 110 |
| Example 4 | 2-1 | Yb | 1-99 | 90 | 111 |
| Example 5 | 2-7 | Yb | 1-53 | 87 | 116 |
| Example 6 | 2-7 | Yb | 1-12 | 88 | 114 |

TABLE 1-continued

| No. | Electron transport layer First compound | Metal dopant | Electron transport capping layer | Driving voltage (relative value) | Current efficiency (relative value) |
|---|---|---|---|---|---|
| Example 7 | 2-7 | Yb | 1-66 | 85 | 115 |
| Example 8 | 2-7 | Yb | 1-99 | 83 | 120 |
| Example 9 | 1-66 | Yb | 1-66 | 94 | 105 |
| Example 10 | 1-99 | Yb | 1-99 | 93 | 108 |
| Comparative Example 1 | A | Li | B | 100 | 100 |
| Comparative Example 2 | 2-1 | Li | — | 113 | 83 |
| Comparative Example 3 | 1-99 | Yb | — | 118 | 80 |
| Comparative Example 4 | 2-1 | Cs | c | 128 | 65 |
| Comparative Example 5 | D | — | E | 131 | 60 |

Referring to Table 1, it was found that the light-emitting devices according to an embodiment have lower driving voltage and higher current efficiency than the light-emitting devices of Comparative Examples 1 to 5.

A light-emitting device according to an embodiment has a low driving voltage and excellent efficiency and lifespan characteristics.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A light-emitting device comprising:

a first electrode;

a second electrode facing the first electrode;

an interlayer located between the first electrode and the second electrode; and an electron transport capping layer located outside the second electrode, wherein the interlayer includes an emission layer and an electron transport region, one of the electron transport region and the electron transport capping layer includes a first compound represented by Formula 1, and the other one includes the first compound, a second compound represented by Formula 2, or a combination thereof, and the electron transport region further includes a metal dopant:

Formula 1

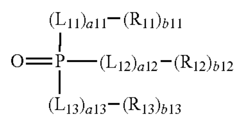

Formula 2

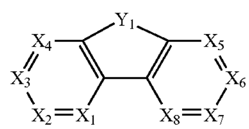

wherein, in Formula 1 and Formula 2, $Y_1$ is *—O—*', *—S—*', *—N[$(L_9)_{a9}$-$(R_9)_{b9}$]—*', *—C[$(L_9)_{a9}$-$(R_9)_{b9}$][$(L_{10})_{a10}$-$(R_{10})_{b10}$]—*', *—C[$(L_9)_{a9}$-$(R_9)_{b9}$]═C[$(L_{10})_{a10}$-$(R_{10})_{b10}$]—*', *—C[$(L_9)_{a9}$-$(R_9)_{b9}$]═N—*', or *—N═C[$(L_{10})_{a10}$-$(R_{10})_{b10}$]—*', $X_1$ is N or C[$(L_1)_{a1}$-$(R_1)_{b1}$], $X_2$ is N or C[$(L_2)_{a2}$-$(R_2)_{b2}$], $X_3$ is N or C[$(L_3)_{a3}$-$(R_3)_{b3}$], $X_4$ is N or C[$(L_4)_{a4}$-$(R_4)_{b4}$], $X_5$ is N or C[$(L_5)_{a5}$-$(R_5)_{b5}$], $X_6$ is N or C[$(L_6)_{a6}$-$(R_6)_{b6}$], $X_7$ is N or C[$(L_7)_{a7}$-$(R_7)_{b7}$], and $X_8$ is N or C[$(L_8)_{a8}$-$(R_8)_{b8}$], $L_1$ to $L_{13}$ are each a single bond, a $C_1$-$C_{20}$ alkylene group that is unsubstituted or substituted with at least one $R_{10a}$, a $C_2$-$C_{20}$ alkenylene group that is unsubstituted or substituted with at least one $R_{10a}$, a $C_2$-$C_{20}$ alkynylene group that is unsubstituted or substituted with at least one $R_{10a}$, a $C_3$-$C_{10}$ cycloalkylene group that is unsubstituted or substituted with at least one $R_{10a}$, a $C_1$-$C_{10}$ heterocycloalkylene group that is unsubstituted or substituted with at least one $R_{10a}$, a $C_3$-$C_{10}$ cycloalkenylene group that is unsubstituted or substituted with at least one $R_{10a}$, a $C_1$-$C_{10}$ heterocycloalkenylene group that is unsubstituted or substituted with at least one $R_{10a}$, a $C_6$-$C_{60}$ arylene group that is unsubstituted or substituted with at least one $R_{10a}$, a $C_1$-$C_{60}$ heteroarylene group that is unsubstituted or substituted with at least one $R_{10a}$, a divalent non-aromatic condensed polycyclic group that is unsubstituted or substituted with at least one $R_{10a}$, or a divalent non-aromatic condensed heteropolycyclic group that is unsubstituted or substituted with at least one $R_{10a}$, a1 to a13 are each 0, 1, 2, 3, 4, or 5, $R_1$ to $R_{13}$ are each hydrogen, deuterium, —F, —Cl, —Br, —I, a hydroxyl group, a cyano group, a nitro group, an amidino group, a hydrazino group, a hydrazono group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{10}$ cycloalkyl group unsubstituted or substituted with at least one $R_{10a}$, a $C_1$-$C_{10}$ heterocycloalkyl group unsubstituted or substituted with at least one $R_{10a}$, a $C_3$-$C_{10}$ cycloalkenyl group unsubstituted or substituted with at least one $R_{10a}$, a $C_1$-$C_{10}$ heterocycloalkenyl group unsubstituted or substituted with at least one $R_{10a}$, a $C_6$-$C_{60}$ aryl group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_1$-$C_{60}$ heteroaryl group unsubstituted or substituted with at least one $R_{10a}$, a $C_1$-$C_{60}$ heteroaryloxy group unsubstituted or substituted with at least one $R_{10a}$, a $C_1$-$C_{60}$ heteroarylthio group unsubstituted or substituted with at least one $R_{10a}$, a monovalent non-aromatic condensed polycyclic group unsubstituted or substituted with at least one $R_{10a}$, a monovalent non-aromatic condensed heteropolycyclic group unsubstituted or substituted with at least one $R_{10a}$, —Si($Q_1$)($Q_2$)($Q_3$), —B($Q_1$)($Q_2$), —N($Q_1$)($Q_2$), —P($Q_1$)($Q_2$), —C(═O)($Q_1$), —S(═O)($Q_1$), —S(═O)$_2$($Q_1$), —P(═O)($Q_1$)($Q_2$), or —P(═S)($Q_1$)($Q_2$), neighboring two or more of $R_1$ to Rio are optionally linked to each other to form a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, neighboring two or more of $R_{11}$ to $R_{13}$ are optionally linked to each other to form a $C_5$-$C_{60}$ carbocyclic group unsubstituted or substituted with at least one $R_{10a}$, or a $C_1$-$C_{60}$ heterocyclic group unsubstituted or substituted with at least one $R_{10a}$, b1 to b13 are each 1, 2, 3, 4, 5, 6, 7, or 8,

* and *' each indicate a binding site to a neighboring atom, and $R_{10a}$ is:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{11}$)($Q_{12}$)($Q_{13}$), —N($Q_{11}$)($Q_{12}$), —B($Q_{11}$)($Q_{12}$), —C(═O)($Q_{11}$), —S(═O)$_2$($Q_{11}$), —P(═O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, or a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{21}$)($Q_{22}$)($Q_{23}$), —N($Q_{21}$)($Q_{22}$), —B($Q_{21}$)($Q_{22}$), —C(═O)($Q_{21}$), —S(═O)$_2$($Q_{21}$), —P(═O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(═O)($Q_{31}$), —S(═O)$_2$($Q_{31}$), or —P(═O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each independently: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; or a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group, wherein the electron transport region includes an electron transport layer, wherein the electron transport layer includes the second compound and the metal dopant, and wherein an amount of the metal dopant in the electron transport layer is 5 wt % or less.

2. The light-emitting device of claim 1, wherein the electron transport capping layer includes the first compound, and the electron transport region includes the second compound and the metal dopant.

3. The light-emitting device of claim 1, wherein the metal dopant includes alkali metal, alkaline earth metal, rare earth metal, or a combination thereof.

4. The light-emitting device of claim 1, wherein the electron transport region further includes a hole-blocking layer, an electron control layer, an electron injection layer, or any combination thereof.

5. The light-emitting device of claim 1, wherein the electron transport region consists of the electron transport layer.

6. The light-emitting device of claim 1, wherein the electron transport layer is in direct contact with the second electrode.

7. The light-emitting device of claim 1, wherein the electron transport capping layer does not include a metal.

8. The light-emitting device of claim 1, wherein the electron transport capping layer is in direct contact with the second electrode.

9. The light-emitting device of claim 1, wherein the first compound is selected from Compounds 1-1 to 1-26 and 1-41 to 1-79:

1-1

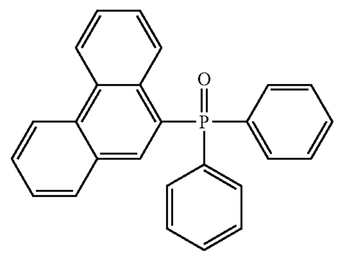

1-2

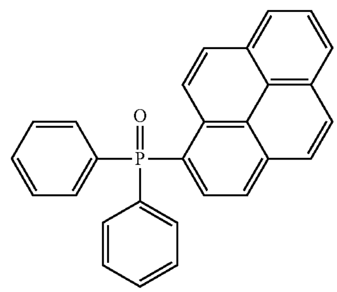

1-3

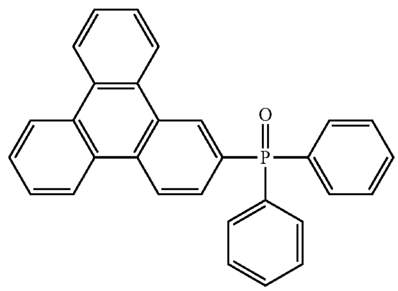

1-4

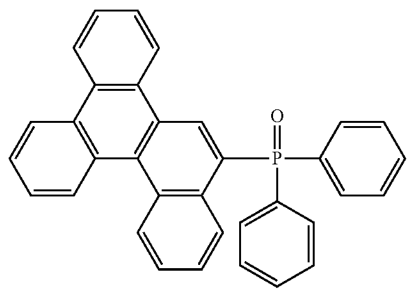

-continued
1-5
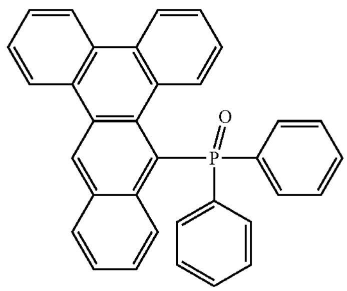
1-6
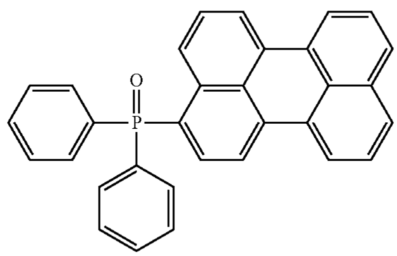
1-7
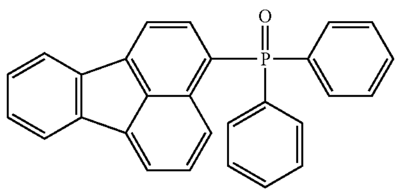
1-8
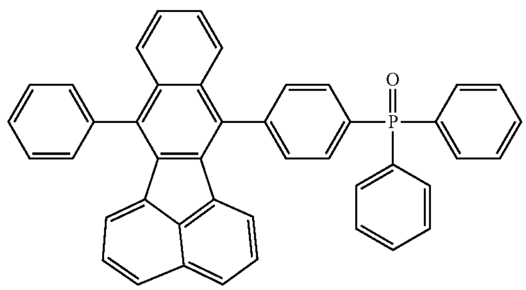
1-9
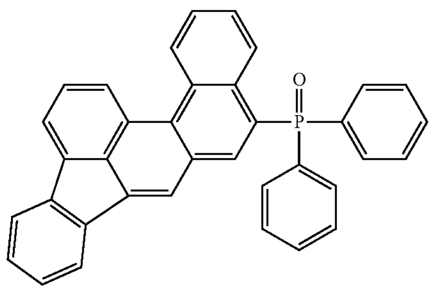
1-10
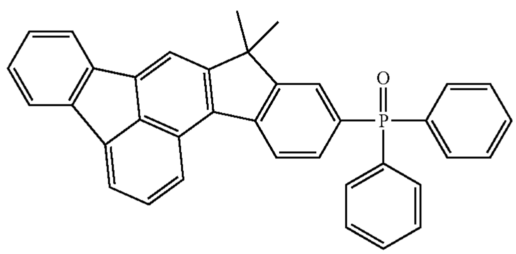
-continued
1-11
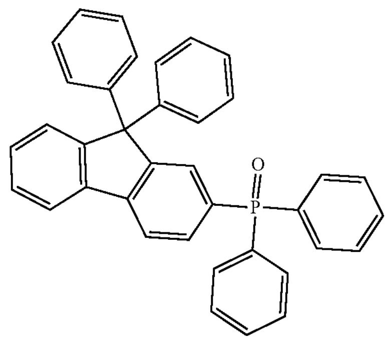
1-12
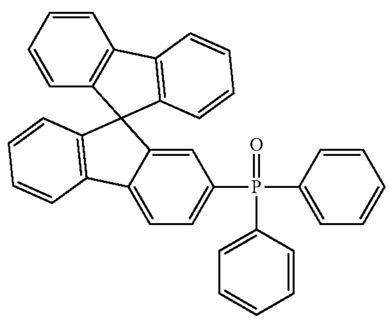
1-13
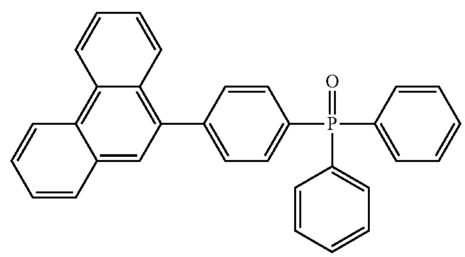
1-14
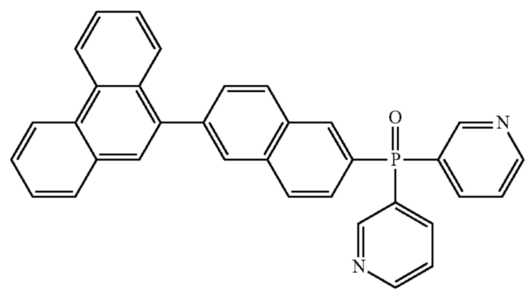
1-15
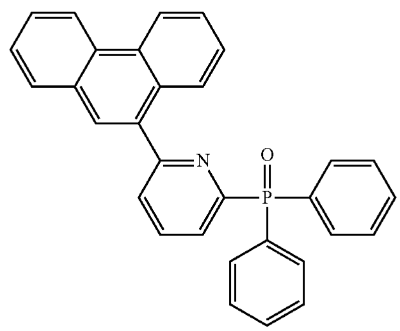

-continued
1-16
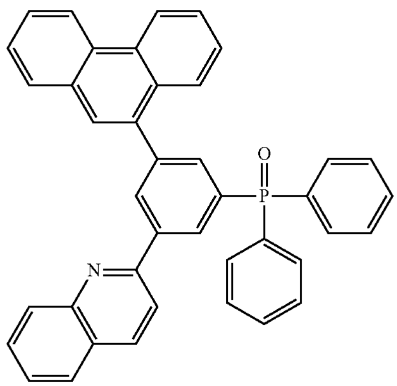
1-17
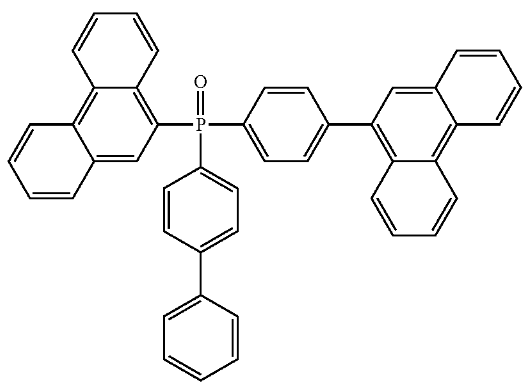
1-18
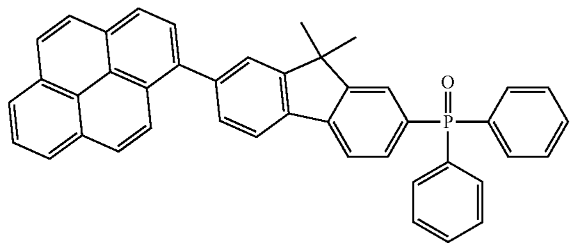
1-19
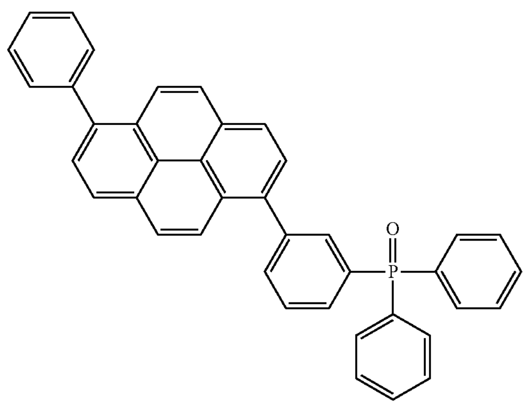
-continued
I-20
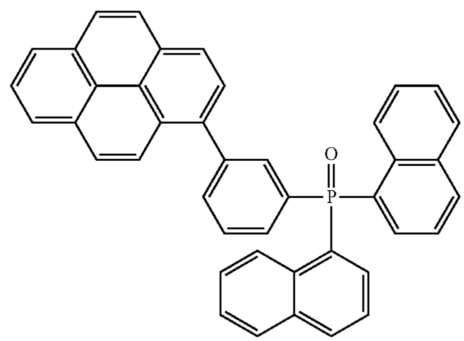
1-21
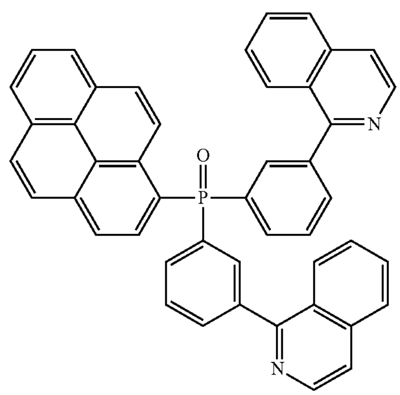
I-22
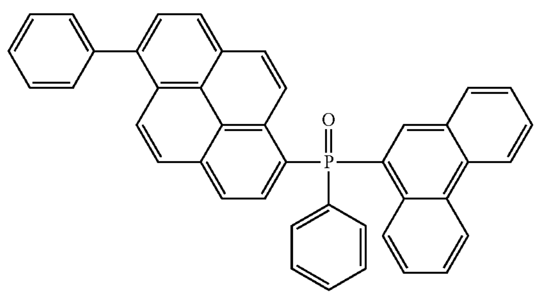
1-23
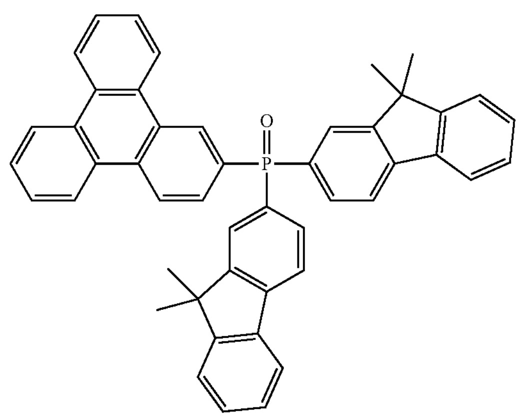

-continued
1-24
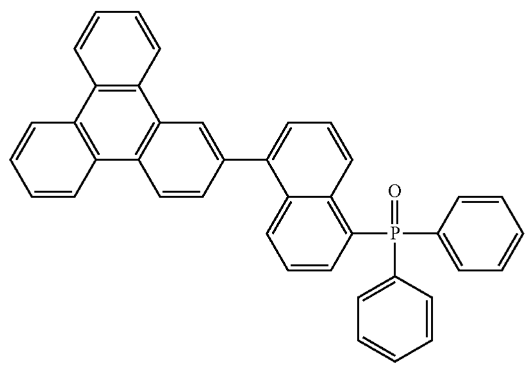
1-25
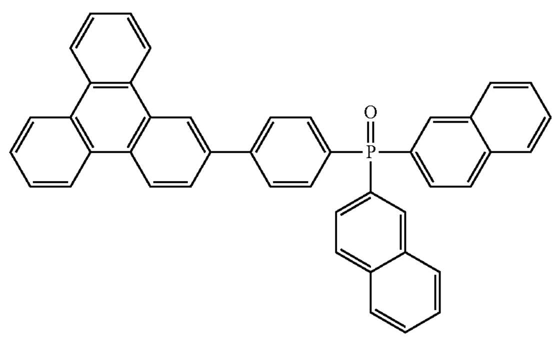
1-26
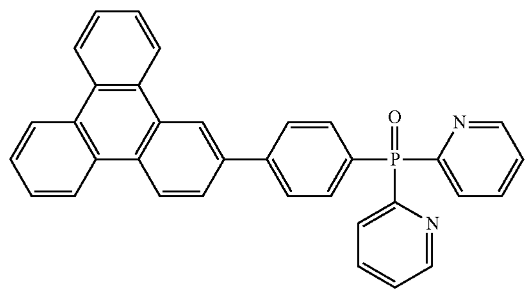
1-41
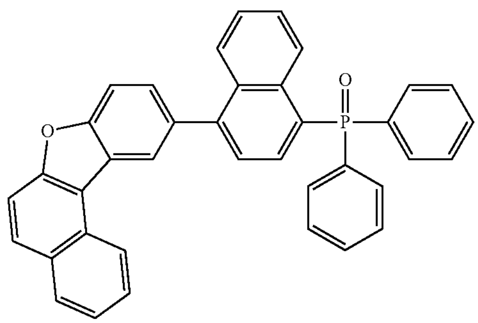
1-42
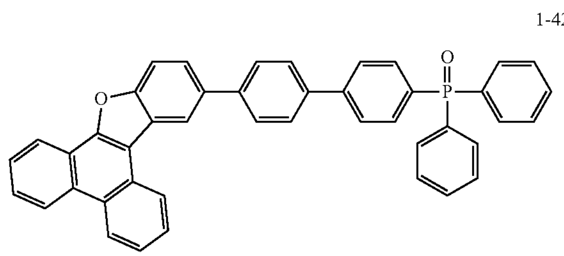
-continued
1-43
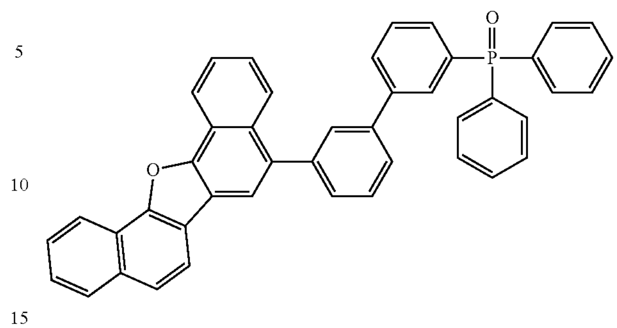
1-44
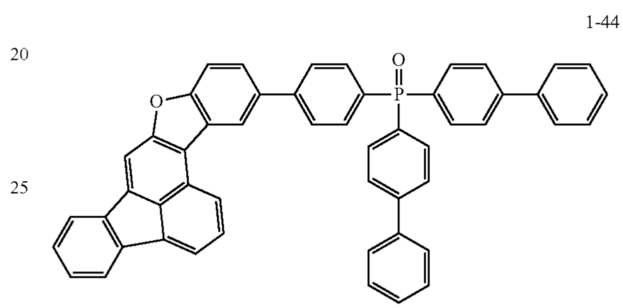
1-45
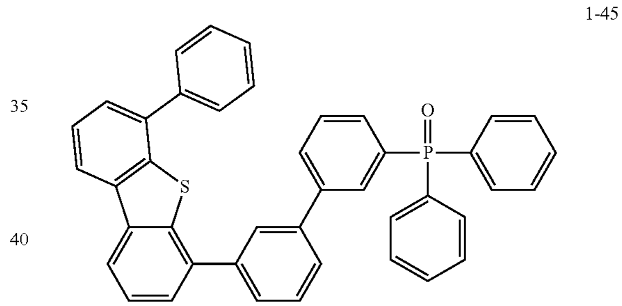
1-46
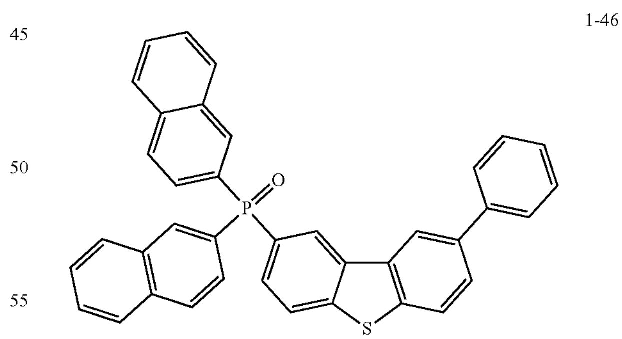
I-47
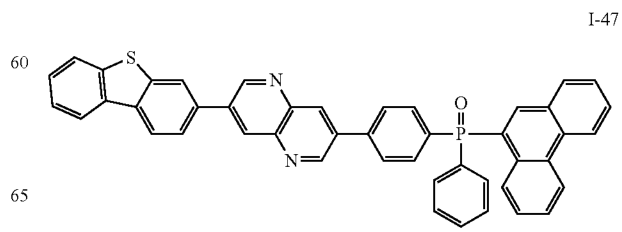

-continued
1-48
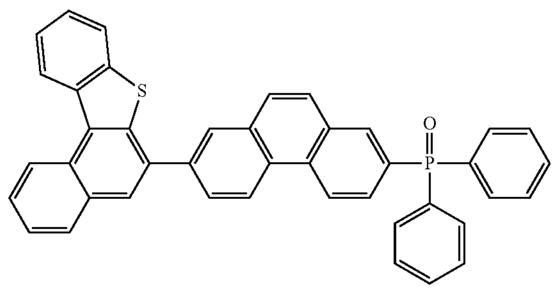
1-49
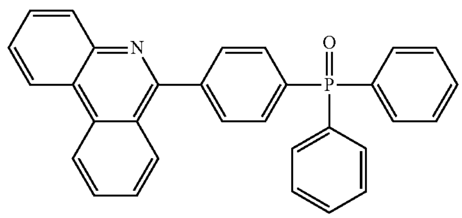
1-50
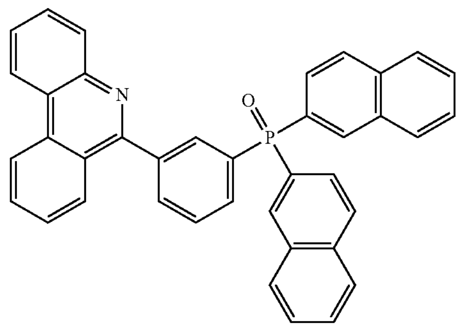
1-51
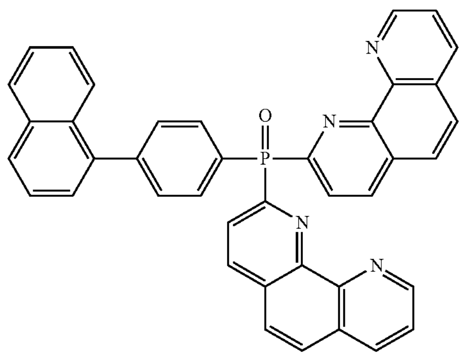
1-52
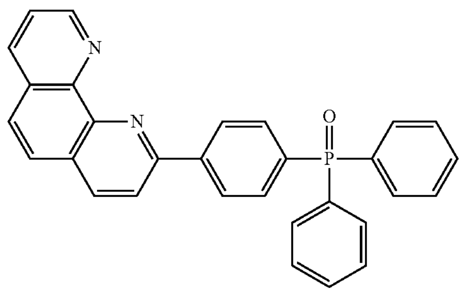
-continued
1-53
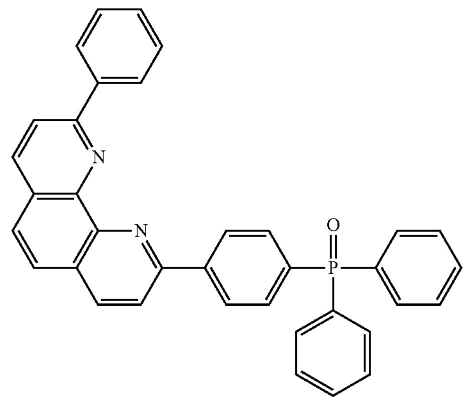
1-54
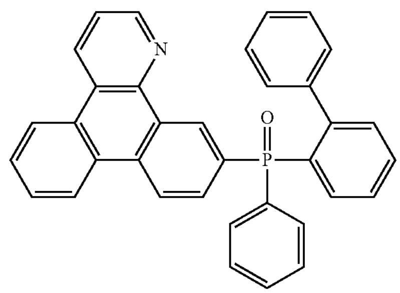
1-55
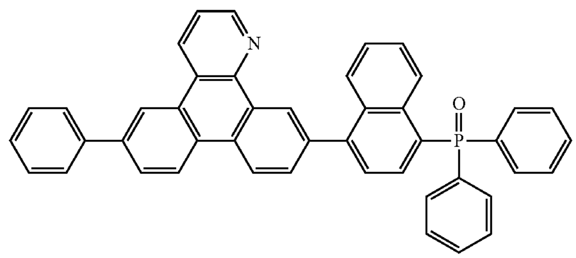
1-56
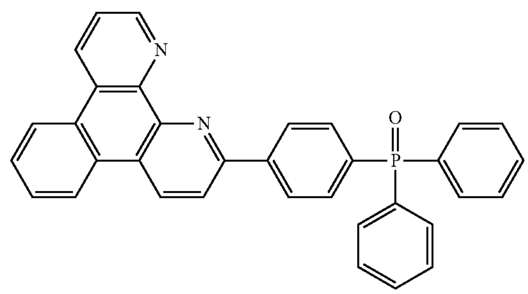
1-57
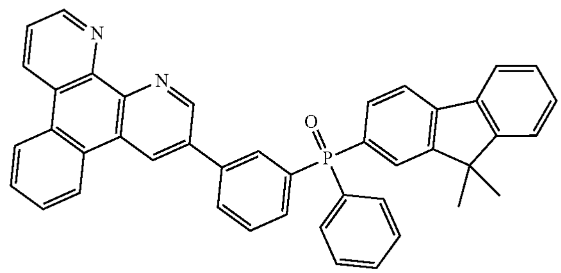

-continued
1-58
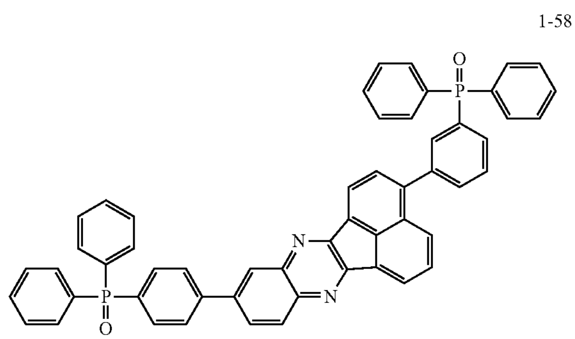
1-59
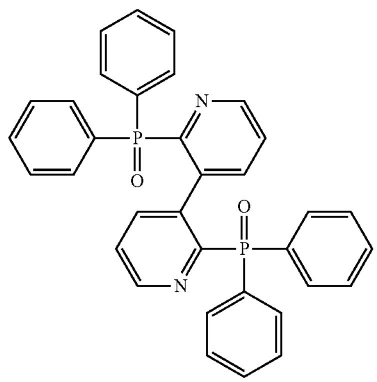
1-60
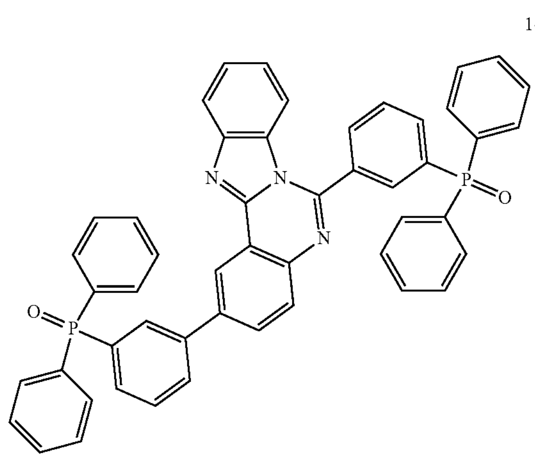
1-61
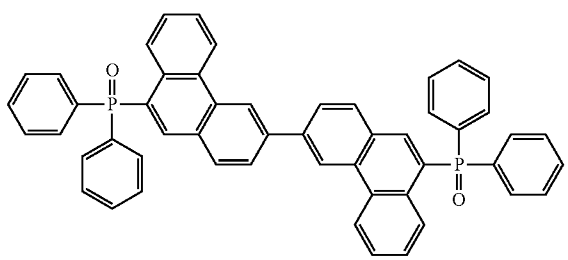
-continued
1-62
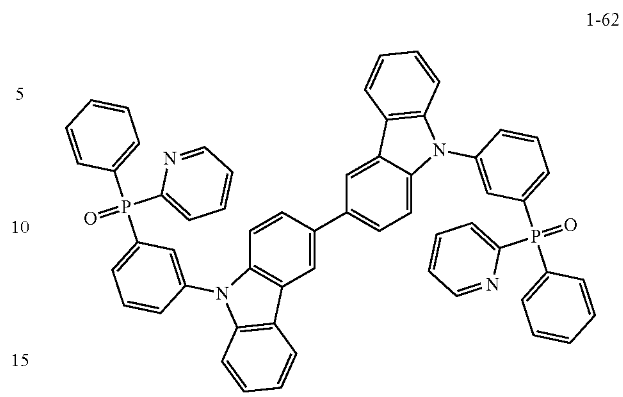
1-63
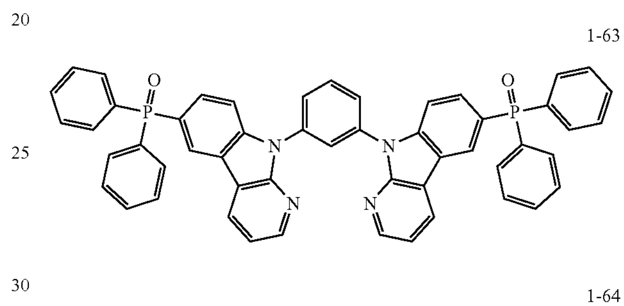
1-64
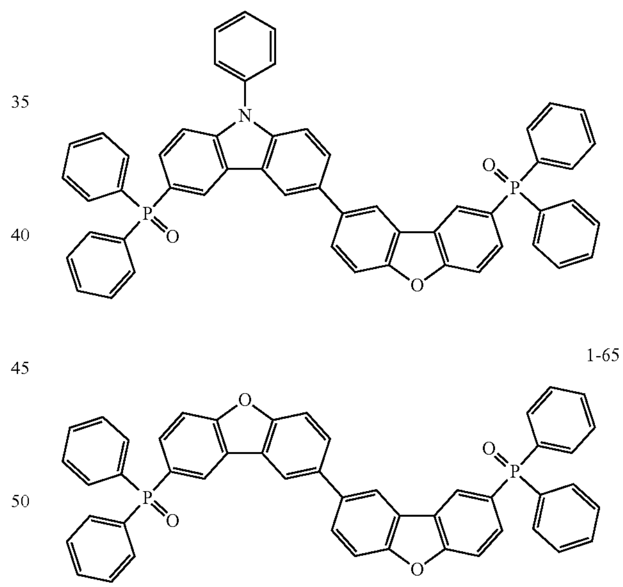
1-65
1-66
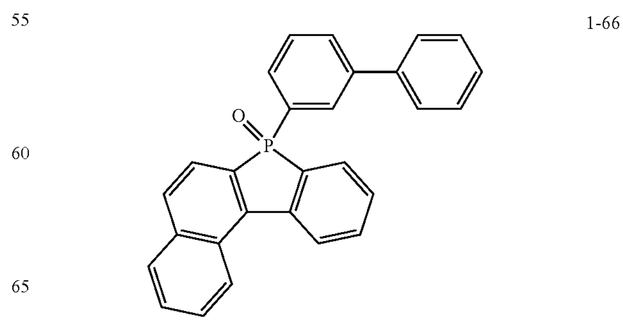

-continued
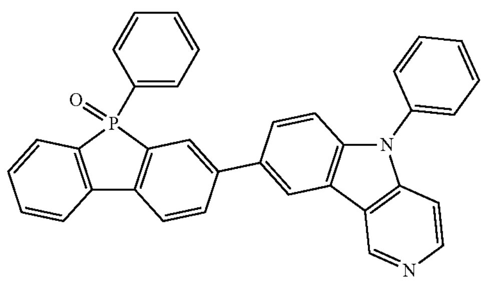
1-68
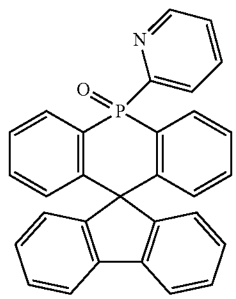
1-69
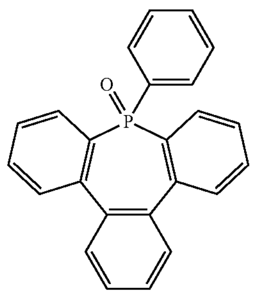
1-70
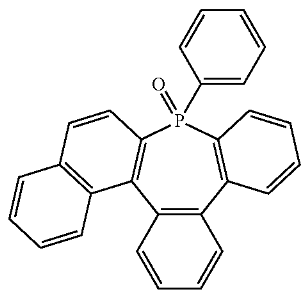
1-71
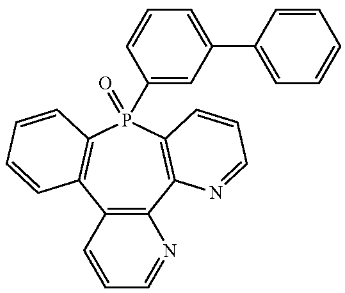
-continued
1-72
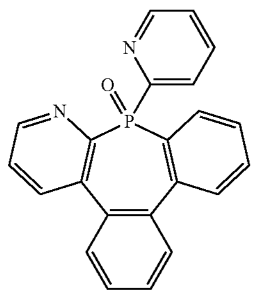
1-73
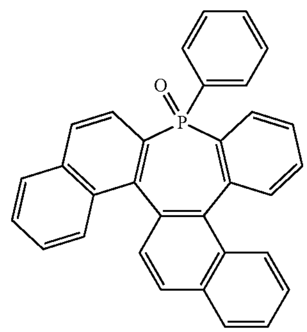
1-74
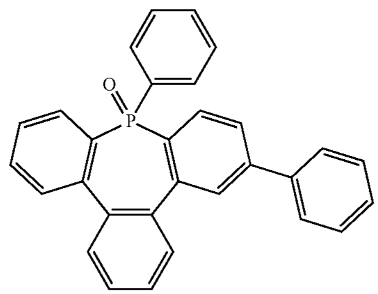
1-75
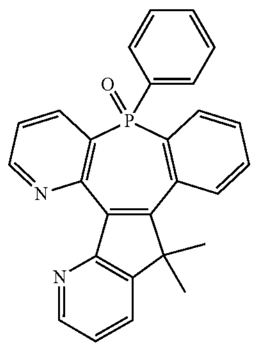
1-76
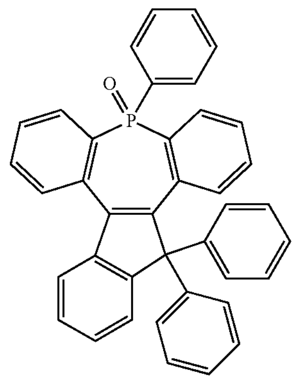

-continued
1-77
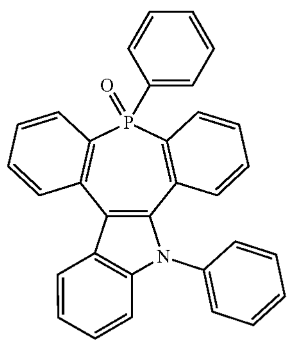
1-78
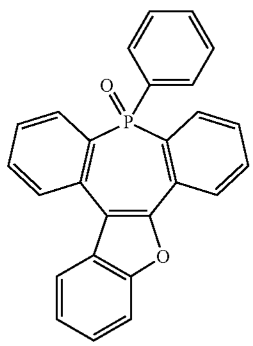
1-79
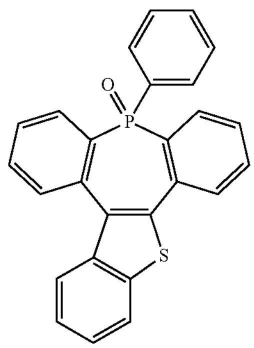
.
10. The light-emitting device of claim 1, wherein the second compound is selected from Compounds 2-1 to 2-18:
2-1
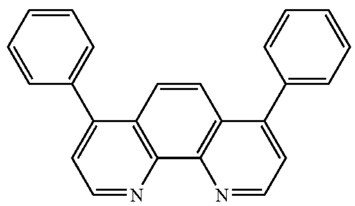
2-2
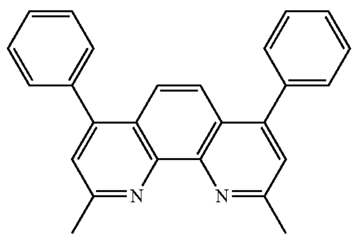
-continued
2-3
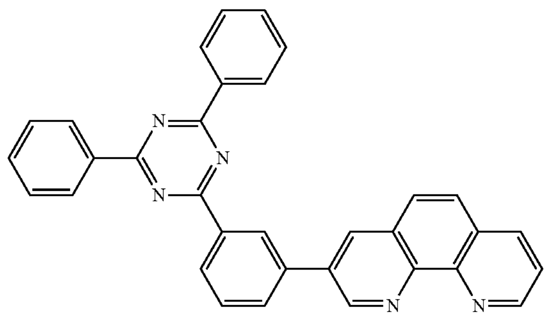
2-4
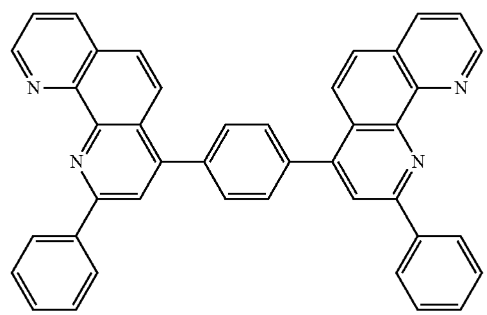
2-5
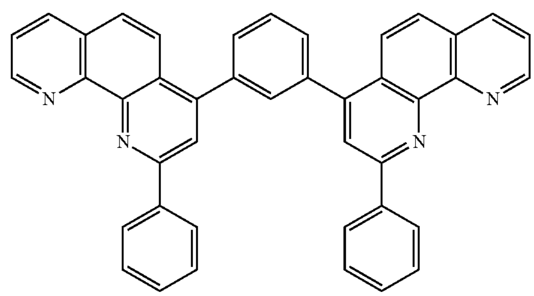
2-6
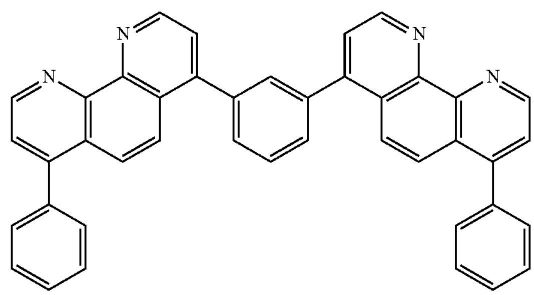
2-7
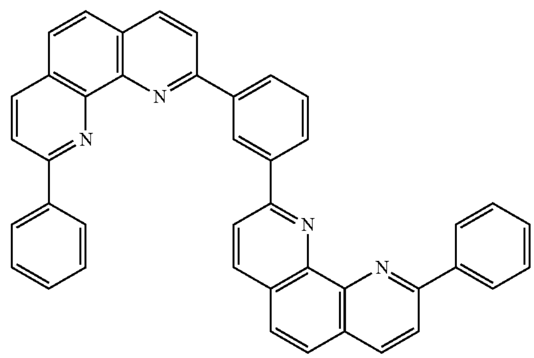

-continued
2-8
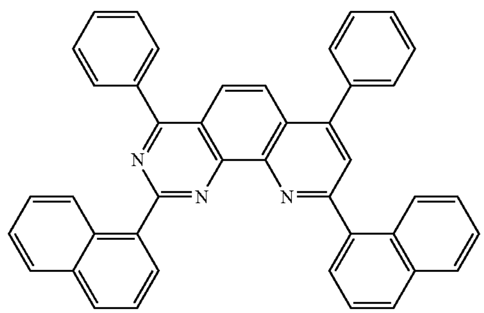
2-9
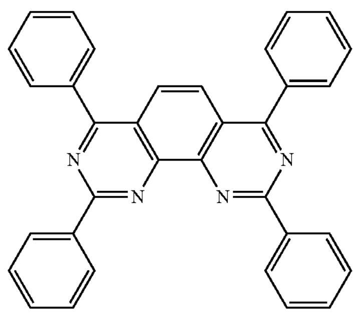
2-10
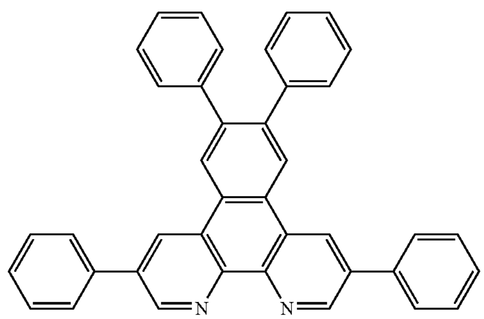
2-11
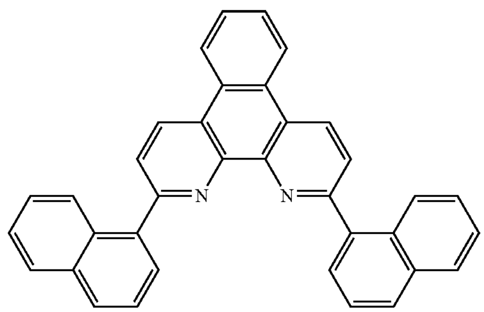
2-12
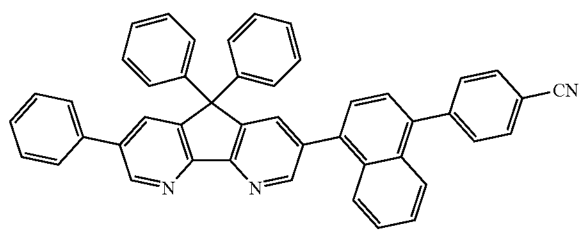
-continued
2-13
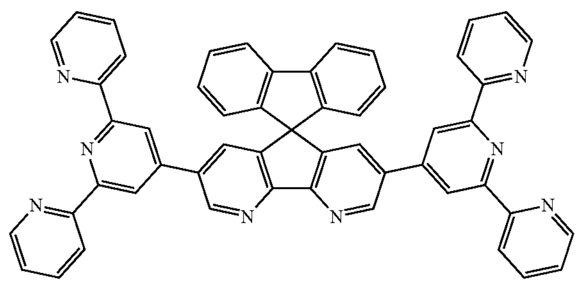
2-14
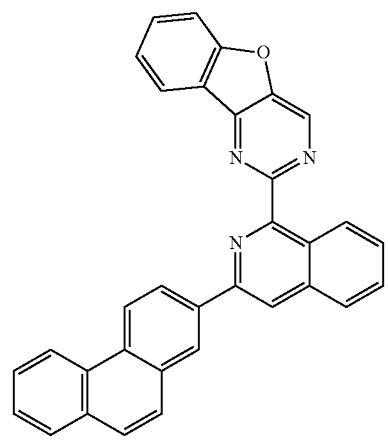
2-15
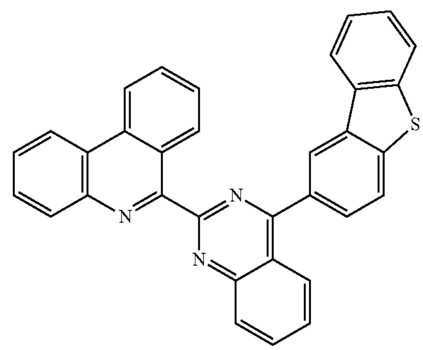
2-16
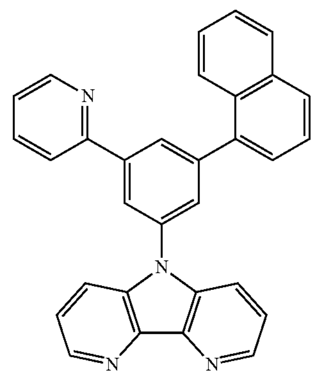

-continued 2-17

2-18

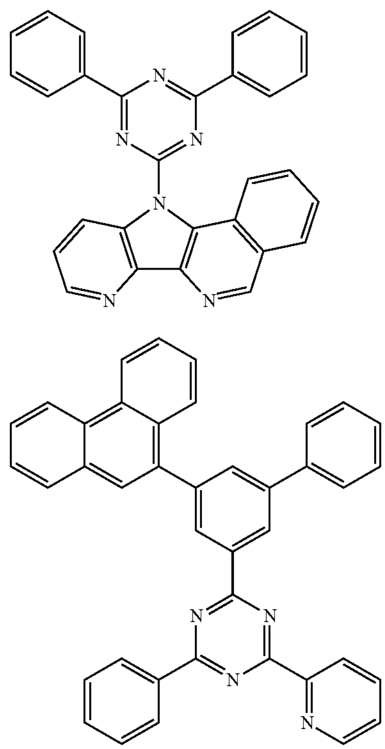

11. The light-emitting device of claim 1, wherein the emission layer includes a host and a dopant, and in the emission layer, an amount of the host is greater than an amount of the dopant based on weight.

12. The light-emitting device of claim 11, wherein the dopant includes a phosphorescent dopant, a fluorescent dopant, a delayed fluorescence material, or any combination thereof.

13. The light-emitting device of claim 1, further comprising a hole transport region located between the first electrode and the emission layer, wherein the hole transport region includes a hole injection layer, a hole transport layer, an electron-blocking layer, or any combination thereof.

14. The light-emitting device of claim 1, wherein the second electrode includes silver (Ag) in an amount of 95 wt % or more.

15. The light-emitting device of claim 1, wherein the second electrode includes magnesium (Mg), and an amount of the magnesium is 5 wt % or less.

16. An electronic apparatus comprising the light-emitting device of claim 1.

17. The electronic apparatus of claim 16, further comprising a thin-film transistor, wherein the thin-film transistor includes a source electrode and a drain electrode, and the first electrode of the light-emitting device is electrically connected to the source electrode or the drain electrode.

* * * * *